US011384134B2

(12) United States Patent
Herrin et al.

(10) Patent No.: US 11,384,134 B2
(45) Date of Patent: Jul. 12, 2022

(54) RECOMBINANT VECTOR AND EXPRESSION SYSTEM COMPRISING A NUCLEIC ACID ENCODING A VARIABLE LYMPHOCYTE RECEPTOR (VLR)

(71) Applicant: Emory University, Atlanta, GA (US)

(72) Inventors: Brantley R. Herrin, Decatur, GA (US); Max Dale Cooper, Atlanta, GA (US); Rudolf Ehrhardt, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 16/857,130

(22) Filed: Apr. 23, 2020

(65) Prior Publication Data

US 2020/0308247 A1   Oct. 1, 2020

Related U.S. Application Data

(62) Division of application No. 16/183,340, filed on Nov. 7, 2018, now abandoned, which is a division of application No. 15/308,535, filed as application No. PCT/US2015/028645 on Apr. 30, 2015, now Pat. No. 10,167,330.

(60) Provisional application No. 61/987,566, filed on May 2, 2014.

(51) Int. Cl.
    *C07K 14/46* (2006.01)
    *C12N 15/00* (2006.01)
    *C07K 14/725* (2006.01)

(52) U.S. Cl.
    CPC ........ *C07K 14/7051* (2013.01); *C07K 14/461* (2013.01); *C07K 2319/30* (2013.01); *C12N 15/00* (2013.01)

(58) Field of Classification Search
    CPC .................... C07K 14/7051; C07K 2319/30
    See application file for complete search history.

(56) References Cited

U.S. PATENT DOCUMENTS

| | | |
|---|---|---|
| 8,039,588 B2 | 10/2011 | Pancer |
| 8,212,018 B2 | 7/2012 | Pancer |
| 10,167,330 B2 | 1/2019 | Herrin |
| 2011/0165584 A1 | 7/2011 | Pancer |
| 2011/0230374 A1 | 9/2011 | Pancer |
| 2012/0189640 A1 | 7/2012 | Cooper |
| 2013/0287748 A1 | 10/2013 | June |
| 2014/0271635 A1 | 9/2014 | Brogdon |

FOREIGN PATENT DOCUMENTS

| | | |
|---|---|---|
| JP | H1118777 A | 1/1999 |
| WO | 2006083275 | 8/2006 |
| WO | 2008016854 | 2/2008 |
| WO | 2010065407 | 6/2010 |
| WO | 2013078425 | 5/2011 |

OTHER PUBLICATIONS

Alder MN, et al. (Dec. 23, 2005). 310(5756):1970-3. (doi: 10.1126/science.1119420).*
Bella et al. The leucine-rich repeat structure, Cell Mol Life Sci, 65, 2008, 2307-2333.
Binz et al. Engineering novel binding proteins from nonimmunoglobulin domains, Nature Biotechnology, 2005, vol. 23, No. 10, 1257.
Collins et al. Crystal structure of an anti-idiotype variable lymphocyte receptor, Acta Cryst. (2017). F73, 682-687.
Collins et al. Structural Insights into VLR Fine Specificity for Blood Group Carbohydrates, Structure, 2017, 25, 1667-1678.
Colman, Effects of amino acid sequence changes on antibody-antigen interactions, Res Immunol. 1994, 145(1):33-6.
Das et al., Organization of lamprey variable lymphocyte receptor C locus and repertoire development, Proc Natl Acad Sci U S A, 2013, 110(15):6043-8.
Gangloff et al. Functional Insights from the Crystal Structure of the N-Terminal Domain of the Prototypical Toll Receptor, Structure, 2013, 21(1):143-153.
Genbank, Variable lymphocyte receptor B [Lethenteron camtschaticum] Accession No. 2011, BAJ14925.1.
Gronwall et al. Engineered affinity proteins—Generation and applications, Journal of Biotechnology 140 (2009) 254 269.
Gunn et al. VLR recognition of TLR5 expands the molecular characterization of protein antigen binding by non-Ig-based antibodies, J Mol Biol. 2018, 430(9): 1350-1367.
Guo et al. Dual Nature of the Adaptive Immune System in Lampreys, Nature. 2009, 459(7248): 796-801.
Han et al. Antigen Recognition by Variable Lymphocyte Receptors, Science. 2008, 321(5897): 1834-1837.
Hirano et al. The Evolution of Adaptive Immunity in Vertebrates, Advances in Immunology, vol. 109, 125-157.
Kim et al. Structural Diversity of the Hagfish Variable Lymphocyte Receptors, J Biol Chem, 2007, 282, 9, 6726.
Kirchdoerfer et al. Variable Lymphocyte Receptor Recognition of the Immunodominant Glycoprotein of Bacillus anthracis Spores, Structure. 2012, 20(3): 479-486.
Lee et al. Design of a binding scaffold based on variable lymphocyte receptors of jawless vertebrates by module engineering, PNAS, 2012, vol. 109 , No. 9 , 3299-3304.
Matsushima et al. Leucine-Rich Repeats, Structure, Function, Evolution and Interaction with Ligands,Drug Design Reviews—Online (Discontinued) (2005) 2: 305. ABSTRACT.

(Continued)

*Primary Examiner* — Robert S Landsman
(74) *Attorney, Agent, or Firm* — Emory Patent Group

(57) ABSTRACT

This disclosure relates to variable lymphocyte receptors (VLRs) modifications such as humanized sequences and polypeptides comprising such sequences that specifically bind a target molecule and uses related thereto. In certain embodiments, the disclosure relates to recombinant polypeptide VLRs disclosed herein and variants thereof. In certain embodiments, this disclosure relates to treating or preventing a disease or condition comprising administering an effective amount of a recombinant polypeptide or variant disclosed herein to a subject in need thereof.

3 Claims, 9 Drawing Sheets
Specification includes a Sequence Listing.

(56) References Cited

OTHER PUBLICATIONS

Nakahara et al. Chronic lymphocytic leukemia monitoring with a lamprey idiotope-specific antibody, Cancer Immunol Res. 2013, 1(4): 223-228.
Paul, Fundamental Immunology, 1993, Raven Press, Chapter 9, Fv Structure and Diversity in Three Dimensions, 292-295.
Rudikoff et al. Single amino acid substitutions alter antigen-binding specificity, Proc Natl Acad Sci U S A. 1982, 79(6): 1979-1983.
So et al.. Harnessing 450 Million Years of Evolution: Lamprey Antibodies for Modern Biomarker Technology, Immpress Magazine, 2015.
Tasumi et al High-affinity lamprey VLRA and VLRB monoclonal antibodies, PNAS , 2009, vol. 106, No. 31, 12891-12896.
Yu et al. Purification and identification of cell surface antigens using lamprey monoclonal antibodies, Immunol Methods. 2012, 386(0): 43-49.
Yu et al. A lamprey monoclonal VLR antibody recognizes a novel plasma cell antigen, J Immunol May 1, 2013, 190 (1 Supplement) 114.11.
Yu et al. Identification of human plasma cells with a lamprey monoclonal antibody, JCI Insight. 2016, 1(3):e84738.

* cited by examiner

| Score | Expect | Method | Identities | Positives | Gaps |

313 bits(802)  4e-95  Compositional matrix adjust.  172/213(81%) 176/213(82%) 7/213(3%)

```
Query   1    CPAACTCSNNTVDCRSKGLTEIPTNLPETITIIYLHDNTIKVIPPGAFSPYKKLREIYLG
60
             CPAACTCSNN VDCR KGLTEIPTNLPETIT I L  NTIKVIPPGAFSPYKKLR I L
Sbjct   277  CPAACTCSNNIVDCRGKGLTEIPTNLPETITEIRLEQNTIKVIPPGAFSPYKKLRRIDLS
336

Query   61   SNQISELAPDAFQGLRSLNVLDLGTNKITELPKSLFEGLFSLQELFLCCNKINCLRVDAF
120
             +NQISELAPDAFQGLRSLN L L  NKITELPKSLFEGLFSLQ L L  NKINCLRVDAF
Sbjct   337  NNQISELAPDAFQGLRSLNSLVLYGNKITELPKSLFEGLFSLQLLLLNANKINCLRVDAF
396

Query   121  QDLHNLNHLALDQNKLQTIAKGTFSPLRAIQHMYLFGNPFICDCHLKWLADYLHIAMRWD
180
             QDLHNLN L+L  NKLQTIAKGTFSPLRAIQ M+L  NPFICDCHLKWLADYLH
Sbjct   397  QDLHNLNLLSLYDNKLQTIAKGTFSPLRAIQTMHLAQNPFICDCHLKWLADYLHTNPI--
454

Query   181  GKAVNDPDSARCTSPRRLANKRIGQIKSKKFRC  213    SEQ ID NO: 1
                    +    ARCTSPRRLANKRIGQIKSKKFRC
Sbjct   455  -----ETSGARCTSPRRLANKRIGQIKSKKFRC  482    SEQ ID NO: 72
```

FIG. 8

SLIT2-D2
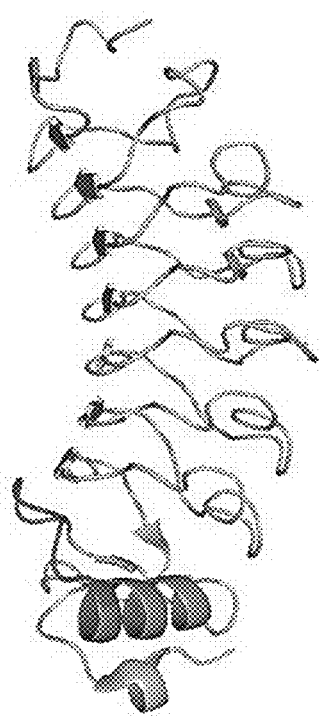
VLRB VLR4
(anti-BclA)
[same LRRCT loop as VLRB MM3]
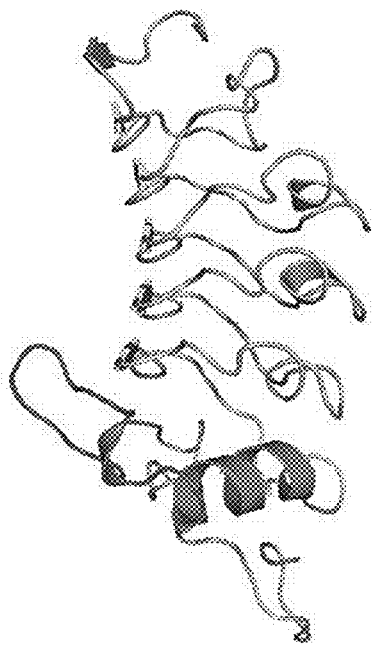
FIG. 13

RECOMBINANT VECTOR AND EXPRESSION SYSTEM COMPRISING A NUCLEIC ACID ENCODING A VARIABLE LYMPHOCYTE RECEPTOR (VLR)

CROSS-REFERENCE TO RELATED APPLICATIONS

This application is a division of U.S. patent application Ser. No. 16/183,340 filed Nov. 7, 2018, which is a division of U.S. patent application Ser. No. 15/308,535 filed Nov. 2, 2016, which is the National Stage of International Application No. PCT/US2015/028645 filed Apr. 30, 2015, which claims the benefit of priority to U.S. Provisional Application No. 61/987,566 filed May 2, 2014. The entirety of each of these applications is hereby incorporated by reference for all purposes.

STATEMENT REGARDING FEDERALLY FUNDED RESEARCH

This invention was made with government support under 5R01AI072435 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 13203USDIV2updated_ST25.txt. The text file is 124 KB, was created on Feb. 11, 2022, and is being submitted electronically via EFS-Web.

BACKGROUND

Studies of immunity indicate the emergence of two types of adaptive immune systems (AISs) in vertebrates. Humans generate a vast repertoire of Ig-domain-based T- and B-cell antigen receptors primarily by the assembly of Ig V-(D)-J gene segments and somatic hypermutation. Lampreys and hagfish have alternative AISs that are based on variable lymphocyte receptors (VLRs), the diversity of which is generated from leucine-rich repeat (LRR) cassettes. The combinatorial VLR assembly can generate a vast repertoire of receptors comparable in diversity to human immunoglobulins. See Han et al. Antigen recognition by variable lymphocyte receptors, Science, 2008 321:1834-183; Hirano et al., The evolution of adaptive immunity in vertebrates, Adv Immunol, 2011, 109:125-57; WO 2013/078425; US 2011/0230374; WO 2010/065407; and WO 2008/016854. Guo et al. report the adaptive immune system in lampreys. Nature, 2009, 459(7248):796-80. Tasumi et al. report high-affinity lamprey VLRA and VLRB monoclonal antibodies. Proc Natl Acad Sci USA, 2009, 106(31):12891-6. Nakahara et al. report chronic lymphocytic leukemia monitoring with a lamprey idiotope-specific antibody. Cancer Immunol Res, 2013, 1(4):223-228.
Binz et al., report engineering binding proteins from non-immunoglobulin domains. Nat Biotechnol., 2005, 23(10): 1257-68.
Lee et al. report a binding scaffold based on variable lymphocyte receptors of jawless vertebrates by module engineering. Proc Natl Acad Sci USA, 2012, 109(9): 3299-304.
References cited herein are not an admission of prior art.

SUMMARY

This disclosure relates to variable lymphocyte receptors (VLRs) modifications such as humanized sequences and polypeptides comprising such sequences that specifically bind a target molecule and uses related thereto. In certain embodiments, the disclosure relates to recombinant polypeptide VLRs disclosed herein and variants thereof. In certain embodiments, this disclosure relates to treating or preventing a disease or condition comprising administering an effective amount of a recombinant polypeptide or variant disclosed herein to a subject in need thereof.

In certain embodiments, the disclosure relates to recombinant polypeptide VLRs that specifically bind human cells, such as plasma cells, B-cells, or T-cells.

In certain embodiments, the disclosure relates to conjugating a human antibody Fc sequence to a variable lymphocyte receptor optionally modified to include humanized amino acid sequences. In certain embodiments, the disclosure relates to grafting amino acid positions from a variable lymphocyte receptor (VLR) of a jawless vertebrate into a human protein comprising a leucine-rich repeat (LRR) sequence. In certain embodiments, the disclosure relates to creating protein display libraries with similarity to variable lymphocyte receptors sequences that are enriched with human like sequences and identifying sequences therein compatible for use in therapeutic applications. In certain embodiments, the modified humanized sequence is conjugated to a human antibody Fc sequence recognized by Fc receptors and complement sufficient for activating effector functions of a human immune system.

In certain embodiments, the disclosure relates to isolated modified human amino acid sequences that specifically bind a molecule made by a process comprising, providing an amino acid sequence of a variable lymphocyte receptors (VLR) of a jawless vertebrate that binds an molecule; estimating which amino acids in the variable lymphocyte receptor that are in closest spatial proximity to the bound molecule and/or provide ionic interactions, and/or hydrogen bonding and/or provide Van der Waals force to the bound molecule providing target amino acids in the variable lymphocyte receptor; providing a known human amino acid sequence with greater than 20, 25, or 30% or more sequence identity to the variable lymphocyte receptor (VLR) amino acid sequence; substituting the target amino acids and a sufficient number of amino acids surrounding the target amino acids in the variable lymphocyte receptor within the known human amino acid sequence to provide a modified human amino acid sequence configured to specifically bind the molecule; and expressing the modified human amino acid sequence from a recombinant nucleic acid.

In certain embodiments, the disclosure relates to recombinant vectors comprising nucleic acids that encode modified known human amino acid sequences made by processes disclosed herein. In certain embodiments, the disclosure relates to expression system comprising recombinant vectors comprising nucleic acids that encode modified known human amino acid sequences made by processes disclosed herein.

In certain embodiments, this disclosure relates to fusion proteins comprising a modified human amino acid sequence disclosed herein and a human Fc sequence or fragment thereof that are able to institute adaptive immune functions.

In certain embodiments, this disclosure relates to recombinant polypeptide comprising the sequence XLXLXXNKLQTIAKGTFSPLRAIQXMXLXX (SEQ ID NO: 38) wherein X at each position is individually and independently any amino acid provided that the polypeptide does not contain at least one of the following wild-type Slit2-D2 sequences selected from (SEQ ID NO: 16) LLSLYD, and (SEQ ID NO: 17) TMHLAQ. In certain embodiments, recombinant polypeptide further comprises a human Fc sequence. In certain embodiments, recombinant polypeptide has the sequence YLDLNNNKLQTIAKGTFGTFSPLRAIQHMWLY (SEQ ID NO: 66), YLDLNNNKLQTIAKGTFGTFSPLRAIQHMWLYQ (SEQ ID NO: 67), or YLDLNNNKLQTIAKGTFGTFSPLRAIQHMWLYG (SEQ ID NO: 68). In certain embodiments, recombinant polypeptide is capable of specifically binding plasma cells but not B cells.

In certain embodiments, the disclosure relates to recombinant polypeptide comprising the MM3 sequence SEQ ID NO: 56 or variants thereof. In certain embodiments, the disclosure relates to a recombinant vector comprising a nucleic acid encoding the recombinant polypeptide. In certain embodiments, the disclosure relates to an expression system comprising the vector.

Figure 1:
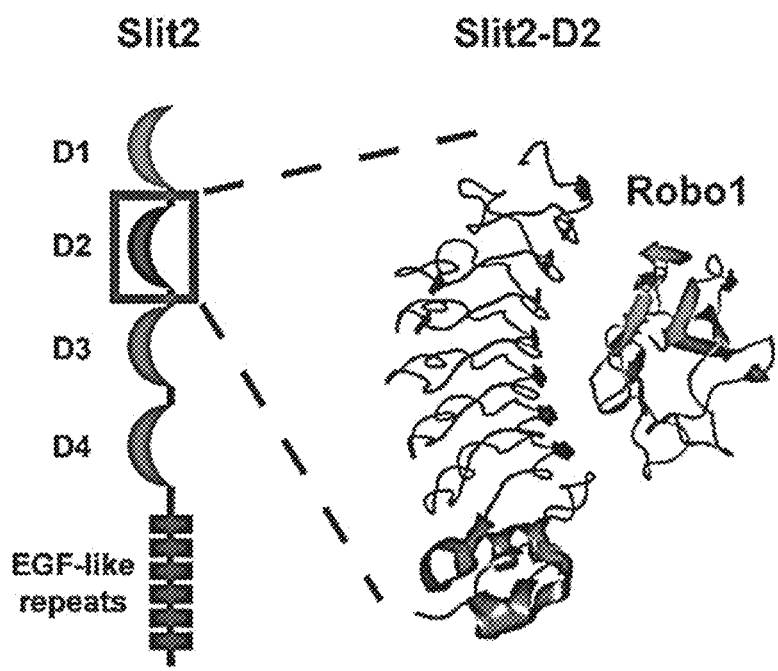
FIG. 1 illustrates human Slit2-D2 as a humanized scaffold for VLRs. The second VLR-like RRR domain of Slit2 (Slit-D2) has been co-crystallized with its ligand Robo1, which binds to the beta-strands of the concave surface in the same way that antigen bind VLRs.
Figure 2:
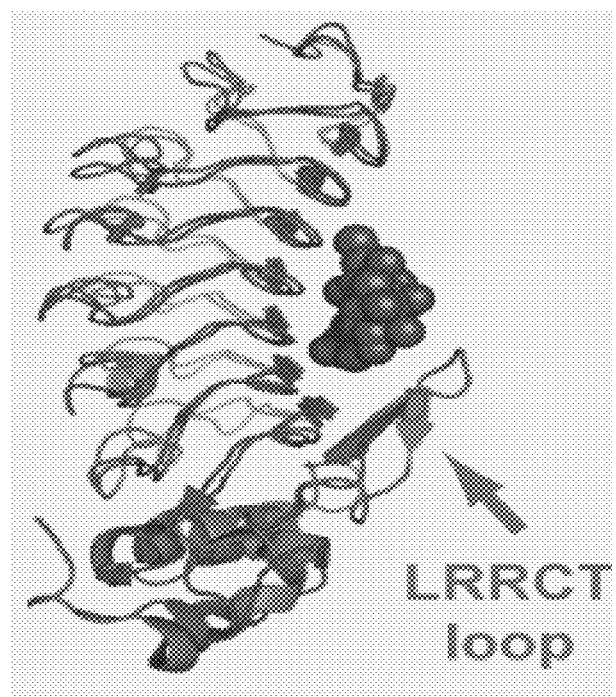
FIG. 2 illustrates alignment of VLR and Slit2-D2 showing substantial overlap.
Figure 3:
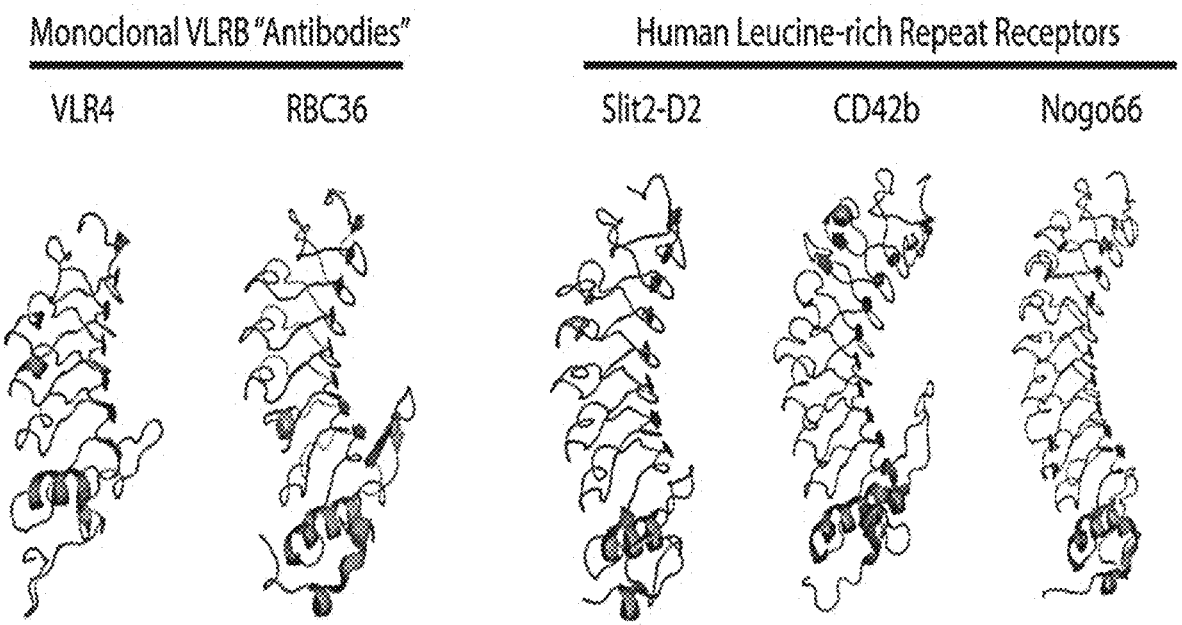
FIG. 3 illustrates the tertiary structure of lamprey VLRB antibodies and human LRR receptors. (Left) Tertiary structure of lamprey VLRB clones specific for *Bacillus anthracis* (VLR4) and H trisaccharide (RBC36). (Right) Humans express many leucine-rich repeat receptors with tertiary structures similar to lamprey VLRB. For example, Slit-D2, CD42b, and Nogo-66 receptors have the same crescent-shape as VLRB, including a concave surface composed of parallel beta-sheets.
Figure 4:
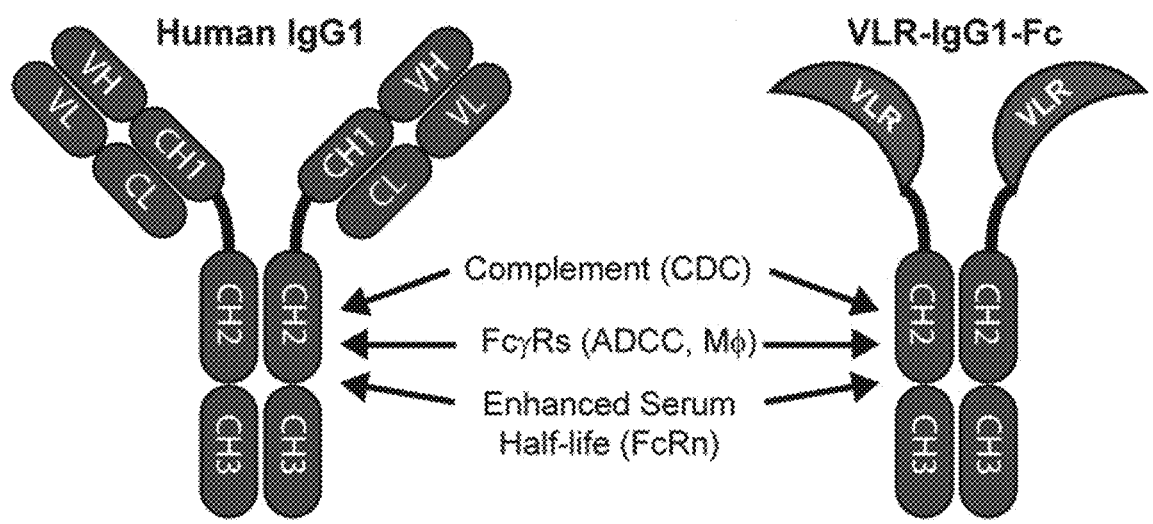
FIG. 4 illustrates coupling of VLRB specificity to human immune effector mechanisms. (Left) Human IgG1 antibodies are composed of a heavy chain with three constant domains (CH1-CH3) and one variable (VH) and a light chain with one constant domain (CL) and one variable domain (VL). The variable domains are responsible for antigen binding, while the CH2 and CH3 domains function to link the antibodies to immune effector functions including complement-dependent cytotoxicity (CDC), antibody-dependent cellular cytotoxicity (ADCC), and phagocytosis of antibody-coated cells by macrophages (Mb). The heavy chain constant region also enhances the half-life of antibodies in circulation by interaction with FcRn, which recycles the antibodies from endosomes. (Right) Fusion of the VLRB variable domain to the CH2 and CH3 domains of IgG1 will couple VLRB specificity to human mechanisms of immune clearance.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

The terms "protein" and "polypeptide" refer to compounds comprising amino acids joined via peptide bonds and are used interchangeably. In certain embodiments, the N-terminus may be substituted with one or more acetyl or alkanoyl, groups, and the C-terminus may be an amide.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements, as described below.

The term "a nucleic acid sequence encoding" a specified polypeptide refers to a nucleic acid sequence comprising the coding region of a gene or in other words the nucleic acid sequence which encodes a gene product. The coding region may be present in cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements.

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example the polypeptides GGGGGG (SEQ ID NO: 79) and GGGGT (SEQ ID NO: 80) have a sequence identity of 4 out of 5 or 80%. For example, the polypeptides GGGPPP (SEQ ID NO: 81) and GGGAPPP (SEQ ID NO: 82) have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q.

As used herein, the term "conjugate" refers to the joining of two molecular entities by covalent bonds. The molecular entities may be covalently bonded directly or through linking groups using standard synthetic coupling procedures. For examples, two peptides may be linked together by simultaneous polypeptide expression typically referred to as a fusion or chimeric protein. One or more amino acids may be inserted into polypeptide as a linking group by incorporation of corresponding nucleic acid sequences into the expression vector. Other contemplated linking groups include polyethylene glycols or hydrocarbons terminally substituted with amino or carboxylic acid groups to allow for amide coupling with proteins having amino acids side chains with carboxylic acid or amino groups respectively. Alternatively the amino and carboxylic acid groups can be substituted with other binding partners such as an azide and an alkyne which undergo copper catalyzed formation of triazoles. In another example of conjugation, polypeptides are expressed to contain naturally or non-naturally occurring amino acids containing a thiol group. The thiol group can be substituted for an amino group in coupling reactions with carboxylic acids, or two thiol groups when exposed to oxidative conditions react to form disulfides.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: $amp^r$, $cam^r$, $tet^r$, $blasticidin^r$, $neo^r$, $hyg^r$, $abx^r$, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferaseI (galT), feedback-insensitive α subunit of anthranilate synthase (OASA1D), 2-deoxyglucose (2-DOGR), benzyladenine-N-3-glucuronide, E. coli threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$ or $^{131}I$) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the disclosure relates to recombinant polypeptides comprising sequences disclosed herein or variants or fusions thereof wherein the amino terminal end or the carbon terminal end of the amino acid sequence are optionally attached to a heterologous amino acid sequence, label, or reporter molecule. In certain embodiments, the disclosure relates to the recombinant vectors comprising a nucleic acid encoding a polypeptide disclosed herein or chimeric protein thereof.

In certain embodiments, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene.

In certain embodiments, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

Variable Lymphocyte Receptor (VLR)

In certain embodiments, the disclosure relates to methods of producing a specific binding agent to a molecule comprising, administering a molecule to a jawless vertebrate under conditions such that a cell containing a variable lymphocyte receptor (VLR) binds the molecule and plasmacytes of the jawless vertebrate produce an variable lymphocyte receptor (VLR) that binds the molecule. Providing an amino acid sequence of the variable lymphocyte receptors (VLR) that binds a target molecule can be accomplished by a variety of methods. Yu et al. report the generation of panels of monoclonal VLR antibodies from lamprey larvae immunized with human T cells and the use of a recombinant monoclonal VLR antibody for antigen purification and mass spectrometric identification. See J Immunol Methods, 2012, 386(1-2):43-9 entitled "Purification and identification of cell surface antigens using lamprey monoclonal antibodies."

In certain embodiments, the disclosure relates to recombinant polypeptides comprising a VLR having VLR amino acid sequences disclosed herein, sequence or variants thereof. In certain embodiments, the disclosure relates to recombinant polypeptides comprising VLR sequences and other polypeptide sequences such as fluorescent proteins, tags, or markers such that the recombinant peptide is not naturally occurring. In certain embodiments, the disclosure relates to recombinant proteins made by the process of exposing a jawless vertebrate to an antigen under conditions such that an antibody is formed, wherein the antigen is such that the jawless vertebrate does not naturally experience exposure to such antigen.

In certain embodiments, the variant comprises 1, 2, 3, 4, 5, 6, 7, 8, 9 or 10 amino acid substitutions or has more than 50, 60, 70, 75, 80, 85, 90, 95, 96, 97, 98, or 99% identity or similarity thereof. In certain embodiments, the variants provide a non-naturally occurring sequence. In certain embodiments, the amino acid substitutions are conserved amino acid substitutions. In certain embodiments, the amino acid substitutions are not within a XXLXLXX (SEQ ID NO: 21) within VLR the VLR, e.g., MM3, wherein X is any amino acid and L may be leucine or isoleucine. In certain embodiments, the recombinant nucleic acid encodes VLR MM3 or variants thereof. In certain embodiments, a recombinant vector comprises a nucleic acid encoding VLR disclosed herein or variants thereof. In certain embodiments, the disclosure relates to an expression system comprising a recombinant vector of disclosed herein.

In certain embodiments, the disclosure relates to a recombinant VLR disclosed herein or variant thereof made by the processes of expressing a nucleic acid encoding the protein or variant thereof in an expression system.

Modified Human Sequences from VLR by Grafting Target Sequences

In certain embodiments, the disclosure relates to isolated modified human amino acid sequences that specifically binds a molecule made by a process comprising, providing an amino acid sequence of a variable lymphocyte receptors (VLR) of a jawless vertebrate that binds an molecule; estimating which amino acids in the variable lymphocyte receptor that are in closest spatial proximity to the bound molecule and/or provide ionic interactions, and/or hydrogen bonding and/or provide Van der Waals force to the bound molecule providing target amino acids in the variable lymphocyte receptor; providing a known human amino acid sequence with greater than 20, 25, or 30% or more sequence identity to the variable lymphocyte receptor (VLR) amino acid sequence; substituting the target amino acids and a sufficient number of amino acids surrounding the target amino acids in the variable lymphocyte receptor within the known human amino acid sequence to provide a modified human amino acid sequence configured to specifically bind the molecule; and expressing the modified human amino acid sequence from a recombinant nucleic acid.

The jawless vertebrates, lamprey and hagfish, have an adaptive immune system composed of clonally diverse lymphocytes that express variable lymphocyte receptors (VLRs). The germ-line VLRB gene is incomplete, consisting of invariant 5' and 3' constant regions separated by a non-coding intervening sequence. The 5' constant region encodes a signal peptide and part of the N-terminal LRR (LRR-NT). The 3' constant region encodes for a portion of the LRR-CT and an invariant stalk region. The incomplete germ-line gene is flanked by hundreds of partial LRR gene segments. In developing lymphocytes, the flanking LRR gene segments are randomly and sequentially copied into the incomplete VLRB gene. As each LRR gene segment is copied into the locus, it replaces a portion of the intervening sequence. The assembly mechanism continues until all of the intervening sequence is replaced with LRR modules and a functional VLRB is expressed. VLRB gene assembly occurs on only one allele, such that each lymphocyte expresses one VLRB gene. The VLRB gene assembly mechanism can produce greater than $10^{14}$ unique antigen receptors, which rivals the theoretical diversity of the human antibody repertoire.

The mature VLRB gene encodes for a crescent-shaped protein, with amino acid sequence diversity concentrated on the concave surface. The concave surface is composed of parallel β-strands and a C-terminal variable loop. Each LRR subunit contributes one β-strand, and each β-strand has five variable amino acid positions. VLRB antibodies also have variable numbers of LRR subunits. The smallest VLRB antibodies have 4 LRR subunits and the largest have 11 LRR subunits. Each LRR subunit increases the curvature of the concave surface by about 10° and increases the concave surface area by about 220 Å. The C-terminal LRR, LRR-CT, encodes a loop of variable length and sequence composition that projects above the concave surface. Immunization with particulate antigens, such as *Bacillus anthracis* exosporium or human red blood cells (RBCs), induces antigen-binding VLRB+ cells to proliferate and differentiate into plasmacytes. The plasmacytes secrete multivalent VLRB antibodies that circulate in the blood. Each secreted VLRB antibody is composed of identical VLRB polypeptide chains arranged into a pentamer or tetramer of dimers that is held together by disulfide bonds at the C-terminus of the flexible, invariant stalk region. Due to this multivalency, VLRB antibodies bind to their antigens with high avidity.

VLRB cDNAs expressed in mammalian cells lines (HEK-293T and CHO cells) are secreted into the tissue culture supernatant as disulfide-linked, multivalent antibodies, like VLRB in vivo. The recombinant VLRB antibodies are extraordinarily stable. They retain their antigen binding ability after exposure to extremes of pH (<1.5 and >12) and temperature (36 hours at 55° C.). To isolate antigen-specific VLRB clones, a VLRB cDNA library is prepared from the lymphocytes of immunized lampreys. The VLRB cDNAs are transfected into HEK-293T, and the VLRB-containing tissue culture supernatants are screened for antigen binding. The monoclonal VLRB antibodies are highly specific for the immunizing antigen. VLRB antibodies specific for the BelA spore-coat protein of *B. anthracis* faithfully (7 of 7) discriminated between BelA of *B. anthracis* and *B. cereus* despite 90% amino acid sequence identity.

X-ray crystallography of a VLRB antibody (RBC-36) complexed with the human erythrocyte H-trisaccharide antigen confirmed that the concave surface is the site of antigen binding. The H-trisaccharide interaction was stabilized by hydrogen bonds and van der Waals contacts with amino acids in six of the seven β-strands on the concave VLRB surface. The LRR-CT of RBC-36 forms an extended loop that contributes a key interaction with the galactose ring of the H-trisaccharide via a tryptophan (TRP204) residue near the tip of the loop.

In experiments VLRB proteins were immunogenic in mice after repeated immunization. The immunogenicity of VLRB antibodies limits their potential as therapeutic reagents in humans. Leucine-rich repeat receptors structurally similar to VLRB are found in vertebrates, invertebrates, plants, and prokaryotes. Several human leucine-rich repeat receptors, such as Slit-family proteins (Slit 1, 2, and 3), CD42b, and Nogo-66 have structural overlap to VLRB. Sequences of VLRB antibody (RBC36) responsible for antigen binding can be grafted onto a structurally similar human LRR receptor (Slit2-D2) to "humanize" the VLRB. In practice, not all of the amino acids on the beta-sheets of the concave surface would have to be substituted because select amino acids are likely to participate in antigen binding. Moreover, a high affinity VLRB that exists primarily in the antigen-bound state in vivo would mainly expose the fully humanized convex surface to the humoral immune system. Both Slit2-D2 and CD42b are secreted proteins in humans and bind to their natural ligands, Robo1 and von Willebrand Factor (vWF) respectively, on the concave surface. Grafting of the VLRB sequences to these human LRR receptors would add the antigen-binding epitope of the VLRB antibody, while abolishing binding to their natural ligands.

Specific reference is made to Han et al. Science, 2008, 321:1834-183 which report detailed methods for estimating which amino acids within a VLR interact with the bound molecule. Estimating 2, 3, 4, 5, 6, 7, 8, 9, 10 or more amino acids in the variable lymphocyte receptor that are closest spatial proximity to the bound molecule and/or provide ionic interactions, and/or hydrogen bond and/or provide Van der Waals force with the molecule of interest providing target amino acids in the variable lymphocyte receptor can be accomplished by a variety of methods. Van der Waals forces refer to attractive or repulsive forces between molecules other than those due to covalent bonds, the hydrogen bonds, or the electrostatic interaction of ions with one another or with neutral molecules or charged molecules. The term includes force between two permanent dipoles (Keesom force), force between a permanent dipole and a corresponding induced dipole (Debye force), force between two instantaneously induced dipoles (London dispersion force). These forces are typically estimated through computer simulations. See Ohue et al., MEGADOCK: An All-to-all Protein-protein Interaction Prediction System Using Tertiary Structure Data, Protein Pept Lett, 2013; Matsuzaki et al., MEGADOCK 3.0: a high-performance protein-protein interaction prediction software using hybrid parallel computing for petascale supercomputing environments, Source Code Biol Med, 2013, 8(1):18; Tuncbag et al., Predicting protein-protein interactions on a proteome scale by matching evolutionary and structural similarities at interfaces using PRISM. Nat Protoc, 2011, 6(9):1341-54. Wang et al., Protein recognition and selection through conformational and mutually induced fit, Proc Natl Acad Sci USA, 2013, 110(51):20545-50; Solernou & Fernandez-Recio, pyDockCG: new coarse-grained potential for protein-protein docking, J Phys Chem B, 2011, 115(19):6032-9; Antes, DynaDock: A new molecular dynamics-based algorithm for protein-peptide docking including receptor flexibility, Proteins, 2010, 78(5):1084-104; Cerqueira et al., MADAMM: a multistaged docking with an automated molecular modeling protocol, Proteins, 2009, 74(1):192-206; Claussen et al., FlexE: efficient molecular docking considering protein structure variations. J Mol Biol, 2001, 308(2):377-95.

In other embodiments, one utilizes a combination of computer simulations and X-ray crystallography, NMR spectroscopy or cryo-electron microscopy experiments. Typically the structures of variable lymphocyte receptor and binding molecule of interest form a crystallized complex. In the event that the complex flails to crystallize one can try other methods. In some instances, two dimensional NMR techniques, optionally in combination with computational methods, can be used to estimate molecular interactions and spatial relationships. See Nishida & Shimada, An NMR method to study protein-protein interactions, Methods Mol Biol, 2012, 757:129-37 and O'Connell et al., The structural analysis of protein-protein interactions by NMR spectroscopy, Proteomics, 2009, 9(23):5224-32.

Providing a known human amino acid sequence with greater than 20, 25, 30, 35, or 40% or more sequence identity to the variable lymphocyte receptor (VLR) amino acid sequence can be done using publicly available databases such as BLAST. In certain embodiments, a comparison window of sequence identity or similarity is made over a 100, 150, 200, or 250 amino acids.

Substituting the target amino acids in the variable lymphocyte receptor within the known human amino acid sequence that correlate in position, if different, in the known human amino acid sequence is typically accomplished by making a sequence alignment followed by the substitutions. In addition to the target amino acids amino acids, one, both, or more of the amino acids on the N- or C-sides of the target amino acid may also be substituted, if different. In some embodiment, one substitutes at least one amino acid next to each of the target amino acids in the variable lymphocyte receptor within the known human amino acid sequence that correlate in position with human amino acid sequence. In certain embodiments, two on the N-side and one on the C-side, two on the C-side and one on the N-side, or two on the N-side and two on the C-side of each target amino acids are substituted.

In certain embodiments, the disclosure relates to isolated modified human amino acid sequences that specifically binds an molecule comprising, providing an amino acid sequence of a variable lymphocyte receptors (VLR) of a jawless vertebrate that binds a molecule; determining, selecting or estimating 2, 3, 4, 5, 6, 7, 8, 9, 10 or more amino acids in the variable lymphocyte receptor that hydrogen bond with the molecule and/or have ionic interacts with and/or are in closest spatial proximity to the bound molecule providing target amino acids in the variable lymphocyte receptor; providing a known human amino acid sequence with greater than 20, 25, 30, or 40% or more sequence identity to the variable lymphocyte receptor (VLR) amino acid sequence; substituting the target amino acids in the variable lymphocyte receptor within the known human amino acid sequence that correlate in position if different in the known human amino acid sequence; substituting at least one amino acid next to each of the target amino acids in the variable lymphocyte receptor with the known human amino acid sequence that correlate in position under conditions to provide a modified human amino acid sequence and the modified human amino acid sequence, when produced provides a polypeptide that specifically binds the molecule; and producing a polypeptide that specifically binds the molecule by expressing the modified human amino acid sequence from a recombinant nucleic acid.

In certain embodiments, the molecule comprises a polypeptide sequence or polysaccharide.

In certain embodiments, the jawless vertebrate is a lamprey or hagfish. In certain embodiments, the variable lymphocyte receptor is a lamprey variable lymphocyte receptor B (VLRB).

In certain embodiments, the 2, 3, 4, 5, 6, 7, 8, 9, 10 or more amino acids in the variable lymphocyte receptor that hydrogen bond with the molecule and/or are in closest spatial proximity to the molecule are selected from within variable amino acid positions of β-strands and a C-terminal variable loop of the concave surface of the crescent-shaped VLR.

In certain embodiments, the molecule is a viral or microbial associated molecule.

In certain embodiments, the viral or microbial associated molecule is *Bacillus anthracis*, Influenza, or HIV-1 antigen.

In certain embodiments, the molecule is a molecule associated with specific normal or malignant human cell. In certain embodiments, the normal or malignant human cell is a blood group O erythrocytes, B cell leukemia cell, B lymphoma cell line. In certain embodiments, the known human amino acid sequence is human leucine-rich repeat receptor. In certain embodiments, the known human amino acid sequence is Slit-family protein (Slit 1, 2, and 3), CD42b, or Nogo-66.

In certain embodiments, the disclosure relates to recombinant vectors comprising nucleic acids that encode the isolated modified human amino acid sequences made by processes disclosed herein.

In certain embodiments, the disclosure relates to expression system comprising recombinant vectors comprising nucleic acids that encode the isolated modified human amino acid sequences made by processes disclosed herein.

In certain embodiments, the disclosure relates to methods of producing a specific binding agent to an molecule comprising, administering an molecule to a jawless vertebrate under conditions such that a cell containing a variable lymphocyte receptor (VLR) binds the molecule and plasmacytes of the jawless vertebrate produce an variable lymphocyte receptor (VLR) that binds the molecule; providing an amino acid sequence of the variable lymphocyte receptors (VLR) that binds the molecule; estimating 2, 3, 4, 5, 6, 7, 8, 9, 10 or more amino acids in the variable lymphocyte receptor that are in closest spatial proximity to the molecule and/or hydrogen bond with the molecule providing target amino acids in the variable lymphocyte receptor; providing a known human amino acid sequence with greater than 20, 25, 30, 35, or 40% or more sequence identity to the variable lymphocyte receptor (VLR) amino acid sequence; aligning the VLR sequence and the known human amino acid sequence; substituting the target amino acids in the variable lymphocyte receptor within the known human amino acid sequence that correlate in position if different in the known human amino acid sequence; substituting at least one amino acid next to each of the target amino acids in the variable lymphocyte receptor with amino acid in the known human amino acid sequence that correlate in position under conditions such that a modified human amino acid sequence is configured to specifically bind the molecule; and producing a specific binding agent by expressing the modified human amino acid sequence from a recombinant nucleic acid.

Variable lymphocyte receptors typically contain an N-terminal LRR sequence, a C-terminal LRR sequence, and multiple interior LRR modules of approximately 12-25 amino acids. The C-terminal LRR sequence typically contains a variable loop (highly variable insert). Within the interior LRR modules, seven amino acids typically contain one or two leucine or isoleucine, if two, separated by a single amino acid, e.g., (SEQ ID NO: 21) XXLXLXX, that are typically located on the concave surface, wherein X may be any amino acid and L may be leucine or isoleucine. In some instants, one L (leucine or isoleucine) may be substituted with any amino acid. In certain embodiments, the target amino acids for grafting into human sequences are 2, 3, 4, 5, 6, or 7 amino acids are within the associated seven residues for at least 1, 2, 3, or all of the LRR modules and optionally all or a portion of the amino acids in the C-terminal highly variable insert. In certain embodiments, the variable lymphocyte receptor has a sequence VXCXXXXLXSVPAXIPTTT XXLXXXXNX-ITKXXPGVFDXLXXLXXXXLXXNXLXXXPXGXFD (SEQ ID NO: 25) wherein X may be any amino acid.

In certain embodiments, the disclosure relates to a composition comprising a polypeptide comprising SEQ ID NO: 1 or 10 or variant thereof with greater than 83, 85, 90, 95, 97, 98, or 99% sequence identity or greater than 85, 90, 95, 97, 98, or 99% sequence similarity. In certain embodiments, the variant comprises one, two, three, four, five, six, seven, eight, nine, or ten amino acid substitutions. In certain embodiments, the amino acid substitutions are conserved substitutions.

In certain embodiments, the variant comprises amino acid substitutions that are not within SEQ ID NO: 3 (IIYLHD), SEQ ID NO: 4 (EIYLGS), SEQ ID NO: 5 (VLDLGT), SEQ ID NO: 6 (ELFLCC), SEQ ID NO: 7 (HLALDQ), SEQ ID NO: 8 (HMYLFG), SEQ ID NO: 9 (IAMRWDGKAVNDPDS).

In certain embodiments, the variant comprises two, three, four, five, or six of the following sequences SEQ ID NO: 3 (IIYLHD), SEQ ID NO: 4 (EIYLGS), SEQ ID NO: 5 (VLDLGT), SEQ ID NO: 6 (ELFLCC), SEQ ID NO: 7 (HLALDQ), SEQ ID NO: 8 (HMYLFG), SEQ ID NO: 9 (IAMRWDGKAVNDPDS).

In certain embodiments, the variant optionally comprises one conserved amino acid substitution within each of the following sequences (IIYLHD), SEQ ID NO: 3

(EIYLGS), SEQ ID NO: 4

(VLDLGT), SEQ ID NO: 5

(ELFLCC), SEQ ID NO: 6

(HLALDQ), SEQ ID NO: 7

(HMYLFG), SEQ ID NO: 8

(IAMRWDGKAVNDPDS). SEQ ID NO: 9

In certain embodiments, the polypeptide comprises SEQ ID NO: 9 (IAMRWDGKAVNDPDS) or variants with one, two, or three amino acid substitutions.

Humanized Slit2-VLRs

In certain embodiments, the disclosure contemplates isolated recombinant polypeptides comprising (SEQ ID NO: 10) or variants thereof,

CPAACTCSNNXXXCXXKGLTEIPTNLPETITXIXXXXNTIKVIPPGAFSP

YKKLRXIXXXXNQISELAPDAFQGLRSLNXLXLXXNKITELPKSLFEGLF

SLQXLXLXXNKINCLRVDAFQDLHNLNXLXLXXNKLQTIAKGTFSPLRAI

QXMXLXXNPFICDCHLKWLADYLH[X]nARCTSPRRLANKRIGQIKSKKF

RC wherein X at each position is individually and independently any amino acid and n is between 5 and 20 or n is between 10 and 18, or n is 14, 15, or 16 provided that the polypeptide does not contain at least one, two, three, four, five six or all of the following wild-type Slit2-D2 sequences selected from (SEQ ID NO: 11) IVDCRG, (SEQ ID NO: 12) EIRLEQ, (SEQ ID NO: 13) RIDLSN, (SEQ ID NO: 14) SLVLYG, (SEQ ID NO: 15) LLLLNA, (SEQ ID NO: 16) LLSLYD, and (SEQ ID NO: 17) TMHLAQ. In certain embodiments, the variants contain one, two, or three amino acid substitutions, provided the amino acid substitutions are not X amino acids. In certain embodiments, the substitutions are conserved substitutions.

In certain embodiments, the disclosure contemplates isolated recombinant polypeptides comprising (SEQ ID NO: 26) or variants thereof,

CPAACTCSNNXXXCXXKGLTEIPTNLPETITXIXXXXNTIKVIPPGAFSP

YKKLRXIXXXXNQISELAPDAFQGLRSLNXLXLXXNKITELPKSLFEGLF

SLQXLXLXXNKINCLRVDAFQDLHNLNXLXLXXNKLQTIAKGTFSPLRAI

QXMXLXXNPFICDCHLKWLADYL[X]nRCTSPRRLANKRIGQIKSKKFRC wherein X at each position is individually and independently any amino acid and n is between 5 and 20 or n is between 10 and 18, or n is 14, 15, or 16 optionally provided that the polypeptide does not contain at least one, two, three, four, five, six or all of the following wild-type Slit2-D2 sequences selected from (SEQ ID NO: 11) IVDCRG, (SEQ ID NO: 12) EIRLEQ, (SEQ ID NO: 13) RIDLSN, (SEQ ID NO: 14) SLVLYG, (SEQ ID NO: 15) LLLLNA, (SEQ ID NO: 16) LLSLYD, and (SEQ ID NO: 17) TMHLAQ.

In certain embodiments, for any of the sequences disclosed herein [X]n is [X]$_m$-[Loop Sequence of VLR or MM3] or [X]$_m$-[Loop Sequence of VLR or MM3]A wherein [X]$_m$ is optionally $X^1$, $X^1X^2$, $X^1X^2X^3$, $X^1X^2X^3X^4$ (SEQ ID NO: 83) wherein $X^1$ is H, $X^2$ is T, $X^3$ is N, and $X^4$ is P. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 27) or variants thereof,

CPAACTCSNNIVDCRGKGLTEIPTNLPETITXIXXXXNTIKVIPPGAFSP

YKKLRXIXXXXNQISELAPDAFQGLRSLNXLXLXXNKITELPKSLFEGLF

SLQXLXLXXNKINCLRVDAFQDLHNLNXLXLXXNKLQTIAKGTFSPLRAI

QXMXLXXNPFICDCHLKWLADYL[X]nRCTSPRRLAN wherein X at each position is individually and independently any amino acid and n is between 5 and 20 or n is between 10 and 18, or n is 14, 15, or 16 optionally provided that the polypeptide does not contain at least one, two, three, four, five, or all of the following wild-type Slit2-D2 sequences selected from (SEQ ID NO: 12) EIRLEQ, (SEQ ID NO: 13) RIDLSN, (SEQ ID NO: 14) SLVLYG, (SEQ ID NO: 15) LLLLNA, (SEQ ID NO: 16) LLSLYD, and (SEQ ID NO: 17) TMHLAQ. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 28) or variants thereof,

CPAACTCSNNIVDCRGKGLTEIPTNLPETITEIRLEQNTIKVIPPGAFSP

YKKLRXIXXXXNQISELAPDAFQGLRSLNXLXLXXNKITELPKSLFEGLF

SLQXLXLXXNKINCLRVDAFQDLHNLNXLXLXXNKLQTIAKGTFSPLRAI

QXMXLXXNPFICDCHLKWLADYL[X]nRCTSPRRLAN wherein X at each position is individually and independently any amino acid and n is between 5 and 20 or n is between 10 and 18, or n is 14, 15, or 16 optionally provided that the polypeptide does not contain at least one, two, three, four, or all of the following wild-type Slit2-D2 sequences selected from (SEQ ID NO: 13) RIDLSN, (SEQ ID NO: 14) SLVLYG, (SEQ ID NO: 15) LLLLNA, (SEQ ID NO: 16) LLSLYD, and (SEQ ID NO: 17) TMHLAQ. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 29) or variants thereof,

CPAACTCSNNIVDCRGKGLTEIPTNLPETITEIRLEQNTIKVIPPGAFSP

YKKLRRIDLSNNQISELAPDAFQGLRSLN<u>XLXLXX</u>NKITELPKSLFEGLF

SLQ<u>XLXLXX</u>NKINCLRVDAFQDLHNLN<u>XLXLXX</u>NKLQTIAKGTFSPLRAI

Q<u>XMXLXX</u>NPFICDCHLKWLADYL<u>[X]n</u>RCTSPRRLAN wherein X at each position is individually and independently any amino acid and n is between 5 and 20 or n is between 10 and 18, or n is 14, 15, or 16 optionally provided that the polypeptide does not contain at least one, two, three, four, or all of the following wild-type Slit2-D2 sequences selected from (SEQ ID NO: 14) SLVLYG, (SEQ ID NO: 15) LLLLNA, (SEQ ID NO: 16) LLSLYD, and (SEQ ID NO: 17) TMHLAQ. In certain embodiments, the variants contain one, two, or three amino acid substitutions, deletions or insertions, provided the amino acid substitutions, deletions or insertions, are not X amino acids. In certain embodiments, the substitutions are conserved substitutions In certain embodiments, the disclosure contemplates isolated recombinant polypeptides comprising (SEQ ID NO: 30) or variants thereof,

CPAACTCSNNIVDCRGKGLTEIPTNLPETITEIRLEQNTIKVIPPGAFSP

YKKLRRIDLSNNQISELAPDAFQGLRSLNSL<u>XLX</u>GNKITELPKSLFEGLF

SLQ<u>XLXLXX</u>NKINCLRVDAFQDLHNLN<u>XLXLXX</u>NKLQTIAKGTFSPLRAI

Q<u>XMXLXX</u>NPFICDCHLKWLADYL<u>[X]n</u>RCTSPRRLAN wherein X at each position is individually and independently any amino acid and n is between 5 and 20 or n is between 10 and 18, or n is 14, 15, or 16 optionally provided that the polypeptide does not contain at least one, two, three, four, or all of the following wild-type Slit2-D2 sequences selected from (SEQ ID NO: 14) SLVLYG, (SEQ ID NO: 15) LLLLNA, (SEQ ID NO: 16) LLSLYD, and (SEQ ID NO: 17) TMHLAQ. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 31) or variants thereof,

CPAACTCSNNIVDCRGKGLTEIPTNLPETITEIRLEQNTIKVIPPGAFSP

YKKLRRIDLSNNQISELAPDAFQGLRSLNSLVLYGNKITELPKSLFEGLF

SLQ<u>XLXLXX</u>NKINCLRVDAFQDLHNLN<u>XLXLXX</u>NKLQTIAKGTFSPLRAI

Q<u>XMXLXX</u>NPFICDCHLKWLADYL<u>[X]n</u>RCTSPRRLAN wherein X at each position is individually and independently any amino acid and n is between 5 and 20 or n is between 10 and 18, or n is 14, 15, or 16 optionally provided that the polypeptide does not contain at least one, two, three, four, or all of the following wild-type Slit2-D2 sequences selected from (SEQ ID NO: 15) LLLLNA, (SEQ ID NO: 16) LLSLYD, and (SEQ ID NO: 17) TMHLAQ. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 32) or variants thereof,

CPAACTCSNNIVDCRGKGLTEIPTNLPETITEIRLEQNTIKVIPPGAFSP

YKKLRRIDLSNNQISELAPDAFQGLRSLNSLVLYGNKITELPKSLFEGLF

SLQLLLLNANKINCLRVDAFQDLHNLN<u>XLXLXX</u>NKLQTIAKGTFSPLRAI

Q<u>XMXLXX</u>NPFICDCHLKWLADYL<u>[X]n</u>RCTSPRRLAN wherein X at each position is individually and independently any amino acid and n is between 5 and 20 or n is between 10 and 18, or n is 14, 15, or 16 optionally provided that the polypeptide does not contain at least one, two, three, four, or all of the following wild-type Slit2-D2 sequences selected from (SEQ ID NO: 16) LLSLYD, and (SEQ ID NO: 17) TMHLAQ. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 33) or variants thereof, GLTEIPTNLPETIT<u>XIXXXX</u>NTIKVIPPGAFSPYKKLR<u>XIXXXX</u>NQISEL APDAFQGLRSLN<u>XLXLXX</u>NKITELPKSLFEGLFSLQ<u>XLXLXX</u>NKINCLRV DAFQDLHNLN<u>XLXLXX</u>NKLQTIAKGTFSPLRAIQ<u>XMXLXX</u>NPFICDCHLK WLADYL<u>[X]n</u>ARCTSPRRLAN wherein X at each position is individually and independently any amino acid and n is between 5 and 20 or n is between 10 and 18, or n is 14, 15, or 16 optionally provided that the polypeptide does not contain at least one, two, three, four, five, or all of the following wild-type Slit2-D2 sequences selected from (SEQ ID NO: 12) EIRLEQ, (SEQ ID NO: 13) RIDLSN, (SEQ ID NO: 14) SLVLYG, (SEQ ID NO: 15) LLLLNA, (SEQ ID NO: 16) LLSLYD, and (SEQ ID NO: 17) TMHLAQ. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 34) or variants thereof, AFSPYKKLR<u>XIXXXX</u>NQISELAPDAFQGLRSLN<u>XLXLXX</u>NKITELPKSLF
EGLFSLQ<u>XLXLXX</u>NKINCLRVDAFQDLHNLN<u>XLXLXX</u>NKLQTIAKGTFSP
LRAIQ<u>XMXLXX</u>NPFICDCHLKWLADYL<u>[X]n</u>RCTSPRRLAN wherein X at each position is individually and independently any amino acid and n is between 5 and 20 or n is between 10 and 18, or n is 14, 15, or 16 optionally provided that the polypeptide does not contain at least one, two, three, four, or all of the following wild-type Slit2-D2 sequences selected from (SEQ ID NO: 13) RIDLSN, (SEQ ID NO: 14) SLVLYG, (SEQ ID NO: 15) LLLLNA, (SEQ ID NO: 16) LLSLYD, and (SEQ ID NO: 17) TMHLAQ. In certain embodiments, the variants contain one, two, or three amino acid substitutions, deletions or insertions, provided the amino acid substitutions, deletions or insertions, are not X amino acids.

In certain embodiments, the substitutions are conserved substitutions.

In certain embodiments, the disclosure contemplates isolated recombinant polypeptides comprising (SEQ ID NO: 35) or variants thereof, AFQGLRSLNXLXLXXNKITELPKSLFEGLFSLQXLXLXXNKINCLRVDAF
QDLHNLNXLXLXXNKLQTIAKGTFSPLRAIQXMXLXXNPFICDCHLKWLA
DYL[X]nRCTSPRRLAN wherein X at each position is individually and independently any amino acid and n is between 5 and 20 or n is between 10 and 18, or n is 14, 15, or 16 optionally provided that the polypeptide does not contain at least one, two, three, four, or all of the following wild-type Slit2-D2 sequences selected from (SEQ ID NO: 14) SLVLYG, (SEQ ID NO: 15) LLLLNA, (SEQ ID NO: 16) LLSLYD, and (SEQ ID NO: 17) TMHLAQ. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 36) or variants thereof,

XLXGNKITELPKSLFEGLFSLQXLXLXXNKINCLRVDAFQDLHNLNXLXL
XXNKLQTIAKGTFSPLRAIQXMXLXX wherein X at each position is individually and independently any amino acid and n is between 5 and 20 or n is between 10 and 18, or n is 14, 15, or 16 optionally provided that the polypeptide does not contain at least one, two, three, or all of the following wild-type Slit2-D2 sequences selected from (SEQ ID NO: 14) SLVLYG, (SEQ ID NO: 15) LLLLNA, (SEQ ID NO: 16) LLSLYD, and (SEQ ID NO: 17) TMHLAQ. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 37) or variants thereof,

XLXLXXNKINCLRVDAFQDLHNLNXLXLXXNKLQTIAKGTFSPLRAIQXM
XLXX wherein X at each position is individually and independently any amino acid and n is between 5 and 20 or n is between 10 and 18, or n is 14, 15, or 16 optionally provided that the polypeptide does not contain at least one, two, or all of the following wild-type Slit2-D2 sequences selected from (SEQ ID NO: 15) LLLLNA, (SEQ ID NO: 16) LLSLYD, and (SEQ ID NO: 17) TMHLAQ. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 38) or variants thereof,

XLXLXXNKLQTIAKGTFSPLRAIQXMXLXX wherein X at each position is individually and independently any amino acid and n is between 5 and 20 or n is between 10 and 18, or n is 14, 15, or 16 optionally provided that the polypeptide does not contain at least one or all of the following wild-type Slit2-D2 sequences selected from (SEQ ID NO: 16) LLSLYD, and (SEQ ID NO: 17) TMHLAQ. In certain embodiments, the variants contain one, two, or three amino acid substitutions, deletions or insertions, provided the amino acid substitutions, deletions or insertions, are not X amino acids.

In certain embodiments, the disclosure contemplates isolated recombinant polypeptides comprising (SEQ ID NO: 23) or variants thereof,

XLXLXXNKLQTIAKGTFSPLRAIQXMXLXXNPFICDCHLKWLADYLH wherein X at each position is individually and independently any amino acid provided that the polypeptide does not contain at least one of the following wild-type Slit2-D2 sequences selected from (SEQ ID NO: 16) LLSLYD, and (SEQ ID NO: 17) TMHLAQ. In certain embodiments, the variants contain one, two, or three amino acid substitutions, provided the amino acid substitutions are not X amino acids. In certain embodiments, the substitutions are conserved substitutions.

In certain embodiments, the disclosure contemplates isolated recombinant polypeptides comprising (SEQ ID NO: 65) or variants thereof,

XLXLXXNKINCLRVDAFQDLHNLNXLXLXXNKLQTIAKGTFSPLRAIQXM
XLXXNPFICDCHLKWLADYLH wherein X at each position is individually and independently any amino acid provided that the polypeptide does not contain at least one, two or all of the following wild-type Slit2-D2 sequences selected from (SEQ ID NO: 15) LLLLNA, (SEQ ID NO: 16) LLSLYD, and (SEQ ID NO: 17) TMHLAQ. In certain embodiments, the variants contain one, two, or three amino acid substitutions, provided the amino acid substitutions are not X amino acids. In certain embodiments, the substitutions are conserved substitutions.

Humanized Slit2-MM3 Sequences

In certain embodiments, the disclosure contemplates isolated recombinant polypeptides comprising (SEQ ID NO: 39) or variants thereof, CPAACTCSNNXXXCXXKGLTEIPTNLPETITXIXXXXNTIKVIPPGAFSP
YKKLRXIXXXXNQISELAPDAFQGLRSLNXLXLXXNKITELPKSLFEGLF
SLQXLXLXXNKINCLRVDAFQDLHNLNYLDLNNNKLQTIAKGTFSPLRAI
QHMWLYXNPFICDCHLKWLADYL[X]nRCTSPRRLANKRIGQIKSKKFRC wherein X at each position is individually and independently any amino acid and n is between 5 and 20 or n is between 10 and 18, or n is 14, 15, or 16. In certain embodiments, for any of the sequences disclosed herein [X]n is [X]$_m$-[Loop Sequence of VLR or MM3] or [X]$_m$-[Loop Sequence of VLR or MM3]A wherein [X]$_m$ is optionally X¹, X¹X², X¹X²X³, X¹X²X³X⁴ (SEQ ID NO: 83) wherein X¹ is H, X² is T, X³ is N, and X⁴ is P.

In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 40) or variants thereof,

CPAACTCSNNIVDCRGKGLTEIPTNLPETITXIXXXXNTIKVIPPGAFSP

YKKLRXIXXXXNQISELAPDAFQGLRSLNXLXLXXNKITELPKSLFEGLF

SLQXLXLXXNKINCLRVDAFQDLHNLNYLDLNNNKLQTIAKGTFSPLRAI

QHMWLYXNPFICDCHLKWLADYL[X]nRCTSPRRLAN wherein X at each position is individually and independently any amino acid and n is between 5 and 20 or n is between 10 and 18, or n is 14, 15, or 16. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 41) or variants thereof,

CPAACTCSNNIVDCRGKGLTEIPTNLPETITEIRLEQNTIKVIPPGAFSP

YKKLRXIXXXXNQISELAPDAFQGLRSLNXLXLXXNKITELPKSLFEGLF

SLQXLXLXXNKINCLRVDAFQDLHNLNYLDLNNNKLQTIAKGTFSPLRAI

QHMWLYXNPFICDCHLKWLADYL[X]nRCTSPRRLAN wherein X at each position is individually and independently any amino acid and n is between 5 and 20 or n is between 10 and 18, or n is 14, 15, or 16. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 42) or variants thereof,

CPAACTCSNNIVDCRGKGLTEIPTNLPETITEIRLEQNTIKVIPPGAFSP

YKKLRRIDLSNNQISELAPDAFQGLRSLNXLXLXXNKITELPKSLFEGLF

SLQXLXLXXNKINCLRVDAFQDLHNLNYLDLNNNKLQTIAKGTFSPLRAI

QHMWLYXNPFICDCHLKWLADYL[X]nRCTSPRRLAN wherein X at each position is individually and independently any amino acid and n is between 5 and 20 or n is between 10 and 18, or n is 14, 15, or 16. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 43) or variants thereof,

CPAACTCSNNIVDCRGKGLTEIPTNLPETITEIRLEQNTIKVIPPGAFSP

YKKLRRIDLSNNQISELAPDAFQGLRSLNSLXLXGNKITELPKSLFEGLF

SLQXLXLXXNKINCLRVDAFQDLHNLNYLDLNNNKLQTIAKGTFSPLRAI

QHMWLYXNPFICDCHLKWLADYL[X]nRCTSPRRLAN wherein X at each position is individually and independently any amino acid and n is between 5 and 20 or n is between 10 and 18, or n is 14, 15, or 16. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 44) or variants thereof,

CPAACTCSNNIVDCRGKGLTEIPTNLPETITEIRLEQNTIKVIPPGAFSP

YKKLRRIDLSNNQISELAPDAFQGLRSLNSLVLYGNKITELPKSLFEGLF

SLQXLXLXXNKINCLRVDAFQDLHNLNYLDLNNNKLQTIAKGTFSPLRAI

QHMWLYXNPFICDCHLKWLADYL[X]nRCTSPRRLAN wherein X at each position is individually and independently any amino acid and n is between 5 and 20 or n is between 10 and 18, or n is 14, 15, or 16. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 45) or variants thereof,

CPAACTCSNNIVDCRGKGLTEIPTNLPETITEIRLEQNTIKVIPPGAFSP

YKKLRRIDLSNNQISELAPDAFQGLRSLNSLVLYGNKITELPKSLFEGLF

SLQLLLLNANKINCLRVDAFQDLHNLNYLDLNNNKLQTIAKGTFSPLRAI

QHMWLYXNPFICDCHLKWLADYL[X]nRCTSPRRLAN wherein X at each position is individually and independently any amino acid and n is between 5 and 20 or n is between 10 and 18, or n is 14, 15, or 16. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 46) or variants thereof,

GLTEIPTNLPETITXIXXXXNTIKVIPPGAFSPYKKLRXIXXXXNQISEL

APDAFQGLRSLNXLXLXXVNKITELPKSLFEGLFSLQXLXLXXNKINCL

```
RVDAFQDLHNLNYLDLNNNKLQTIAKGTFSPLRAIQHMWLYXNPFICDC

HLKWLADYL[X]nRCTSPRRLAN
``` wherein X at each position is individually and independently any amino acid and n is between 5 and 20 or n is between 10 and 18, or n is 14, 15, or 16. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 47) or variants thereof,

```
AFSPYKKLRXIXXXXNQISELAPDAFQGLRSLNXLXLXXNKITELPKSLF

EGLFSLQXLXLXXNKINCLRVDAFQDLHNLNYLDLNNNKLQTIAKGTFSP

LRAIQHMWLYXNPFICDCHLKWLADYL[X]nRCTSPRRLAN
``` wherein X at each position is individually and independently any amino acid and n is between 5 and 20 or n is between 10 and 18, or n is 14, 15, or 16. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 48) or variants thereof,

```
AFQGLRSLNXLXLXXNKITELPKSLFEGLFSLQXLXLXXNKINCLRVDAF

QDLHNLNYLDLNNNKLQTIAKGTFSPLRAIQHMWLYXNPFICDCHLKWLA

DYL[X]nRCTSPRRLAN
``` wherein X at each position is individually and independently any amino acid and n is between 5 and 20 or n is between 10 and 18, or n is 14, 15, or 16. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates isolated recombinant polypeptides comprising (SEQ ID NO: 49) or variants thereof,

```
LXLXGNKITELPKSLFEGLFSLQXLXLXXNKINCLRVDAFQDLHNLNYLD

LNNNKLQTIAKGTFSPLRAIQHMWLYXNPFICDCHLKWLADYL
``` wherein X at each position is individually and independently any amino acid. In certain embodiments, the variants contain one, two, or three amino acid substitutions, deletions or insertions, provided the amino acid substitutions, deletions or insertions, are not X amino acids.

In certain embodiments, the substitutions are conserved substitutions.

In certain embodiments, the disclosure contemplates isolated recombinant polypeptides comprising (SEQ ID NO: 50) or variants thereof,

```
LQXLXLXXNKINCLRVDAFQDLHNLNYLDLNNNKLQTIAKGTFSPLRAIQH

MWLYXNPFICDCHLKWLADYL
``` wherein X at each position is individually and independently any amino acid. In certain embodiments, the variants contain one, two, or three amino acid substitutions, deletions or insertions, provided the amino acid substitutions, deletions or insertions, are not X amino acids.

In certain embodiments, the substitutions are conserved substitutions.

In certain embodiments, the disclosure contemplates isolated recombinant polypeptides comprising (SEQ ID NO: 51) or variants thereof,

```
AFQDLHNLNYLDLNNNKLQTIAKGTFSPLRAIQEMWLYXNPFICDCHLKWL

ADYL
``` wherein X at each position is individually and independently any amino acid. In certain embodiments, the variants contain one, two, or three amino acid substitutions, deletions or insertions, provided the amino acid substitutions, deletions or insertions, are not X amino acids. In certain embodiments, the substitutions are conserved substitutions.

In certain embodiments, the disclosure contemplates fusions or Slit2-MM3 polypeptides comprising (SEQ ID NO: 58-63) or variants thereof,

```
                                        (SEQ ID NO: 58)
CPAACTCSNNIVDCRGKGLTEIPTNLPETITEIRLEQNTIKVIPPGAFSPY

KKLRRIDLSNNQISELAPDAFQGLRSLNSLVLYGNKITELPKSLFEGLFSL

QLLYLNANKINCLRVDAFQDLHNLNYLDLNNNKLQTIAKGTFSPLRAIQHI

WLYQNPFICDCHLKWLADYLHASIVNPHPYGGVDNARCTSPRRLAN (SEQ ID NO: 59)
CPAACTCSNNIVDCRGKGLTEIPTNLPETITEIRLEQNTIKVIPPGAFSPY

KKLRRIDLSNNQISELAPDAFQGLRSLNSLVLYGNKITELPKSLFEGLFSL

QLLYLNANKINCLRVDAFQDLHNLNYLDLNNNKLQTIAKGTFSPLRAIQHI

WLYQNPFICDCHLKWLADYLSIVNPHPYGGVDARCTSPRRLAN (SEQ ID NO: 60)
CPAACTCSNNIVDCRGKGLTEIPTNLPETITEIRLEQNTIKVIPPGAFSPY

KKLRRIDLSNNQISELAPDAFQGLRSLNSLVLYGNKITELPKSLFEGLFSL

QLLYLNANKINCLRVDAFQDLHNLNYLDLNNNKLQTIAKGTFSPLRAIQHI

WLYQNPFICDCHLKWLADYLIVQHASIVNPHPYGGVDARCTSPRRLAN (SEQ ID NO: 61)
CPAACTCSNNIVDCRGKGLTEIPTNLPETITEIRLEQNTIKVIPPGAFSPY

KKLRRIDLSNNQISELAPDAFQGLRSLNSLVLYGNKITELPKSLFEGLFSL

QLLLLNANKINCLRVDAFQDLHNLNYLDLNNNKLQTIAKGTFSPLRAIQHI

WLYQNPFICDCHLKWLADYLHASIVNPHPYGGVDNARCTSPRRLAN (SEQ ID NO: 62)
CPAACTCSNNIVDCRGKGLTEIPTNLPETITEIRLEQNTIKVIPPGAFSPY

KKLRRIDLSNNQISELAPDAFQGLRSLNSLVLYGNKITELPKSLFEGLFSL

QLLLLNANKINCLRVDAFQDLHNLNYLDLNNNKLQTIAKGTFSPLRAIQHI

WLYQNPFICDCHLKWLADYLSIVNPHPYGGVDARCTSPRRLAN
```

(SEQ ID NO: 63)
CPAACTCSNNIVDCRGKGLTEIPTNLPETITEIRLEQNTIKVIPPGAFSPY

KKLRRIDLSNNQISELAPDAFQGLRSLNSLVLYGNKITELPKSLFEGLFSL

QLLLLNANKINCLRVDAFQDLHNLNYLDLNNNKLQTIAKGTFSPLRAIQHI

WLYQNPFICDCHLKWLADYLIVQHASIVNPHPYGGVDARCTSPRRLAN

Modified human sequences from VLR by selection from protein display libraries Humanized specific binding agents may be isolated from combinatorial libraries of variant proteins using protein display technologies, e.g., phage display, yeast surface display, bacterial display, or cell-free systems. See Finlay et al., Methods Mol. Biol., 2011, 681:87-101; Daugherty, Curr. Opin. Struct. Biol., 2007, 17:474-480; Gai & Wittrup, Curr. Opin. Struct. Biol., 2007, 17: 467-473; Zhou et al., MAbs., 2010, 2:508-518; Shen et al., Proc. Nat. Acad. Sci. USA, 2005, 102: 5969-5974. Typically a collection of unique variant proteins are linked through the display platform by expression from corresponding mutated nucleic acids. After exposing/mixing the variant proteins expressed on the display platform with the target molecule, molecule bound variants are identified and/or separated for analysis. Typically, the protein sequence is determined by sequencing an associated nucleic acid in the display platform. For example, in yeast surface display, recombinant yeast cells express variant proteins wherein the yeast cell expresses the variant protein conjugated to a cell wall protein. The yeast cell can contain a plasmid DNA that encodes the variant protein which is expressed on the surface of the yeast cell, and sequencing the plasmid DNA provides the protein sequence of the variant protein. See Gera et al., Protein selection using yeast surface display, Methods, 2013, 60(1):15-26. In phage display, variant proteins are typically conjugated to a bacteriophage coat protein. Cell-based systems also typically rely on the expression of variant proteins conjugated to cell surface proteins, e.g., in bacterial, yeast, and mammalian cells, and the host cell carries a plasmid vector that encodes the variant proteins. Cell-free systems have also been developed wherein the variant protein is conjugated directly to its encoding mRNA, termed ribosome display or mRNA display.

In certain embodiments, the disclosure contemplates methods of producing a humanized specific binding agent comprising one or more of the following steps, a) providing a lamprey antibody sequence that specifically binds a target molecule, b) identifying a library of leucine rich repeat sequences, made by a process comprising, 1) comparing the lamprey antibody sequence to a human leucine rich repeat sequence and identifying overlapping amino acid locations, non-overlapping amino acid locations containing conserved substitutions, and non-overlapping amino acid locations containing non-conserved substitutions over a comparison window;

2) assigning overlapping amino acid locations as amino acids for those respective locations;

3) assigning the amino acids of the human rich repeat sequence to the non-overlapping amino acid locations containing conserved substitutions for those respective locations;

4) assigning a random choice between the amino acids of the human leucine rich repeat sequence or the amino acid sequence of the lamprey to provide a library of variant leucine rich repeat sequences for those respective locations;

c) preparing a display library of variant leucine rich repeat sequences containing the assigned amino acids for respective locations and mixing with the target molecule for binding;

d) identifying one or more of the variant leucine rich repeat sequences that bind the target molecule providing a humanized specific binding agent; and e) expressing the humanized specific binding agent in an expression system comprising a recombinant vector that encodes the humanized specific binding agent.

In certain embodiments, the comparison window is or is as least or is more than 50, 100, 250, 500, or 1000 amino acids in length. In certain embodiments, the comparison window is over one, two, three, four, five, six, seven, or more/all of the following domains LRRNT, LRR1, LRRV1, LRRV2, LRRV3, (LRRVX)$_n$, LRRVe, LRRCP, and LRRCT, wherein X and n refer to an integer, e.g., 0, 1, 2, 3, 4, 5, or 6.

In certain embodiments, the disclosure contemplates multiple humanized specific binding agents are identified and one selects desirable candidates by balancing factors such as maximizing binding affinity and maximizing the number of overlapping human amino acid locations.

In certain embodiments, the amino acids are conserved substitutions if they are among a group with similar properties according to the following amino acid groups: Aromatic—F Y W; hydrophobic—A V I L; Charged positive—R K H; Charged negative—D E; Polar—S T N Q.

In certain embodiments, if there are one or more amino acid deletions in the human leucine rich sequence, then one assigns the amino acid of the lamprey for those respective locations.

In certain embodiments, the human leucine rich repeat sequence is Slit-D2. For example, a polypeptide library can be assigned amino acids at respective locations for identifying a humanized binding agent wherein the library expresses a LRRNT domain comprising the following sequences CPX$^1$X$^2$CTCSX$^3$NX$^4$VDCRGKX$^5$X$^6$ (SEQ ID NO: 22), wherein X$^1$ to X$^6$ is any amino acid. In certain embodiments, X$^1$ is A or S, X$^2$ is A or Q, X$^3$ is N or G, X$^4$ is I or T, X$^5$ is G or R, X$^6$ is L or H.

In certain embodiments, the human leucine rich repeat sequence comprises one, two, three, four, five, six, seven, or more of the following domains LRRNT, LRR1, LRRV1, LRRV2, LRRV3, LRRV4, LRRV5, LRRV6, LRRV7, LRRV8, LRRV9, LRRVe, LRRCP, and LRRCT.

In certain embodiments, the human leucine rich repeat sequence comprises one, two, three, four, five, six, seven, or all of the following domains LRRNT, LRR1, LRRV1, LRRV2, LRRV3, LRRVe, LRRCP, and LRRCT.

In certain embodiments, the human leucine rich repeat sequence comprises one, two, three, four, five, or all of the following domains LRRV1, LRRV2, LRRV3, LRRVe, LRRCP, and LRRCT.

In certain embodiments, the human leucine rich repeat sequence comprises one, two, three, four, or all of the following domains LRRV2, LRRV3, LRRVe, LRRCP, and LRRCT.

In certain embodiments, the human leucine rich repeat sequence comprises one, two, three, or all of the following domains LRRV3, LRRVe, LRRCP, and LRRCT.

In certain embodiments, the human leucine rich repeat sequence comprises one, two, or all of the following domains LRRVe, LRRCP, and LRRCT.

In certain embodiments, the human leucine rich repeat sequence comprises one or both of the following domains LRRCP and LRRCT.

In certain embodiments, the disclosure contemplates that libraries of human leucine rich repeat sequences may contain combinations of domains such as LRRNT, LRR1, LRRV1, LRRV2, LRRV3, LRRVe, LRRCP, and LRRCT which have been substituted with desirable sequences to allow for high levels of expression in peptide library expression systems. For example, Lee et al. Proc Natl Acad Sci USA, 2009, 106(31):12891-6, report the substitution of LRRNT, LRR1, and LRRV1 of Internalin B allows for a high level of expression in bacteria. In certain embodiments, this disclosure contemplates libraries which contain LRRNT, LRR1, and LRRV1 of Internalin B conjugated to domains (LRRVX)$_n$, LRRVe, LRRCP, and LRRCT of a human leucine rich repeat library as produced herein, wherein X and n refer to an integer, e.g., 3, 4, 5, 6, 7, or 8.

Fusion Proteins

In certain embodiments, the disclosure relates to variable lymphocyte receptor optionally modified to include humanized amino acid sequences as disclosed herein conjugated to a human antibody constant region recognized by Fc receptors and complement sufficient for effector functions of a human immune system. In certain embodiments, this disclosure relates to fusion proteins comprising a modified human amino acid sequence disclosed herein and a Fc sequence or fragment thereof that are able to provide effector functions, e.g., elicit antibody-dependent cellular cytotoxicity in vivo or in vitro, and optionally a halve-life comparable to wild type human antibodies. Therapeutics antibodies typically employ intact IgG molecules. IgG1 Fc can interact with Fc gamma receptors that instigate effector functions. Fc contains binding sites for the complement activator C1q. The binding site for neonatal Fc receptor (FcRn) effects half-life.

Naturally produced antibodies contain Fab antigen-binding site arms attached to a Fc region. The IgG Fc region is a homodimer containing a CH3 domain and CH2 domain. The CH2 domains are typically glycosylated through at Asn297. IgG Fc CH2 domains contain interactions sites for FcgammaRI, FcgammaRII, FcgammaRIII and C1q effector ligands that are responsible for effector mechanisms such as antibody-dependent cellular cytotoxicity (ADCC).

In certain embodiments, the disclosure contemplates Fc fusion proteins wherein the Fc sequence is able to elicit antibody-dependent cellular cytotoxicity and contains binding sites for FcgammaRI, FcgammaRII, FcgammaRIII, the complement activator C1q, the neonatal Fc receptor (FcRn), and combinations thereof. In certain embodiments, the disclosure contemplates that that the fusion protein is a single chain fusion of the modified human sequence and a Fc sequence. Powers et al. report single-chain Fv-Fc fusions are capable of mediating antibody-dependent cellular cytotoxicity against tumor target cells using human peripheral blood mononuclear cells as effectors. J Immunol Methods, 2001, 251(1-2):123-35.

In certain embodiments, the disclosure contemplates that that the Fc sequence may contain certain deletions or mutations, e.g., the CH3 domain. Wozniak-Knopp et al., report human IgG1 Fc regions were prepared in which loop sequences at the C-terminal tip of the CH3 domain were randomized. These proteins were able to provide antigen binding, effector functions and an in vivo half-life similar to wild-type antibodies. Protein Engineering, Design and Selection, 2010, 23 (4): 289-297.

In certain embodiments, the disclosure contemplates recombinant vectors comprising the fusion proteins disclosed herein and expression systems comprising the vectors.

In certain embodiments, the disclosure relates to a composition comprising a polypeptide comprising SEQ ID NO: 19, 20, 24 or variants thereof with greater than 83, 85, 90, 95, 97, 98, or 99% sequence identity or greater than 85, 90, 95, 97, 98, or 99% sequence similarity. In certain embodiments, the variant comprises one, two, three, four, five, six, seven, eight, nine, or ten amino acid substitutions. In certain embodiments, the amino acid substitutions are conserved substitutions.

In certain embodiments, the VLRs or modified VLRs or fragments may be fused to a signal-transduction component of the T-cell antigen receptor such as CD3-zeta. In certain embodiments, the signal-transduction component of the T-cell antigen receptor is a peptide with an immunoreceptor tyrosine-based activation motif with the consensus sequence YXXLXXXXXXXYXXL (SEQ ID NO: 52) wherein X is any amino acid L is leucine or isoleucine, wherein SEQ ID NO: 15 optionally has one or two X amino acid deletions within the middle segment XXXXXXXX (SEQ ID NO: 53). The immunoreceptor tyrosine-based activation motif (underlined) is in the partial DD3-zeta sequence (SEQ ID NO: 54)
DPKLCYLLDGILFIYGVILTALFLRVKFSRSADAPAYQQGQNQLYNELNLG

RREEYDVLDKRRGRDPEMGGKPQRRKNPQEGLYNELQKDKMAEAYSEIGMK

GERRRGKGHDGLYQGLSTATKDTYDALHMQ or fragments or variants, e.g. having 1, 2, or 3 amino acid deletion, addition, or substitution variants, or a sequence with greater than 50, 60, 70, 80, 90, 95% or greater identity thereto.

In certain embodiments, the signal-transduction component of the T-cell antigen receptor is a peptide with a immunoreceptor tyrosine-based activation motif (underlined) with the sequence of immunoglobulin epsilon receptor subunit gamma precursor (SEQ ID NO: 55)
EPQLCYILDAILFLYGIVLTLLYCRLKIQVRKAAITSYEKSDGVYTGLSTR

NQETYETLKHE fragments or variants thereof variants or a sequence with greater than 50, 60, 70, 80, 90, 95% or greater identity thereto.

Methods of Use

B cells present antigen to T cells typically stimulating B cells to differentiate into more specialized cells such as immature and mature plasma cells. Plasma cells produce large amounts of antibodies. Multiple myeloma is cancer that forms in plasma cells. B cell malignancies are effectively treated by therapeutic antibodies specific for the CD20 surface antigen, which results in depletion of normal and malignant B cells. Despite success in treating B cell lymphoma and leukemia, anti-CD20 antibodies are not effective in treating multiple myeloma, because CD20 surface expression is lost as mature B cells differentiate into plasma cells. Other plasma cell surface antigens currently under investigation for targeting multiple myeloma plasma cells are also expressed by many other cell types and tissues, which complicates plasma cell targeting because of the potential for unacceptable side effects. Currently, no monoclonal antibody-based therapy is available for patients with multiple myeloma. Treatments with chemotherapy drugs and autologous hematopoietic stem-cell transplantation prolong overall survival but sometimes do not cure the subject. Thus, there is a need to identify improved treatment methods.

In certain embodiments, the disclosure contemplates treating plasma cell malignancies, such as multiple myeloma by administering and effective amount of a fusion protein or polypeptide disclosed herein or fragment thereof to a subject in need thereof. In certain embodiments, the fusion protein comprises a MM3 sequence or humanized MM3 sequence and a signal-transduction component of the T-cell antigen receptor such as a human Fc sequence. In certain embodiments, the fusion protein is administered in combination with lenalidomide and dexamethasone, bortezomib, or combinations thereof. In certain embodiments, the treatment is in combination with autologous or allogeneic stem cell transplantation.

In certain embodiments, the disclosure contemplates treating or preventing cancer comprising administering an effective amount of a VLR based fusion protein comprising a modified human sequence disclosed herein that binds to a tumor associated antigen to a subject in need thereof. The fusion protein may comprise a VLR or modified VLR sequences, or humanized VLR sequence, Slit2-VLR sequence, generated using methods reported herein.

In certain embodiments, the VLR based fusion proteins bind a tumor associates antigen selected from CD20, CD20, CD30, CD33, CD52, EpCAM, epithelial cell adhesion molecule, gpA33, glycoprotein A33, Mucins, TAG-72, tumour-associated glycoprotein 72, Folate-binding protein, VEGF, vascular endothelial growth factor, integrin $\alpha V\beta 3$, integrin $\alpha 5\beta 1$, FAP, fibroblast activation protein, CEA, carcinoembryonic antigen, tenascin, Le$^y$, Lewis Y antigen, CAIX, carbonic anhydrase IX, epidermal growth factor receptor (EGFR; also known as ERBB1), ERBB2 (also known as HER2), ERBB3, MET (also known as HGFR), insulin-like growth factor 1 receptor (IGF1R), ephrin receptor A3 (EPHA3), tumour necrosis factor (TNF)-related apoptosis-inducing ligand receptor 1 (TRAILR1; also known as TNFRSF10A), TRAILR2 (also known as TNFRSF10B) and receptor activator of nuclear factor-xB ligand (RANKL; also known as TNFSF11) and fragments thereof.

In certain embodiments, the subject is at risk of, exhibiting symptoms of, or diagnosed with lymphoma, B cell lymphoma, breast cancer, prostate cancer, colorectal cancer, gastric cancer, lung cancer, skin cancer, bladder cancer, brain cancer, kidney cancer, endometrial cancer, pancreatic cancer, and thyroid cancer.

In certain embodiments, contemplated methods include further administering a second anti-cancer agent such as bevacizumab, gefitinib, erlotinib, temazolamide, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vincristine, vinblastine, vindesine, vinorelbine taxol, taxotere, etoposide, teniposide, amsacrine, topotecan, camptothecin, bortezomib, anegrilide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, combretastatin, thalidomide, and/or lenalidomide or combinations thereof.

In certain embodiments, the disclosure contemplates treating or preventing breast cancer using fusion protein disclosed herein and one more other anti-cancer agents. In certain embodiments, the disclosure contemplates treating or preventing breast cancer using fusion proteins disclosed herein and trastuzumab and/or lapatinib. In certain embodiments, the disclosure contemplates treating or preventing breast cancer using fusion proteins disclosed herein and docetaxel and cyclophosphamide. In certain embodiments, the disclosure contemplates treating or preventing breast cancer using fusion proteins disclosed herein and docetaxel, carboplatin, and trastuzumab. In certain embodiments, the disclosure contemplates treating or preventing breast cancer using fusion proteins disclosed herein and cyclophosphamide, doxorubicin, and 5-fluorouracil (5-FU). In certain embodiments, the disclosure contemplates treating or preventing breast cancer using fusion proteins disclosed herein and docetaxel, doxorubicin, and cyclophosphamide. In certain embodiments, the disclosure contemplates treating or preventing breast cancer using fusion proteins disclosed herein and doxorubicin and cyclophosphamide followed by paclitaxel or docetaxel. In certain embodiments, the disclosure contemplates treating or preventing breast cancer using fusion proteins disclosed herein and 5-FU, epirubicin, and cyclophosphamide followed by docetaxel or paclitaxel.

In certain embodiments, the disclosure contemplates treating or preventing prostate cancer using fusion proteins disclosed herein and one more other anti-cancer agents. In certain embodiments, the disclosure contemplates treating or preventing prostate cancer using fusion proteins disclosed herein and leuprolide, goserelin, or buserelin. In certain embodiments, the disclosure contemplates treating or preventing prostate cancer using fusion proteins disclosed herein and flutamide, bicalutamide, enzalutamide, or nilutamide. In certain embodiments, the disclosure contemplates treating or preventing prostate cancer using fusion proteins disclosed herein and ketoconazole or aminoglutethimide. In certain embodiments, the disclosure contemplates treating or preventing prostate cancer using fusion proteins disclosed herein and abiraterone, bicalutamide, cabazitaxel, bicalutamide, degarelix, denosumab, docetaxel, enzalutamide, cabazitaxel, leuprolide, prednisone, denosumab, sipuleucel-T, or radium 223 dichloride and combinations thereof.

In certain embodiments, the disclosure contemplates treating or preventing colon cancer using fusion proteins disclosed herein and one more other anti-cancer agents. In certain embodiments, the disclosure contemplates treating or preventing colon cancer using fusion proteins disclosed herein and 5-FU, leucovorin, or capecitabine or combinations thereof. In certain embodiments, the disclosure contemplates treating or preventing colon cancer using fusion proteins disclosed herein and capecitabine and oxaliplatin. In certain embodiments, the disclosure contemplates treating or preventing colon cancer using fusion proteins disclosed herein and 5-FU, leucovorin, and oxaliplatin. In certain embodiments, the disclosure contemplates treating or preventing colon cancer using fusion proteins disclosed herein and leucovorin, 5-FU, and irinotecan. In certain embodiments, the disclosure contemplates treating or preventing colon cancer using fusion proteins disclosed herein and leucovorin, 5-FU, oxaliplatin, and irinotecan.

In certain embodiments, the disclosure contemplates treating or preventing colon cancer using fusion proteins disclosed herein and bevacizumab or cetuximab. In certain embodiments, the disclosure contemplates treating or preventing colon cancer using fusion proteins disclosed herein and 5-FU and leucovorin optionally with bevacizumab. In certain embodiments, the disclosure contemplates treating or preventing colon cancer using fusion proteins disclosed herein and capecitabine optionally with bevacizumab. In certain embodiments, the disclosure contemplates treating or preventing colon cancer using fusion proteins disclosed herein and irinotecan optionally with cetuximab. In certain embodiments, the disclosure contemplates treating or preventing colon cancer using fusion proteins disclosed herein and cetuximab. In certain embodiments, the disclosure contemplates treating or preventing colon cancer using fusion proteins disclosed herein and panitumumab. In certain embodiments, the disclosure contemplates treating or preventing colon cancer using fusion proteins disclosed herein and regorafenib.

In certain embodiments, the disclosure contemplates treating or preventing lung cancer using fusion proteins disclosed herein and a chemotherapy agent is selected from vinorelbine, etoposide, mitomycin C, gemcitabine, irinotecan, pemetrexed, gefitinib, erlotinib, lapatinib, crizotinib, and a *vinca* alkaloid or combinations thereof. In certain embodiments, the *vinca* alkaloid is vinblastine, vincristine, vindesine, or vinorelbine. In certain embodiments, the disclosure contemplates treating or preventing lung cancer using fusion proteins disclosed herein and chemotherapy agent is bevacizumab panitumumab, zalutumumab, nimotuzumab, matuzumab, or cetuximab. In certain embodiments, the disclosure contemplates treating or preventing lung cancer using fusion proteins disclosed herein and a platinum based agent and/or a taxane e.g., paclitaxel and docetaxel or combinations thereof.

In certain embodiments, the disclosure contemplates treating or preventing brain cancer, glioblastoma multiforme, oligodendroglioma, primitive neuroectodermal tumours, ependymomas, or glioma. In certain embodiments, the fusion protein is optionally administered in combination with temozolomide, procarbazine, carmustine (BCNU), lomustine (CCNU), vincristine, and combinations thereof. In certain embodiments, procarbazine, lomustine (CCNU) and vincristine are combined. In certain embodiments, the fusion protein is optionally administered in combination with irinotecan, cis-platin, carboplatin, methotrexate, etoposide, bleomycin, vinblastine, actinomycin (Dactinomycin), cyclophosphamide, or ifosfamide.

In certain embodiments, the disclosure contemplates administering combinations of fusion proteins disclosed herein with temozolomide. Treatment of glioblastoma includes chemotherapy during and after radiotherapy. On average, chemotherapy after surgery and radiotherapy can initially reduce the tumor size. The use of temozolomide both during radiotherapy and for six months post radiotherapy results in a significant increase in median survival with minimal additional toxicity. This treatment regime is now standard for most cases of glioblastoma where the patient is not enrolled in a clinical trial. Temozolomide seems to work by sensitizing the tumor cells to radiation. The U.S. Food and Drug Administration approved Avastin (bevacizumab) to treat patients with glioblastoma at progression after standard therapy.

In certain embodiments, the disclosure relates to administering compositions disclosed herein for the management of cancers or tumors in the brain by convection-enhanced delivery (CED). CED is a method of administrating compositions by direct infusion into the brain interstitial spaces utilizing a fluid pressure gradient after catheter placement.

In addition to treating cancer and plasma cell malignancies, depletion of antibody secreting plasma cells could also be used to treat antibody-mediated autoimmune (e.g., lupus erythematosis) and allergic diseases such as those that are not alleviated by B cell depletion with anti-CD20 monoclonal antibodies, because the harmful autoantibodies and allergen-reactive antibodies are produced by long-lived plasma cells lacking the CD20 antigen.

In certain embodiments the disclosure relates to treating an autoimmune disease comprising administering an effective amount of a MM3 fusion or humanized Slit2-MM3 fusion to a subject in need thereof. In certain embodiments, the autoimmune disease is lupus erythematosus, multiple sclerosis, amyotrophic lateral sclerosis, autoimmune hepatitis, autoimmune pancreatitis, Behçet's disease, celiac disease, diabetes mellitus type 1, Guillain-Barre syndrome, psoriatic arthritis, and rheumatoid arthritis.

Experimental

Monoclonal VLR Antibodies with Unique Binding Specificities

The fundamentally different protein architecture combined with the large evolutionary distance suggests that VLR antibodies may detect antigens that cannot be detected by conventional antibodies for architectural or tolerogenic reasons (i.e., the need of the host to prevent the generation of antibodies that recognize "self" and thus lead to autoimmune complications). The evolutionary distance of lampreys and the radically different protein architecture of VLR antibodies make them ideal reagents for the discovery of biomarkers which cannot be detected using conventional antibodies for structural or tolerogenic reasons. The binding characteristics of VLR antibody MM3 does not correspond to any known cell surface antigens, thereby supporting the unique antigen recognition properties of VLR antibodies. Monoclonal lamprey VLR antibodies that bind specific human hematopoietic cell populations have been identified. The analysis of binding specificities of several of these VLR antibodies indicates that they recognize antigenic structures to which no conventional mammalian monoclonal antibodies have been raised.

Recombinant VLR antibodies are generated by transfection of the cDNA encoding the antibodies into human HEK293 cells. The recombinant VLR antibodies are secreted into the cell supernatant and subsequently used to determine cell specificity. The recombinant versions of these VLR sequences include incorporated stretches of 6 codons encoding histidine residues for efficient purification of monoclonal VLR antibodies as well as for flow cytometry detection of bound VLR antibodies.

Humanized VLRB Clone RBC36 Using Human Slit2-D2 as the Scaffold

Han et al. report, 2008, Science 321:1834-183, the crystal structure of the VLR RBC36 ectodomain (ECD) in complex with the H-trisaccharide derived from the H-antigen of human blood group O erythrocytes at 1.67 Å resolution by molecular replacement, using our lamprey VLR2913 crystal structure. The type II H-antigen trisaccharide is α-1-Fucp-(1→2)-β-d-Galp-(1→4)-β-d-GlcNacp-OH.

Figure 7:
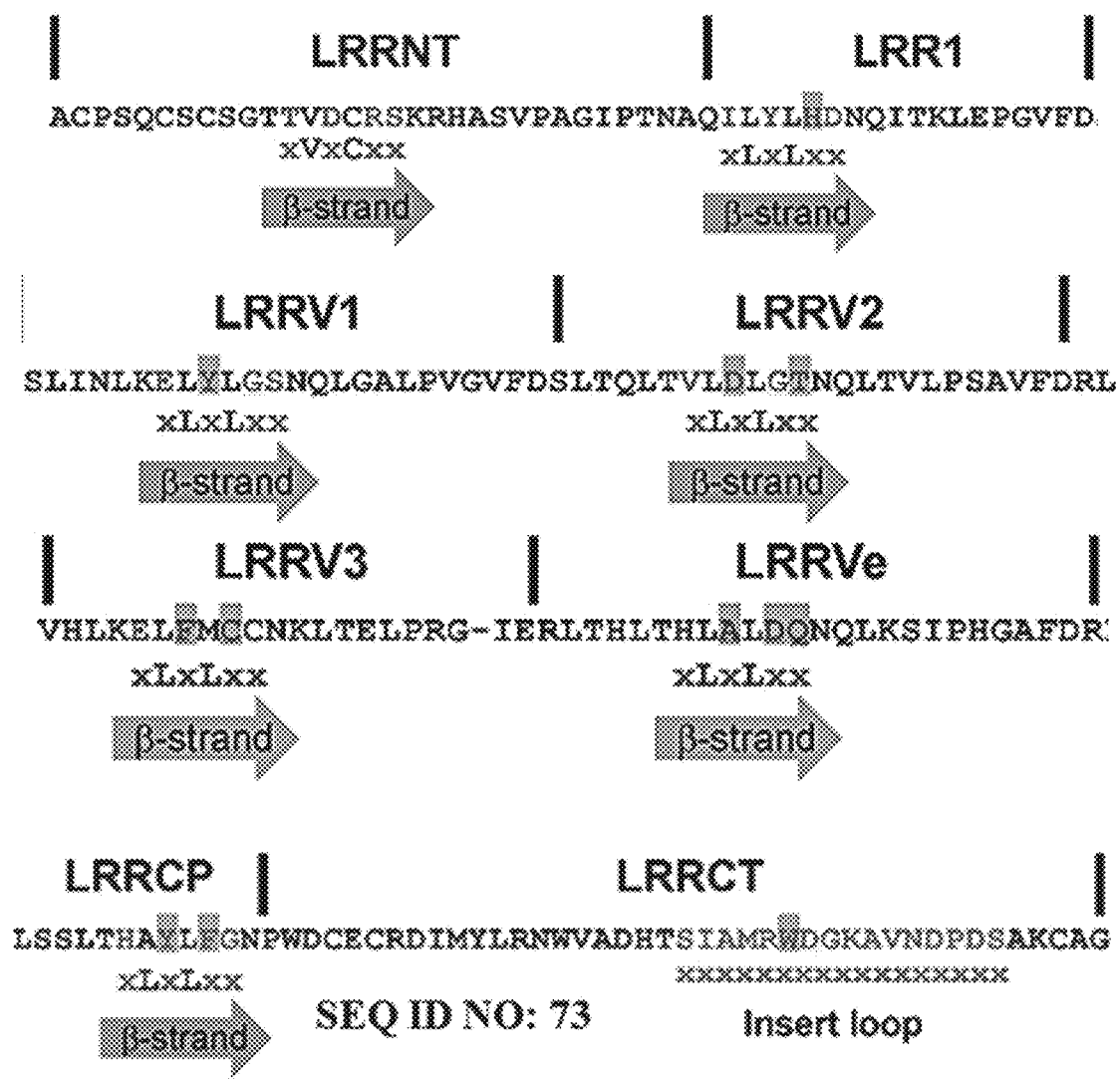
Figure 9:
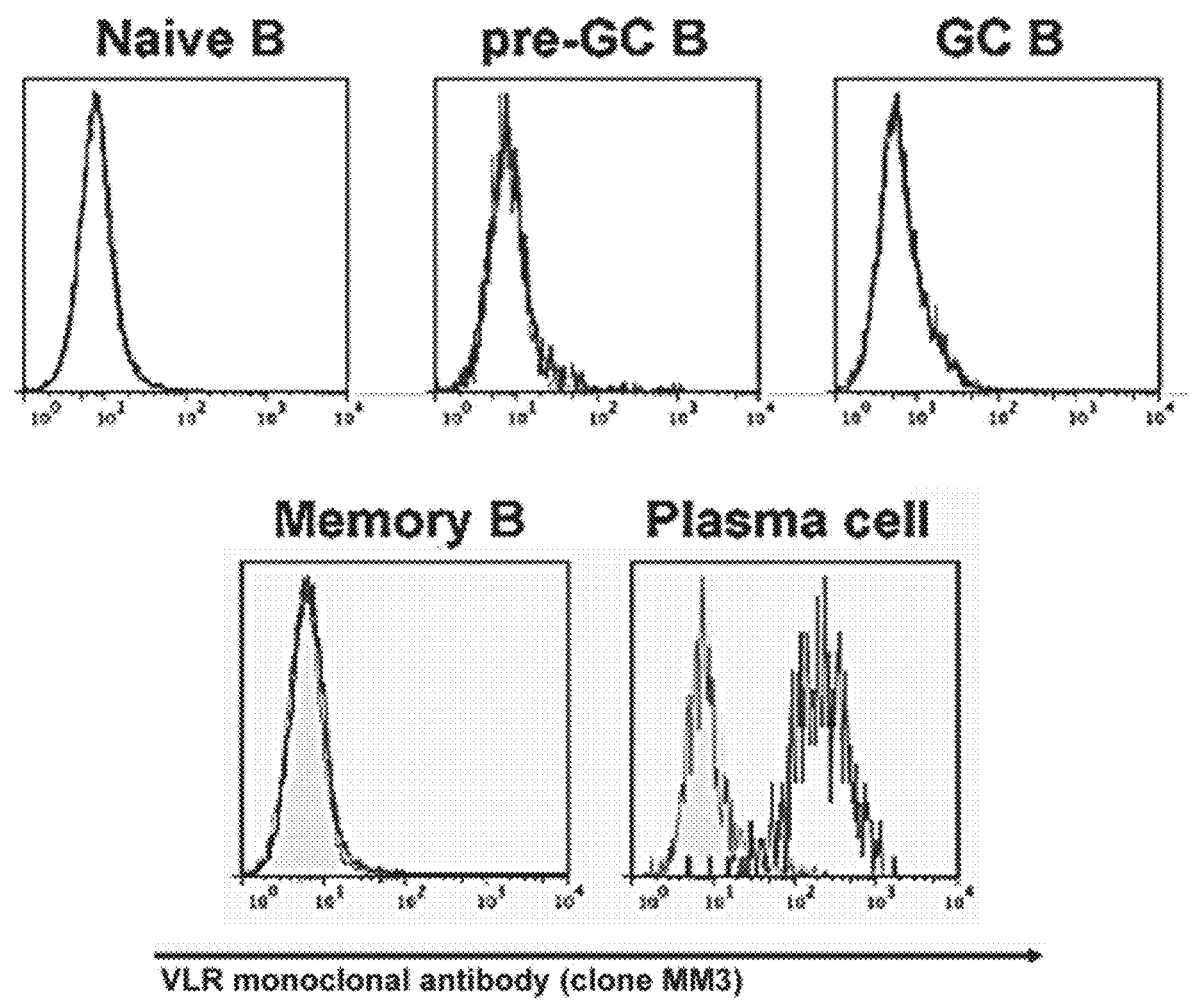
Figure 10:
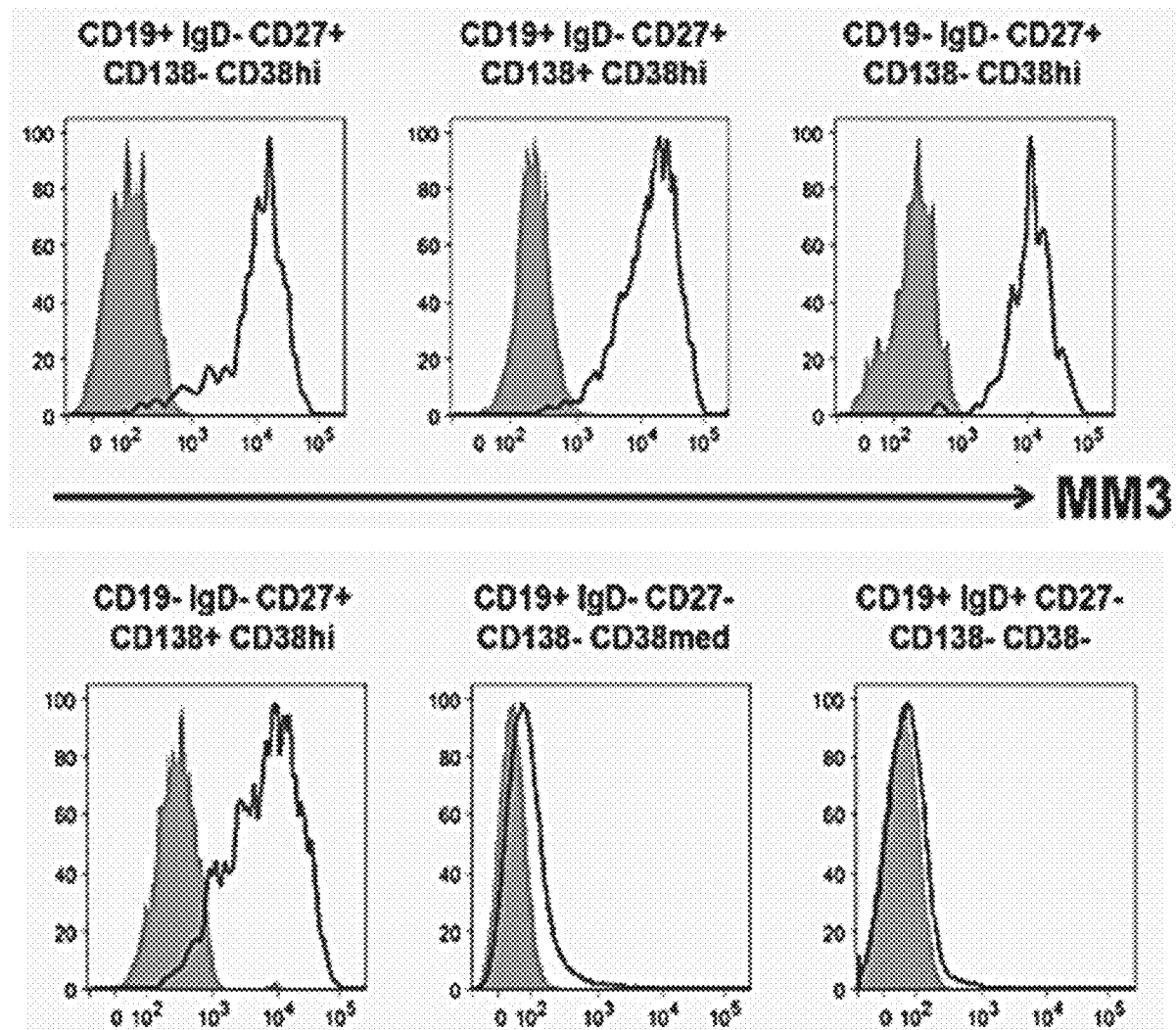

To create a humanized VLRB antibody using the Slit2-D2 scaffold, variable amino acid positions from RBC36 are grafted onto the corresponding positions on Slit-D2 (See FIG. 7), resulting in the following sequence (SEQ ID NO: 1),

CPAACTCSNNTVDCRSKGLTEIPTNLPETITIIYLHDNTIKVIPPGAFSPY

KKLREIYLGSNQISELAPDAFQGLRSLNVLDLGTNKITELPKSLFEGLFSL

QELFLCCNKINCLRVDAFQDLHNLNHLALDQNKLQTIAKGTFSPLRAIQHM

YLFGNPFICDCHLKWLADYLHIAMRWDGKAVNDPDSARCTSPRRLANKRIG

QIKSKKFRC.

Wild-type Slit-D2 (See FIG. 7, top, SEQ ID NO: 2) is composed of 206 amino acids, underlined, some of the amino acids were removed from the LRRCT region.

GSLHCPAACTCSNNIVDCRGKGLTEIPTNLPETITEIRLEQNTIKVIPPGA

FSPYKKLRRIDLSNNQISELAPDAFQGLRSLNSLVLYGNKITELPKSLFEG

LFSLQLLLLNANKINXLRVDAFQDLHNLNLLSLYDNKLQTIAKGTFSPLRA

IQTMHLAQNPFICDCHLKWLADYLHTNPIETSGARCTSPRRLANKRIGQIK

SKKFRCSAAAHHHHHH.

41 amino acids from VLRB clone RBC36 were grafted onto the remaining 196 amino acids of the Slit-D2 scaffold, including substitution of 26 amino acids in the LRRNT, LRR1, LRRVs (red with gray background), and insertion of 15 amino acids into the LRRCT region that encode for the variable insert loop (red with gray background and underlined). In the final 213 amino acid humanized sequence, 41 are derived from the lamprey VLR and 172 are derived from human Slit2-D2. (% human=172/213=80.8%; % lamprey VLR=41/213=19.2%). Some of the variable positions do not make contact with the antigen in the RBC36-H trisaccharide crystal structure. For instance, none of the amino acids in the LRRNT and only one residue in LRR1 make contact with the H trisaccharide. Therefore, it may only be necessary to substitute antigen contacting residues and perhaps a few of the neighboring residues. However, substitution of the all of the variable amino acid positions could be used as a general approach to humanize a VLRB monoclonal antibody when VLR:antigen crystal structure or mutational binding site data are not available. For example, SEQ ID NO: 24 contains a loop of RBC38 and three amino acids grafted into Slit2-D2, designated "Slit-M4." Slit-M4 binds to the type II H-antigen trisaccharide is α-1-Fucp-(1→2)-β-d-Galp-(1→4)-β-d-GlcNacp-OH, (SEQ ID NO: 24)
CPAACTCSNNIVDCRGKGLTEIPTNLPETITEIRLEQNTIKVIPPGAFSPY

KKLRRIDLSNNQISELAPDAFQGLRSLNSLDLGGNKITELPKSLFEGLFSL

QLLLLNANKINXLRVDAFQDLHNLNLLSLDDNKLQTIAKGTFSPLRAIQTM

HLAQNPFICDCHLKWLADYLSIAMRWDGKAVNDPDSARCTSPRRLANKRIG

QIKSKKFRC.

In Slit-M4, 195 of 214 amino acid positions are human (91%).

Each β-strand on the VLR concave surface (encoded by LRRNT, LRR1, LRRV, LRRVe and LRRCP) has 4 variable positions, defined by xLxLxx (SEQ ID NO: 84) motif, where x is any amino acid (note that leucine residues in this motif are occasionally replaced by other hydrophobic amino acids including isoleucine, valine and methionine). The leucines in this motif do not make antigen contacts, and instead face the interior of the protein to form the hydrophobic core of the LRR solenoid by packing against a conserved phenylalanine residue located on the convex surface that also faces the interior. The variable amino acid positions face outward on the concave surface and collectively form the antigen binding surface, along with the variable insert loop in the LRRCT. Since the variable amino acids are located on β-strands that form rigid secondary structures, and they are always located in one of the four positions in the xLxLxx (SEQ ID NO: 84) motif, the corresponding position of the a residue from a VLR to the Slit2-D2 scaffold can be determined from the primary amino acid sequence, even without structural data.

Figure 11:
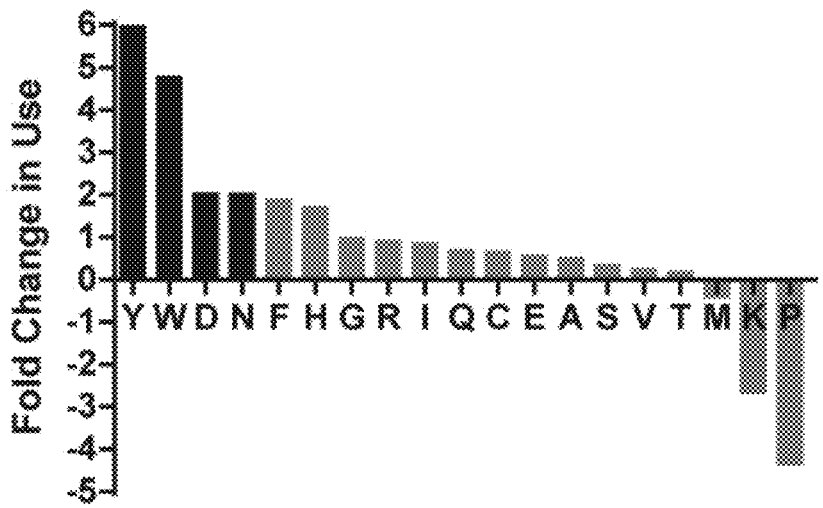

Using RBC36 as an example, Asp153 is in the third variable position of the LRRVe LRR motif SEQ ID NO:7 (HLALDQ). The LRR motif sequence in the LRRVe of Slit-D2 is LLSLYD (SEQ ID NO: 16), such that to graft Asp153 from RBC36 onto the Slit2-D2 scaffold, it is only necessary to exchange the corresponding amino acid at the third position of the LRRVe xLxLXx (SEQ ID NO: 84) motif. In this case the substitution would be the aspartic acid of RBC36 for the tyrosine of Slit2-D2 (e.g., the LRRVe from Slit2-D2 is changed from LLSLYD (SEQ ID NO: 16) to LLSLDD (SEQ ID NO: 85). Although, in principle any amino acid could be used in the variable positions, the amino acid usage is biased towards a subset of amino acids. Tyrosine (Tyr) is the most frequently used amino acid, followed by other aromatic amino acids (phenylalanine (Phe), tryptophan (Trp) and histidine (His)), asparagines (Asn) and aspartic acid (Asp). Furthermore, in the four available VLR: antigen crystal structures, the majority of antigen contacts are formed by this subset of amino acids (FIG. 11). In RBC36, of the 12 amino acids that contact the H-trisaccharide, there are 2 Tyr, 2 Phe, 1 Trp, 2 Asp, and 1 His, such that 9 of 12 antigen-binding amino acids are from this subset of residues. A similar pattern is observed in the other three VLR structures. Also in all four VLR:antigen crystal structures, the more C-terminal LRR modules (LRRVe, LRRCP and LRRCT, FIG. 7) make the most antigen contacts, and the LRRNT only makes contact with antigen in one of the structures, VLR4-BclA, and even then it is only a single amino acid. Therefore, even without VLR-antigen crystal structure data, these observations can be used to guide selection of residues to graft onto the Slit2-D2 scaffold.

Fusion of the VLRB LRRCT loop on the SLIT2 scaffold may be amenable to variants. The LRRCT loop in both the VLR and SLIT structures is preceded by an alpha-helix (shown in FIG. 13). Specifically contemplated variants may be in the addition or deletion of 1, 2, 3, or 4 amino acids wherein the SLIT2 sequences end and the VLR loop sequence begins after the alpha-helix. The LRRCT loops of VLRs can vary in length and sequence composition, so one can add amino acids and determined experimentally an optimal sequence—additional residues at the alpha-helix: loop junction to get the loop in the right orientation for binding. On the other side of the loop where it is fused back to the SLIT2 scaffold there is a conserved cysteine preceded by an R or K residue in both VLRs and SLIT2 that defines the end of the LRRCT loop (FIG. 13). In certain embodiments, the disclosure relates to variant which included the addition or deletion of 1, 2, 3, or 4 amino acids at the end of the LRRCT loop.

Thus, in certain embodiments, the disclosure contemplates variants of the Slit2-D2 sequences herein wherein the humanized Slit2 VLR sequences or humanized Slit2-MM3 sequences comprise a segment (SEQ ID NO: 78) CDCHLKWLADYL-[X]$_m$-[Loop Sequence of VLR or MM3]-X$^5$C or CDCHLKWLADYL-[X]$_m$-[Loop Sequence of VLR or MM3]-AX$^5$C, wherein bolded is the alpha-helix, [X]$_m$ is optionally X$^1$, X$^1$X$^2$, X$^1$X$^2$X$^3$, X$^1$X$^2$X$^3$X$^4$ (SEQ ID NO: 83) wherein X$^1$ is H, X$^2$ is T, X$^3$ is N, X$^4$ is P, and X$^5$ is an R or K.

Humanization of VLRs will not be limited to Slit-family proteins. There are many other human LRR-based receptors with structural similarity (e.g., greater than 30-40% sequence identity) to lamprey VLRs that could also be used as scaffolds. This example only serves to illustrate the general humanization concept. Besides substitution of variable amino acid positions, it may also be necessary to make minor changes to amino acids away from the antigen-binding site in order to optimize the conformation and surface complementarity of the humanized VLR.

Humanized VLRB Fusions

The clearance of tumor cells in vivo by many therapeutic antibodies is mediated by the constant region (Fc) of the antibody. The constant region of human IgG1 binds to complement and Fcγ receptors (FcγR) via the CH2 domain, which facilitates killing of target cells via complement dependent cytotoxicity (CDC), antibody-dependent cellular cytotoxicity (ADCC), and phagocytic engulfment of antibody-opsonized cells by FcγR-bearing macrophages. Fusion proteins consisting of the antigen-binding domain of the VLR and the constant region of human antibodies, such as IgG1, will couple the unique antigen detection of VLR antibodies with human mechanisms of immune clearance. The constant regions of human IgG antibodies also increase the half-life of the antibodies in human plasma. FcRn binds to the CH2 and CH3 domains of the IgG constant region and facilitates recycling of the antibodies from endocytic compartments, which extends their presence in circulation and increases their efficacy as therapeutics.

Figure 5:
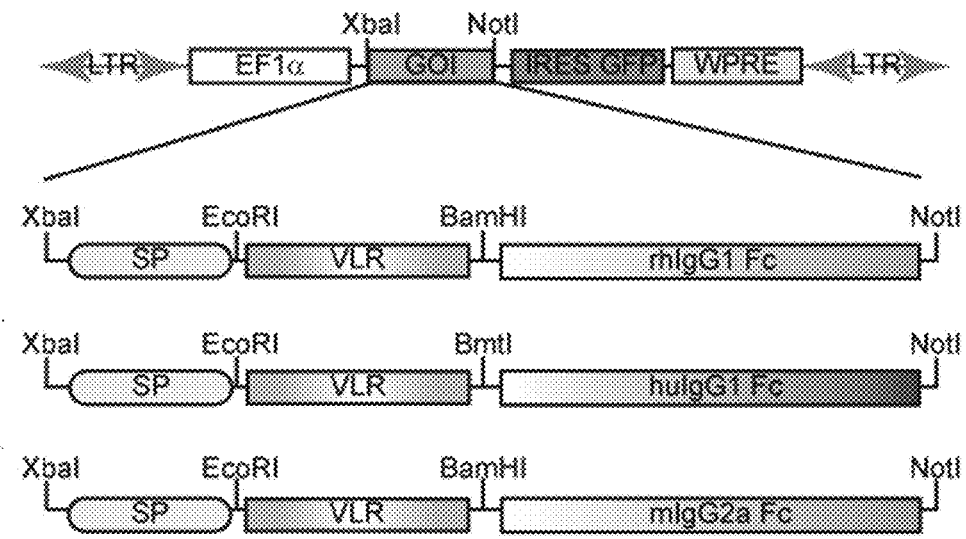
FIG. 5 illustrates mammalian expression vectors.
Figure 6:
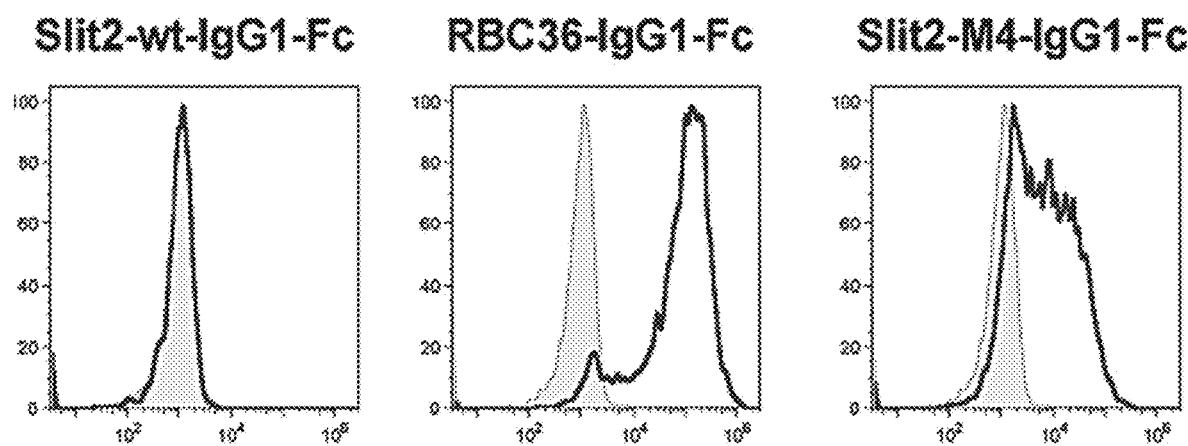
FIG. 6 shows data indicating humanized RB36 binds to the H-trisaccharide. Human Slit2-D2 wild-type (left), Lamprey RBC36 VLR (center) and SLIT2-RBC36 mutant (right) were expressed as IgG Further, the dates of publication provided could be different from the actual publication dates that may need to be independently confirmed.

Vectors were made for expression of VLRs fused to the Fc region of (1) rhesus macaque IgG1, (2) human IgG1 and (3) mouse IgG2a (FIG. 5). The expression constructs are in lentivirus-based vectors under the control of the elongation factor 1α (EF1α) promoter that allows for expression by transient transfection or stable lentiviral transduction after transfection of the construct in packaging cell lines. Both approaches were used to express VLRs in HEK-293 and CHO cells The expression vector also contains an IRES-GFP sequence for sorting cells with highly expression. MM3 VLR-IgG1-Fc protein was obtained using a stationary culture CELLine bioreactor flask (Integra Biosciences).

In certain embodiments, the disclosure contemplates conjugating modified human amino acid sequences, a humanized VLRB sequence, with a human Fc sequence, typically the consensus sequences, to express them in *E. coli* as fusions to human IgG1 Fc. The amino acid sequence of a human IgG1 Fc sequence portion of certain embodied Fc fusion proteins are as follows:

(SEQ ID NO: 18)
DKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGFY

-continued
PSDIAVEWESNGQPENNYKTTPPVLDSDGSFFLYSKLTVDKSRWQQGNVFS

CSVMHEALHNHYTQKSLSLSPGK

The full amino acid sequences of certain embodiments of humanized VLRB sequence-Fc sequence fusion proteins are as follows M-Fc sequence- humanized VLRB sequence
(SEQ ID NO: 19)
MDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVF

SCSVMHEALHNHYTQKSLSLSPGKCPAACTCSNNTVDCRSKGLTEIPTNLP

ETITIIYLHDNTIKVIPPGAFSPYKKLREIYLGSNQISELAPDAFQGLRSL

NVLDLGTNKITELPKSLFEGLFSLQELFLCCNKINCLRVDAFQDLHNLNHL

ALDQNKLQTIAKGTFSPLRAIQHMYLFGNPFICDCHLKWLADYLHIAMRWD

GKAVNDPDSARCTSPRRLANKRIGQIKSKKFRC

M- humanized VLRB sequence-Fc sequence
(SEQ ID NO: 20)
MCPAACTCSNNTVDCRSKGLTEIPTNLPETITIIYLHDNTIKVIPPGAFSP

YKKLREIYLGSNQISELAPDAFQGLRSLNVLDLGTNKITELPKSLFEGLFS

LQELFLCCNKINCLRVDAFQDLHNLNHLALDQNKLQTIAKGTFSPLRAIQH

MYLFGNPFICDCHLKWLADYLHIAMRWDGKAVNDPDSARCTSPRRLANKRI

GQIKSKKFRCDKTHTCPPCPAPELLGGPSVFLFPPKPKDTLMISRTPEVTC

VVVDVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTKNQV

SLTCLVKGFYPSDIAVEWESNGQPENNYKTTPPVLDSDGSFFLYSKLTVDK

SRWQQGNVFSCSVMHEALHNHYTQKSLS

One may lyse *E. coli* cells expressing humanized VLRB sequence and Fc sequence fusion proteins using high-pressure homogenization, and inclusion bodies. After subsequent protein folding, selective precipitation, and filtration, one may employ chromatographic purification steps (e.g., ion exchange chromatography, Protein A, or hydroxyapatite chromatography).

In certain embodiments, the VLRs or modified VLRs or fragments may be fused to a signal-transduction component of the T-cell antigen receptor such as CD3-zeta. In certain embodiments, the signal-transduction component of the T-cell antigen receptor is a peptide with an immunoreceptor tyrosine-based activation motif with the consensus sequence YXXLXXXXXXXYXXL (SEQ ID NO: 52) wherein X is any amino acid L is leucine or isoleucine, wherein SEQ ID NO: 52 optionally has one or two X amino acid deletions within the middle segment XXXXXXXX (SEQ. ID NO: 53). The immunoreceptor tyrosine-based activation motif (underlined) is in the partial CD3-zeta sequence (SEQ ID NO: 54)
AQLPITEAQSFGLLDPKLCYLLDGILFIYGVILTALFLRVKFSRSADAPAY

QQGQNQLYNELNLGRREEYDVLDKRRGRDPEMGGKPQRRKNPQEGLYNELQ

KDKMAEAYSEIGMKGERRRGKGHDGLYQGLSTATKDTYDALHMQALPPR or fragments or variants, e.g. having 1, 2, or 3 amino acid deletion, addition, or substitution variants, or a sequence with greater than 50, 60, 70, 80, 90, 95% or greater identity thereto.

In certain embodiments, the signal-transduction component of the T-cell antigen receptor is a peptide with a immunoreceptor tyrosine-based activation motif (underlined) with the sequence of immunoglobulin epsilon receptor subunit gamma precursor (SEQ ID NO: 55)
IPAVVLLLLLLVEQAAALGEPQLCYILDAILFLYGIVLTLLYCRLKIQVRK

AAITSYEKSDGVYTGLSTRNQETYETLKHEKPPQ fragments or variants thereof variants or a sequence with greater than 50, 60, 70, 80, 90, 95% or greater identity thereto.

Binding of Humanized RBC36 to the H-Trisaccharide

The Slit2-D2 mutants were cloned into the lentiviral expression vector containing the IgG1-Fc, and expressed in HEK-293T cells by transient transfection. Expression of the Slit2-D2 mutants was verified by western blotting the supernatants with an anti-IgG-HRP conjugated secondary antibody. The supernatants were used to stain the CHO-H cell line and binding was detected with an anti-IgG-PE conjugated secondary Ab by flow cytometry. As a positive control, CHO-H cells were also stained with wild-type RBC36-IgG-Fc fusion protein. The Slit-M4-IgG-Fc protein stained the CHO-H cells, demonstrating that the H-trisaccharide specificity could be transferred to the Slit2-D2 scaffold (FIG. 6).

Human Plasma Cell Specific VLR mAb (MM3)

A plasma cell-specific VLR mAb (MM3) were produced by immunizing lampreys with human multiple myeloma cells. Mouse antibodies against human plasma cell antigens have been previously made, but none are plasma cell specific. MM3 VLR mAb binds to both normal (25 of 25 donor samples tested) and malignant human plasma cells (27 of 32 myeloma patients), but does not bind to other B or hematopoietic lineage cells (FIG. 9). MM3 also recognizes plasma cells in non-human primates (rhesus macaque and sooty mangabes), but it does not bind to mouse plasma cells. To confirm that the $MM3^+$ cells from rhesus macaque bone marrow were plasma cells, they were sorted by flow cytometry and analyzed by transmission electron microscopy. The $MM3^+$ cells had a small, dense eccentric nucleus and large cytoplasmic volume with greatly expanded rough endoplasmic reticulum and golgi, which are characteristic features of plasma cells. The conservation of the MM3 antigen on plasma cells in non-human primates provides a model system for evaluation of the ability of VLR antibodies to target and deplete plasma cells in vivo. Multiparameter flow cytometry was used to analyze expression of the MM3 on human bone marrow-derived plasma cell subsets from healthy human donors based on the expression of CD19 and CD138 (FIG. 10). The MM3 VLR mAb stained all four CD38hi plasma cell subsets, including the long-lived plasma cell population (CD19−, CD27+, CD138+, CD38hi). It also stains subpopulations of Ab-secreting cells in human bone marrow that do not express CD138, the most widely used plasma cell marker.

In certain embodiments, the disclosure relates to a polypeptide or fusion comprising a MM3 antigen binding domain sequence (SEQ ID NO: 56)

ACPSQCSCPGTDVNCHERRLASVPAEIPTTTKILRLYINQITKLEPGVFDR

LTQLTQLGLWDNQLQALPEGVFDRLVNLQKLYLNQNQLLALPVGVFDKLTQ

-continued

LTYLDLNNNQLKSIPRGAFDNLKSLTHIWLYGNPWDCECSDILYLKNWIVQ

HASIVNPHPYGGVDNVKCSGTNTPVRAVTEASTSPSKCPG or variants thereof.

In certain embodiments, the variants are those with greater than 80, 85, 90, 95, 97, 98% percent identity or similarity thereto. In certain embodiments, the variants contain one, two, or three amino acid substitutions, deletions or insertions. In certain embodiments, the substitutions are conserved substitutions.

MM3 full sequence including signal peptide and stalk (underlined)

(SEQ ID NO: 57)
MWIKWIATLVAFGALVQSAVACPSQCSCPGTDVNCHERRLASVPAEIPTTT

KILRLYINQITKLEPGVFDRLTQLTQLGLWDNQLQALPEGVFDRLVNLQKL

YLNQNQLLALPVGVFDKLTQLTYLDLNNNQLKSIPRGAFDNLKSLTHIWLY

GNPWDCECSDILYLKNWIVQHASIVNPHPYGGVDNVKCSGTNTPVRAVTEA

STSPSKCPGYVATTTTPTTTTPEFIPETTTSPQPVITTQKPKPLWNFNCTS

IQERKNDGGDCGKPACTTLLNCANFLSCLCSTCALCRKR

Humanization of the MM3 VLR mAb

In certain embodiments, the disclosure contemplates a Slit2-MM3 polypeptides comprising (SEQ ID NO: 64) or variants thereof,
CPAACTCSNNIVDCRGKGLTEIPTNLPETITEIRLEQNTIKVIPPGAFSPY

KKLRILRLYINQISELAPDAFQGLRSLNQLVLWDNKITELPKSLFEGLFSL

QLLYLNANKINCLRVDAFQDLHNLNYLDLNNNKLQTIAKGTFSPLRAIQHI

WLYGNPFICDCHLKWLADYLHASIVNPHPYGGVDNARCTSPRRLAN;

(SEQ ID NO: 74) or variants thereof,
CPAACTCSNNIVDCRGKGLTEIPTNLPETITEIRLEQNTIKVIPPGAFSPY

KKLRILRLYINQISELAPDAFQGLRSLNQLVLWDNKITELPKSLFEGLFSL

QLLYLNANKINCLRVDAFQDLHNLNYLDLNNNKLQTIAKGTFSPLRAIQHI

WLYGNPFICDCHLKWLADYLHHASIVNPHPYGGVDNARCTSPRRLAN;

(SEQ ID NO: 75) or variants thereof,
CPAACTCSNNIVDCRGKGLTEIPTNLPETITEIRLEQNTIKVIPPGAFSPY

KKLRILRLYINQISELAPDAFQGLRSLNQLVLWDNKITELPKSLFEGLFSL

QLLYLNANKINCLRVDAFQDLHNLNYLDLNNNKLQTIAKGTFSPLRAIQHI

WLYGNPFICDCHLKWLADYLHTHASIVNPHPYGGVDNRCTSPRRLAN;

(SEQ ID NO: 76) or variants thereof,
CPAACTCSNNIVDCRGKGLTEIPTNLPETITEIRLEQNTIKVIPPGAFSPY

KKLRILRLYINQISELAPDAFQGLRSLNQLVLWDNKITELPKSLFEGLFSL

QLLYLNANKINCLRVDAFQDLHNLNYLDLNNNKLQTIAKGTFSPLRAIQHI

WLYGNPFICDCHLKWLADYLHTNHASIVNPHPYGGVDNARCTSPRRLAN;
or (SEQ ID NO: 77) or variants thereof,
CPAACTCSNNIVDCRGKGLTEIPTNLPETITEIRLEQNTIKVIPPGAFSPY

KKLRILRLYINQISELAPDAFQGLRSLNQLVLWDNKITELPKSLFEGLFSL

-continued

QLLYLNANKINCLRVDAFQDLHNLNYLDLNNNKLQTIAKGTFSPLRAIQHI

WLYGNPFICDCHLKWLADYLHTNPHASIVNPHPYGGVDNRCTSPRRLAN.

Figure 12:
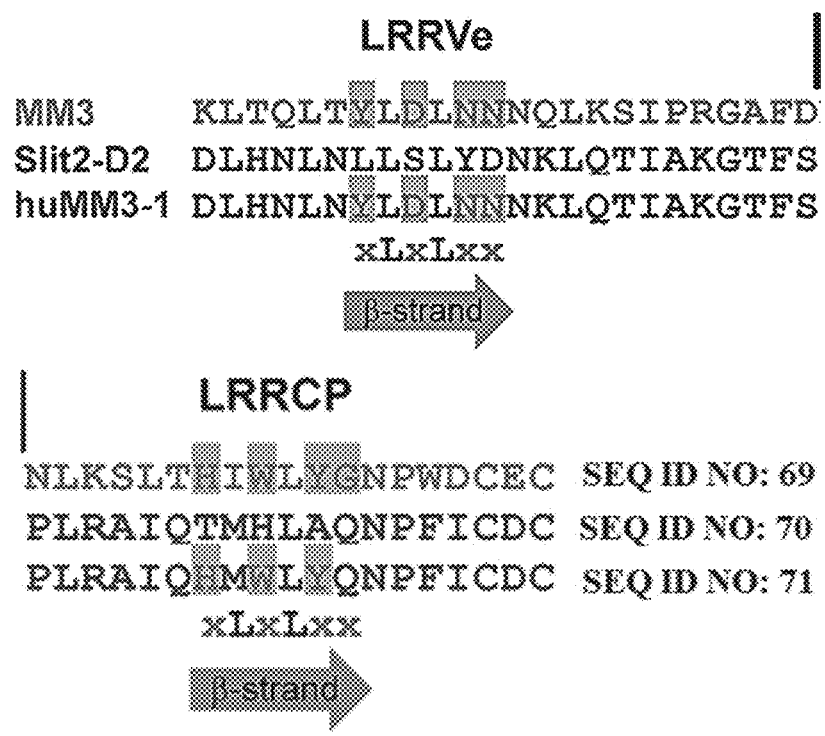

As described FIG. 11, a subset of amino acids in VLR variable positions make the majority of antigen contacts. The β-strands on the concave surface of the MM3 VLR mAb contain a total of 13 of these amino acid residues (4 Tyr, 2 Trp, 4 Asn, 2 Asp and 1 His). Humanized MM3 (huMM3-1) will contain these residues substituted into the corresponding positions on the Slit2-D2 scaffold and the MM3 LRRCT insert grafted at the same location as the RBC36 LRRCT insert. FIG. 12 shows how this approach will be applied to the two most C-terminal LRR modules of MM3 (LRRVe and LRRCP). The figure shows an alignment of MM3 and the human Slit2-D2 scaffold for these modules and VLR the variable amino positions are shaded in gray. In this example, Tyr, Asp and two Asn residues from the MM3 LRRVe and His, Trp and Tyr from the MM3 LRRCP are substituted onto the Slit2-D2 scaffold. The Gln residue in the MM3 LRRCP will not be substituted in the initial construct, because it does not fall into the subset of VLR amino acids that most frequently contact antigen, but it may be added. This approach is applied to the other LRR modules (LRRV, LRR1 and LRRNT).

One expressed HuMM3-1 both as a soluble IgG-Fc fusion protein and in yeast surface display format to evaluate antigen binding. In yeast display format, antigen binding will be determined by staining yeast expressing huMM3 with biotinylated lysates from MM3+ cells and using streptavidin-PE for detection. One can iteratively incorporate additional residues from the variable positions of MM3 onto the huMM3-1 scaffold, following an approach similar to that used for RBC36 humanization.

The invention claimed is:

1. A recombinant vector comprising a nucleic acid encoding a recombinant polypeptide comprising SEQ ID NO: 56 or variant thereof that specifically binds human plasma cells, wherein the variant has more than 95% identity to SEQ ID NO: 56.

2. An expression system comprising a vector of claim 1.

3. The recombinant vector of claim 1 wherein the variant has more than 98% identity to SEQ ID NO: 56.

* * * * *

SEQUENCE LISTING

```
<160> NUMBER OF SEQ ID NOS: 85

<210> SEQ ID NO 1
<211> LENGTH: 213
<212> TYPE: PRT
<213> ORGANISM: Homo sapiens

<400> SEQUENCE: 1

Cys Pro Ala Ala Cys Thr Cys Ser Asn Asn Thr Val Asp Cys Arg Ser
1               5                   10                  15

Lys Gly Leu Thr Glu Ile Pro Thr Asn Leu Pro Glu Thr Ile Thr Ile
            20                  25                  30

Ile Tyr Leu His Asp Asn Thr Ile Lys Val Ile Pro Pro Gly Ala Phe
        35                  40                  45

Ser Pro Tyr Lys Lys Leu Arg Glu Ile Tyr Leu Gly Ser Asn Gln Ile
    50                  55                  60

Ser Glu Leu Ala Pro Asp Ala Phe Gln Gly Leu Arg Ser Leu Asn Val
65                  70                  75                  80

Leu Asp Leu Gly Thr Asn Lys Ile Thr Glu Leu Pro Lys Ser Leu Phe
                85                  90                  95

Glu Gly Leu Phe Ser Leu Gln Glu Leu Phe Leu Cys Cys Asn Lys Ile
            100                 105                 110

Asn Cys Leu Arg Val Asp Ala Phe Gln Asp Leu His Asn Leu Asn His
            115                 120                 125

Leu Ala Leu Asp Gln Asn Lys Leu Gln Thr Ile Ala Lys Gly Thr Phe
        130                 135                 140

Ser Pro Leu Arg Ala Ile Gln His Met Tyr Leu Phe Gly Asn Pro Phe
145                 150                 155                 160

Ile Cys Asp Cys His Leu Lys Trp Leu Ala Asp Tyr Leu His Ile Ala
                165                 170                 175

Met Arg Trp Asp Gly Lys Ala Val Asn Asp Pro Asp Ser Ala Arg Cys
            180                 185                 190

Thr Ser Pro Arg Arg Leu Ala Asn Lys Arg Ile Gly Gln Ile Lys Ser
        195                 200                 205

Lys Lys Phe Arg Cys
    210

<210> SEQ ID NO 2
<211> LENGTH: 220
<212> TYPE: PRT
```

```
<213> ORGANISM: Homo sapiens
<220> FEATURE:
<221> NAME/KEY: misc_feature
<222> LOCATION: (118)..(118)
<223> OTHER INFORMATION: Xaa can be any naturally occurring amino acid

<400> SEQUENCE: 2
```

Gly Ser Leu His Cys Pro Ala Ala Cys Thr Cys Ser Asn Asn Ile Val
 1               5                  10                  15

Asp Cys Arg Gly Lys Gly Leu Thr Glu Ile Pro Thr Asn Leu Pro Glu
            20                  25                  30

Thr Ile Thr Glu Ile Arg Leu Glu Gln Asn Thr Ile Lys Val Ile Pro
        35                  40                  45

Pro Gly Ala Phe Ser Pro Tyr Lys Lys Leu Arg Arg Ile Asp Leu Ser
    50                  55                  60

Asn Asn Gln Ile Ser Glu Leu Ala Pro Asp Ala Phe Gln Gly Leu Arg
65                  70                  75                  80

Ser Leu Asn Ser Leu Val Leu Tyr Gly Asn Lys Ile Thr Glu Leu Pro
                85                  90                  95

Lys Ser Leu Phe Glu Gly Leu Phe Ser Leu Gln Leu Leu Leu Leu Asn
            100                 105                 110

Ala Asn Lys Ile Asn Xaa Leu Arg Val Asp Ala Phe Gln Asp Leu His
        115                 120                 125

Asn Leu Asn Leu Leu Ser Leu Tyr Asp Asn Lys Leu Gln Thr Ile Ala
    130                 135                 140

Lys Gly Thr Phe Ser Pro Leu Arg Ala Ile Gln Thr Met His Leu Ala
145                 150                 155                 160

Gln Asn Pro Phe Ile Cys Asp Cys His Leu Lys Trp Leu Ala Asp Tyr
                165                 170                 175

Leu His Thr Asn Pro Ile Glu Thr Ser Gly Ala Arg Cys Thr Ser Pro
            180                 185                 190

Arg Arg Leu Ala Asn Lys Arg Ile Gly Gln Ile Lys Ser Lys Lys Phe
        195                 200                 205

Arg Cys Ser Ala Ala Ala His His His His His His
    210                 215                 220

```
<210> SEQ ID NO 3
<211> LENGTH: 6
<212> TYPE: PRT
<213> ORGANISM: Homo sapiens

<400> SEQUENCE: 3
```

Ile Ile Tyr Leu His Asp
 1               5

```
<210> SEQ ID NO 4
<211> LENGTH: 6
<212> TYPE: PRT
<213> ORGANISM: Homo sapiens

<400> SEQUENCE: 4
```

Glu Ile Tyr Leu Gly Ser
 1               5

```
<210> SEQ ID NO 5
<211> LENGTH: 6
<212> TYPE: PRT
<213> ORGANISM: Homo sapiens

<400> SEQUENCE: 5
```

```
Val Leu Asp Leu Gly Thr
1               5

<210> SEQ ID NO 6
<211> LENGTH: 6
<212> TYPE: PRT
<213> ORGANISM: Homo sapiens

<400> SEQUENCE: 6

Glu Leu Phe Leu Cys Cys
1               5

<210> SEQ ID NO 7
<211> LENGTH: 6
<212> TYPE: PRT
<213> ORGANISM: Homo sapiens

<400> SEQUENCE: 7

His Leu Ala Leu Asp Gln
1               5

<210> SEQ ID NO 8
<211> LENGTH: 6
<212> TYPE: PRT
<213> ORGANISM: Homo sapiens

<400> SEQUENCE: 8

His Met Tyr Leu Phe Gly
1               5

<210> SEQ ID NO 9
<211> LENGTH: 15
<212> TYPE: PRT
<213> ORGANISM: Homo sapiens

<400> SEQUENCE: 9

Ile Ala Met Arg Trp Asp Gly Lys Ala Val Asn Asp Pro Asp Ser
1               5                   10                  15

<210> SEQ ID NO 10
<211> LENGTH: 213
<212> TYPE: PRT
<213> ORGANISM: Homo sapiens
<220> FEATURE:
<221> NAME/KEY: MISC_FEATURE
<222> LOCATION: (11)..(13)
<223> OTHER INFORMATION: Where X is any amino acid
<220> FEATURE:
<221> NAME/KEY: MISC_FEATURE
<222> LOCATION: (15)..(16)
<223> OTHER INFORMATION: Where X is any amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(37)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(61)
<223> OTHER INFORMATION: Xaa can be any naturally occurring amino acid
<220> FEATURE:
<221> NAME/KEY: misc_feature
```

```
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (132)..(133)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (156)..(157)
<223> OTHER INFORMATION: Xaa can be any naturally occurring amino acid
<220> FEATURE:
<221> NAME/KEY: misc_feature
<222> LOCATION: (175)..(189)
<223> OTHER INFORMATION: Xaa can be any naturally occurring amino acid

<400> SEQUENCE: 10

Cys Pro Ala Ala Cys Thr Cys Ser Asn Asn Xaa Xaa Xaa Cys Xaa Xaa
1               5                   10                  15

Lys Gly Leu Thr Glu Ile Pro Thr Asn Leu Pro Glu Thr Ile Thr Xaa
            20                  25                  30

Ile Xaa Xaa Xaa Xaa Asn Thr Ile Lys Val Ile Pro Pro Gly Ala Phe
        35                  40                  45

Ser Pro Tyr Lys Lys Leu Arg Xaa Ile Xaa Xaa Xaa Xaa Asn Gln Ile
    50                  55                  60

Ser Glu Leu Ala Pro Asp Ala Phe Gln Gly Leu Arg Ser Leu Asn Xaa
65                  70                  75                  80

Leu Xaa Leu Xaa Xaa Asn Lys Ile Thr Glu Leu Pro Lys Ser Leu Phe
            85                  90                  95

Glu Gly Leu Phe Ser Leu Gln Xaa Leu Xaa Leu Xaa Xaa Asn Lys Ile
            100                 105                 110

Asn Cys Leu Arg Val Asp Ala Phe Gln Asp Leu His Asn Leu Asn Xaa
        115                 120                 125

Leu Xaa Leu Xaa Xaa Asn Lys Leu Gln Thr Ile Ala Lys Gly Thr Phe
    130                 135                 140
```

Ser Pro Leu Arg Ala Ile Gln Xaa Met Xaa Leu Xaa Xaa Asn Pro Phe
145                 150                 155                 160

Ile Cys Asp Cys His Leu Lys Trp Leu Ala Asp Tyr Leu His Xaa Xaa
                165                 170                 175

Xaa Xaa Xaa Xaa Xaa Xaa Xaa Xaa Xaa Xaa Xaa Xaa Ala Arg Cys
            180                 185                 190

Thr Ser Pro Arg Arg Leu Ala Asn Lys Arg Ile Gly Gln Ile Lys Ser
        195                 200                 205

Lys Lys Phe Arg Cys
        210

<210> SEQ ID NO 11
<211> LENGTH: 6
<212> TYPE: PRT
<213> ORGANISM: Homo sapiens

<400> SEQUENCE: 11

Ile Val Asp Cys Arg Gly
1               5

<210> SEQ ID NO 12
<211> LENGTH: 6
<212> TYPE: PRT
<213> ORGANISM: Homo sapiens

<400> SEQUENCE: 12

Glu Ile Arg Leu Glu Gln
1               5

<210> SEQ ID NO 13
<211> LENGTH: 6
<212> TYPE: PRT
<213> ORGANISM: Homo sapiens

<400> SEQUENCE: 13

Arg Ile Asp Leu Ser Asn
1               5

<210> SEQ ID NO 14
<211> LENGTH: 6
<212> TYPE: PRT
<213> ORGANISM: Homo sapiens

<400> SEQUENCE: 14

Ser Leu Val Leu Tyr Gly
1               5

<210> SEQ ID NO 15
<211> LENGTH: 6
<212> TYPE: PRT
<213> ORGANISM: Homo sapiens

<400> SEQUENCE: 15

Leu Leu Leu Leu Asn Ala
1               5

<210> SEQ ID NO 16
<211> LENGTH: 6
<212> TYPE: PRT
<213> ORGANISM: Homo sapiens

<400> SEQUENCE: 16

```
Leu Leu Ser Leu Tyr Asp
1               5

<210> SEQ ID NO 17
<211> LENGTH: 6
<212> TYPE: PRT
<213> ORGANISM: Homo sapiens

<400> SEQUENCE: 17

Thr Met His Leu Ala Gln
1               5

<210> SEQ ID NO 18
<211> LENGTH: 227
<212> TYPE: PRT
<213> ORGANISM: Homo sapiens

<400> SEQUENCE: 18

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 19
<211> LENGTH: 441
<212> TYPE: PRT
<213> ORGANISM: Homo sapiens

<400> SEQUENCE: 19

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
```

```
                20                  25                  30
Met Ile Ser Arg Thr Pro Glu Val Thr Cys Val Val Asp Val Ser
                35                  40                  45

His Glu Asp Pro Glu Val Lys Phe Asn Trp Tyr Val Asp Gly Val Glu
 50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
                115                 120                 125

Val Tyr Thr Leu Pro Pro Ser Arg Asp Glu Leu Thr Lys Asn Gln Val
                130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
                195                 200                 205

Met His Glu Ala Leu His Asn His Tyr Thr Gln Lys Ser Leu Ser Leu
                210                 215                 220

Ser Pro Gly Lys Cys Pro Ala Ala Cys Thr Cys Ser Asn Asn Thr Val
225                 230                 235                 240

Asp Cys Arg Ser Lys Gly Leu Thr Glu Ile Pro Thr Asn Leu Pro Glu
                245                 250                 255

Thr Ile Thr Ile Ile Tyr Leu His Asp Asn Thr Ile Lys Val Ile Pro
                260                 265                 270

Pro Gly Ala Phe Ser Pro Tyr Lys Lys Leu Arg Glu Ile Tyr Leu Gly
                275                 280                 285

Ser Asn Gln Ile Ser Glu Leu Ala Pro Asp Ala Phe Gln Gly Leu Arg
                290                 295                 300

Ser Leu Asn Val Leu Asp Leu Gly Thr Asn Lys Ile Thr Glu Leu Pro
305                 310                 315                 320

Lys Ser Leu Phe Glu Gly Leu Phe Ser Leu Gln Glu Leu Phe Leu Cys
                325                 330                 335

Cys Asn Lys Ile Asn Cys Leu Arg Val Asp Ala Phe Gln Asp Leu His
                340                 345                 350

Asn Leu Asn His Leu Ala Leu Asp Gln Asn Lys Leu Gln Thr Ile Ala
                355                 360                 365

Lys Gly Thr Phe Ser Pro Leu Arg Ala Ile Gln His Met Tyr Leu Phe
                370                 375                 380

Gly Asn Pro Phe Ile Cys Asp Cys His Leu Lys Trp Leu Ala Asp Tyr
385                 390                 395                 400

Leu His Ile Ala Met Arg Trp Asp Gly Lys Ala Val Asn Asp Pro Asp
                405                 410                 415

Ser Ala Arg Cys Thr Ser Pro Arg Arg Leu Ala Asn Lys Arg Ile Gly
                420                 425                 430

Gln Ile Lys Ser Lys Lys Phe Arg Cys
                435                 440
```

<210> SEQ ID NO 20
<211> LENGTH: 436
<212> TYPE: PRT
<213> ORGANISM: Homo sapiens

<400> SEQUENCE: 20

Met Cys Pro Ala Ala Cys Thr Cys Ser Asn Asn Thr Val Asp Cys Arg
1               5                   10                  15

Ser Lys Gly Leu Thr Glu Ile Pro Thr Asn Leu Pro Glu Thr Ile Thr
            20                  25                  30

Ile Ile Tyr Leu His Asp Asn Thr Ile Lys Val Ile Pro Pro Gly Ala
        35                  40                  45

Phe Ser Pro Tyr Lys Lys Leu Arg Glu Ile Tyr Leu Gly Ser Asn Gln
    50                  55                  60

Ile Ser Glu Leu Ala Pro Asp Ala Phe Gln Gly Leu Arg Ser Leu Asn
65                  70                  75                  80

Val Leu Asp Leu Gly Thr Asn Lys Ile Thr Glu Leu Pro Lys Ser Leu
                85                  90                  95

Phe Glu Gly Leu Phe Ser Leu Gln Glu Leu Phe Leu Cys Cys Asn Lys
            100                 105                 110

Ile Asn Cys Leu Arg Val Asp Ala Phe Gln Asp Leu His Asn Leu Asn
        115                 120                 125

His Leu Ala Leu Asp Gln Asn Lys Leu Gln Thr Ile Ala Lys Gly Thr
    130                 135                 140

Phe Ser Pro Leu Arg Ala Ile Gln His Met Tyr Leu Phe Gly Asn Pro
145                 150                 155                 160

Phe Ile Cys Asp Cys His Leu Lys Trp Leu Ala Asp Tyr Leu His Ile
                165                 170                 175

Ala Met Arg Trp Asp Gly Lys Ala Val Asn Asp Pro Asp Ser Ala Arg
            180                 185                 190

Cys Thr Ser Pro Arg Arg Leu Ala Asn Lys Arg Ile Gly Gln Ile Lys
        195                 200                 205

Ser Lys Lys Phe Arg Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn

```
                370                 375                 380
Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser
        435

<210> SEQ ID NO 21
<211> LENGTH: 7
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 21

Xaa Xaa Leu Xaa Leu Xaa Xaa
1               5

<210> SEQ ID NO 22
<211> LENGTH: 19
<212> TYPE: PRT
<213> ORGANISM: Homo sapiens
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid

<400> SEQUENCE: 22

Cys Pro Xaa Xaa Cys Thr Cys Ser Xaa Asn Xaa Val Asp Cys Arg Gly
1               5                   10                  15

Lys Xaa Xaa

<210> SEQ ID NO 23
<211> LENGTH: 47
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
```

```
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid

<400> SEQUENCE: 23

Xaa Leu Xaa Leu Xaa Xaa Asn Lys Leu Gln Thr Ile Ala Lys Gly Thr
1               5                   10                  15

Phe Ser Pro Leu Arg Ala Ile Gln Xaa Met Xaa Leu Xaa Xaa Asn Pro
            20                  25                  30

Phe Ile Cys Asp Cys His Leu Lys Trp Leu Ala Asp Tyr Leu His
        35                  40                  45

<210> SEQ ID NO 24
<211> LENGTH: 213
<212> TYPE: PRT
<213> ORGANISM: Homo sapiens
<220> FEATURE:
<221> NAME/KEY: misc_feature
<222> LOCATION: (114)..(114)
<223> OTHER INFORMATION: Xaa can be any naturally occurring amino acid

<400> SEQUENCE: 24

Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Glu
            20                  25                  30

Ile Arg Leu Glu Gln Asn Thr Ile Lys Val Ile Pro Pro Gly Ala Phe
        35                  40                  45

Ser Pro Tyr Lys Lys Leu Arg Arg Ile Asp Leu Ser Asn Asn Gln Ile
    50                  55                  60

Ser Glu Leu Ala Pro Asp Ala Phe Gln Gly Leu Arg Ser Leu Asn Ser
65                  70                  75                  80

Leu Asp Leu Gly Gly Asn Lys Ile Thr Glu Leu Pro Lys Ser Leu Phe
                85                  90                  95

Glu Gly Leu Phe Ser Leu Gln Leu Leu Leu Leu Asn Ala Asn Lys Ile
            100                 105                 110

Asn Xaa Leu Arg Val Asp Ala Phe Gln Asp Leu His Asn Leu Asn Leu
        115                 120                 125

Leu Ser Leu Asp Asp Asn Lys Leu Gln Thr Ile Ala Lys Gly Thr Phe
    130                 135                 140

Ser Pro Leu Arg Ala Ile Gln Thr Met His Leu Ala Gln Asn Pro Phe
145                 150                 155                 160

Ile Cys Asp Cys His Leu Lys Trp Leu Ala Asp Tyr Leu Ser Ile Ala
                165                 170                 175

Met Arg Trp Asp Gly Lys Ala Val Asn Asp Pro Asp Ser Ala Arg Cys
            180                 185                 190

Thr Ser Pro Arg Arg Leu Ala Asn Lys Arg Ile Gly Gln Ile Lys Ser
        195                 200                 205
```

Lys Lys Phe Arg Cys
    210

<210> SEQ ID NO 25
<211> LENGTH: 62
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (23)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (41)..(42)
<223> OTHER INFORMATION: Xaa can be any naturally occurring amino acid
<220> FEATURE:
<221> NAME/KEY: misc_feature
<222> LOCATION: (44)..(47)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid

<400> SEQUENCE: 25

Val Xaa Cys Xaa Xaa Xaa Xaa Leu Xaa Ser Val Pro Ala Xaa Ile Pro
1               5                   10                  15

Thr Thr Thr Xaa Xaa Leu Xaa Xaa Xaa Xaa Asn Xaa Ile Thr Lys Xaa

```
                     20                  25                  30
Xaa Pro Gly Val Phe Asp Xaa Leu Xaa Xaa Leu Xaa Xaa Xaa Xaa Leu
            35                  40                  45

Xaa Xaa Asn Xaa Leu Xaa Xaa Xaa Pro Xaa Gly Xaa Phe Asp
        50                  55                  60

<210> SEQ ID NO 26
<211> LENGTH: 212
<212> TYPE: PRT
<213> ORGANISM: Homo sapiens
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(37)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(61)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (132)..(133)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
```

```
<222> LOCATION: (154)..(154)
<223> OTHER INFORMATION: Xaa can be any naturally occurring amino acid
<220> FEATURE:
<221> NAME/KEY: misc_feature
<222> LOCATION: (156)..(157)
<223> OTHER INFORMATION: Xaa can be any naturally occurring amino acid
<220> FEATURE:
<221> NAME/KEY: misc_feature
<222> LOCATION: (174)..(189)
<223> OTHER INFORMATION: Xaa can be any naturally occurring amino acid

<400> SEQUENCE: 26

Cys Pro Ala Ala Cys Thr Cys Ser Asn Asn Xaa Xaa Xaa Cys Xaa Xaa
1               5                   10                  15

Lys Gly Leu Thr Glu Ile Pro Thr Asn Leu Pro Glu Thr Ile Thr Xaa
            20                  25                  30

Ile Xaa Xaa Xaa Xaa Asn Thr Ile Lys Val Ile Pro Pro Gly Ala Phe
        35                  40                  45

Ser Pro Tyr Lys Lys Leu Arg Xaa Ile Xaa Xaa Xaa Xaa Asn Gln Ile
    50                  55                  60

Ser Glu Leu Ala Pro Asp Ala Phe Gln Gly Leu Arg Ser Leu Asn Xaa
65                  70                  75                  80

Leu Xaa Leu Xaa Xaa Asn Lys Ile Thr Glu Leu Pro Lys Ser Leu Phe
        85                  90                  95

Glu Gly Leu Phe Ser Leu Gln Xaa Leu Xaa Leu Xaa Xaa Asn Lys Ile
            100                 105                 110

Asn Cys Leu Arg Val Asp Ala Phe Gln Asp Leu His Asn Leu Asn Xaa
        115                 120                 125

Leu Xaa Leu Xaa Xaa Asn Lys Leu Gln Thr Ile Ala Lys Gly Thr Phe
    130                 135                 140

Ser Pro Leu Arg Ala Ile Gln Xaa Met Xaa Leu Xaa Xaa Asn Pro Phe
145                 150                 155                 160

Ile Cys Asp Cys His Leu Lys Trp Leu Ala Asp Tyr Leu Xaa Xaa Xaa
                165                 170                 175

Xaa Xaa Xaa Xaa Xaa Xaa Xaa Xaa Xaa Xaa Xaa Xaa Xaa Arg Cys Thr
            180                 185                 190

Ser Pro Arg Arg Leu Ala Asn Lys Arg Ile Gly Gln Ile Lys Ser Lys
            195                 200                 205

Lys Phe Arg Cys
    210

<210> SEQ ID NO 27
<211> LENGTH: 199
<212> TYPE: PRT
<213> ORGANISM: Homo sapiens
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(37)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(61)
<223> OTHER INFORMATION: Xaa can be any naturally occurring amino acid
<220> FEATURE:
<221> NAME/KEY: misc_feature
<222> LOCATION: (80)..(80)
```

```
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (132)..(133)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (156)..(157)
<223> OTHER INFORMATION: Xaa can be any naturally occurring amino acid
<220> FEATURE:
<221> NAME/KEY: misc_feature
<222> LOCATION: (174)..(189)
<223> OTHER INFORMATION: Xaa can be any naturally occurring amino acid

<400> SEQUENCE: 27

Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Xaa
            20                  25                  30

Ile Xaa Xaa Xaa Xaa Asn Thr Ile Lys Val Ile Pro Pro Gly Ala Phe
        35                  40                  45

Ser Pro Tyr Lys Lys Leu Arg Xaa Ile Xaa Xaa Xaa Xaa Asn Gln Ile
    50                  55                  60

Ser Glu Leu Ala Pro Asp Ala Phe Gln Gly Leu Arg Ser Leu Asn Xaa
65                  70                  75                  80

Leu Xaa Leu Xaa Xaa Asn Lys Ile Thr Glu Leu Pro Lys Ser Leu Phe
                85                  90                  95

Glu Gly Leu Phe Ser Leu Gln Xaa Leu Xaa Leu Xaa Xaa Asn Lys Ile
            100                 105                 110

Asn Cys Leu Arg Val Asp Ala Phe Gln Asp Leu His Asn Leu Asn Xaa
            115                 120                 125

Leu Xaa Leu Xaa Xaa Asn Lys Leu Gln Thr Ile Ala Lys Gly Thr Phe
            130                 135                 140
```

```
Ser Pro Leu Arg Ala Ile Gln Xaa Met Xaa Leu Xaa Xaa Asn Pro Phe
145                 150                 155                 160

Ile Cys Asp Cys His Leu Lys Trp Leu Ala Asp Tyr Leu Xaa Xaa Xaa
                165                 170                 175

Xaa Xaa Xaa Xaa Xaa Xaa Xaa Xaa Xaa Xaa Xaa Xaa Arg Cys Thr
            180                 185                 190

Ser Pro Arg Arg Leu Ala Asn
        195
```

```
<210> SEQ ID NO 28
<211> LENGTH: 197
<212> TYPE: PRT
<213> ORGANISM: Homo sapiens
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(61)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (132)..(133)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (156)..(157)
<223> OTHER INFORMATION: Xaa can be any naturally occurring amino acid
<220> FEATURE:
<221> NAME/KEY: misc_feature
<222> LOCATION: (174)..(187)
<223> OTHER INFORMATION: Xaa can be any naturally occurring amino acid

<400> SEQUENCE: 28
```

```
Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Glu
            20                  25                  30

Ile Arg Leu Glu Gln Asn Thr Ile Lys Val Ile Pro Pro Gly Ala Phe
        35                  40                  45

Ser Pro Tyr Lys Lys Leu Arg Xaa Ile Xaa Xaa Xaa Xaa Asn Gln Ile
    50                  55                  60

Ser Glu Leu Ala Pro Asp Ala Phe Gln Gly Leu Arg Ser Leu Asn Xaa
65                  70                  75                  80

Leu Xaa Leu Xaa Xaa Asn Lys Ile Thr Glu Leu Pro Lys Ser Leu Phe
        85                  90                  95

Glu Gly Leu Phe Ser Leu Gln Xaa Leu Xaa Leu Xaa Xaa Asn Lys Ile
            100                 105                 110

Asn Cys Leu Arg Val Asp Ala Phe Gln Asp Leu His Asn Leu Asn Xaa
        115                 120                 125

Leu Xaa Leu Xaa Xaa Asn Lys Leu Gln Thr Ile Ala Lys Gly Thr Phe
        130                 135                 140

Ser Pro Leu Arg Ala Ile Gln Xaa Met Xaa Leu Xaa Xaa Asn Pro Phe
145                 150                 155                 160

Ile Cys Asp Cys His Leu Lys Trp Leu Ala Asp Tyr Leu Xaa Xaa Xaa
                165                 170                 175

Xaa Xaa Xaa Xaa Xaa Xaa Xaa Xaa Xaa Xaa Arg Cys Thr Ser Pro
            180                 185                 190

Arg Arg Leu Ala Asn
        195

<210> SEQ ID NO 29
<211> LENGTH: 199
<212> TYPE: PRT
<213> ORGANISM: Homo sapiens
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
```

```
<222> LOCATION: (132)..(133)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (156)..(157)
<223> OTHER INFORMATION: Xaa can be any naturally occurring amino acid
<220> FEATURE:
<221> NAME/KEY: misc_feature
<222> LOCATION: (174)..(189)
<223> OTHER INFORMATION: Xaa can be any naturally occurring amino acid

<400> SEQUENCE: 29

Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Glu
            20                  25                  30

Ile Arg Leu Glu Gln Asn Thr Ile Lys Val Ile Pro Pro Gly Ala Phe
        35                  40                  45

Ser Pro Tyr Lys Lys Leu Arg Arg Ile Asp Leu Ser Asn Asn Gln Ile
    50                  55                  60

Ser Glu Leu Ala Pro Asp Ala Phe Gln Gly Leu Arg Ser Leu Asn Xaa
65                  70                  75                  80

Leu Xaa Leu Xaa Xaa Asn Lys Ile Thr Glu Leu Pro Lys Ser Leu Phe
            85                  90                  95

Glu Gly Leu Phe Ser Leu Gln Xaa Leu Xaa Leu Xaa Xaa Asn Lys Ile
            100                 105                 110

Asn Cys Leu Arg Val Asp Ala Phe Gln Asp Leu His Asn Leu Asn Xaa
        115                 120                 125

Leu Xaa Leu Xaa Xaa Asn Lys Leu Gln Thr Ile Ala Lys Gly Thr Phe
    130                 135                 140

Ser Pro Leu Arg Ala Ile Gln Xaa Met Xaa Leu Xaa Xaa Asn Pro Phe
145                 150                 155                 160

Ile Cys Asp Cys His Leu Lys Trp Leu Ala Asp Tyr Leu Xaa Xaa Xaa
            165                 170                 175

Xaa Xaa Xaa Xaa Xaa Xaa Xaa Xaa Xaa Xaa Xaa Xaa Xaa Arg Cys Thr
            180                 185                 190

Ser Pro Arg Arg Leu Ala Asn
        195

<210> SEQ ID NO 30
<211> LENGTH: 199
<212> TYPE: PRT
<213> ORGANISM: Homo sapiens
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
```

```
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (132)..(133)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (156)..(157)
<223> OTHER INFORMATION: Xaa can be any naturally occurring amino acid
<220> FEATURE:
<221> NAME/KEY: misc_feature
<222> LOCATION: (174)..(189)
<223> OTHER INFORMATION: Xaa can be any naturally occurring amino acid

<400> SEQUENCE: 30

Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Glu
            20                  25                  30

Ile Arg Leu Glu Gln Asn Thr Ile Lys Val Ile Pro Pro Gly Ala Phe
        35                  40                  45

Ser Pro Tyr Lys Lys Leu Arg Arg Ile Asp Leu Ser Asn Asn Gln Ile
    50                  55                  60

Ser Glu Leu Ala Pro Asp Ala Phe Gln Gly Leu Arg Ser Leu Asn Ser
65                  70                  75                  80

Leu Xaa Leu Xaa Gly Asn Lys Ile Thr Glu Leu Pro Lys Ser Leu Phe
                85                  90                  95

Glu Gly Leu Phe Ser Leu Gln Xaa Leu Xaa Leu Xaa Xaa Asn Lys Ile
            100                 105                 110

Asn Cys Leu Arg Val Asp Ala Phe Gln Asp Leu His Asn Leu Asn Xaa
        115                 120                 125

Leu Xaa Leu Xaa Xaa Asn Lys Leu Gln Thr Ile Ala Lys Gly Thr Phe
    130                 135                 140

Ser Pro Leu Arg Ala Ile Gln Xaa Met Xaa Leu Xaa Xaa Asn Pro Phe
145                 150                 155                 160

Ile Cys Asp Cys His Leu Lys Trp Leu Ala Asp Tyr Leu Xaa Xaa Xaa
                165                 170                 175

Xaa Xaa Xaa Xaa Xaa Xaa Xaa Xaa Xaa Xaa Xaa Xaa Arg Cys Thr
            180                 185                 190

Ser Pro Arg Arg Leu Ala Asn
            195

<210> SEQ ID NO 31
<211> LENGTH: 199
```

```
<212> TYPE: PRT
<213> ORGANISM: Homo sapiens
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (132)..(133)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (156)..(157)
<223> OTHER INFORMATION: Xaa can be any naturally occurring amino acid
<220> FEATURE:
<221> NAME/KEY: misc_feature
<222> LOCATION: (174)..(189)
<223> OTHER INFORMATION: Xaa can be any naturally occurring amino acid

<400> SEQUENCE: 31

Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Glu
            20                  25                  30

Ile Arg Leu Glu Gln Asn Thr Ile Lys Val Ile Pro Pro Gly Ala Phe
        35                  40                  45

Ser Pro Tyr Lys Lys Leu Arg Arg Ile Asp Leu Ser Asn Asn Gln Ile
    50                  55                  60

Ser Glu Leu Ala Pro Asp Ala Phe Gln Gly Leu Arg Ser Leu Asn Ser
65                  70                  75                  80

Leu Val Leu Tyr Gly Asn Lys Ile Thr Glu Leu Pro Lys Ser Leu Phe
                85                  90                  95

Glu Gly Leu Phe Ser Leu Gln Xaa Leu Xaa Leu Xaa Xaa Asn Lys Ile
            100                 105                 110

Asn Cys Leu Arg Val Asp Ala Phe Gln Asp Leu His Asn Leu Asn Xaa
        115                 120                 125

Leu Xaa Leu Xaa Xaa Asn Lys Leu Gln Thr Ile Ala Lys Gly Thr Phe
    130                 135                 140

Ser Pro Leu Arg Ala Ile Gln Xaa Met Xaa Leu Xaa Xaa Asn Pro Phe
145                 150                 155                 160

Ile Cys Asp Cys His Leu Lys Trp Leu Ala Asp Tyr Leu Xaa Xaa Xaa
                165                 170                 175

Xaa Xaa Xaa Xaa Xaa Xaa Xaa Xaa Xaa Xaa Xaa Xaa Xaa Arg Cys Thr
```

Ser Pro Arg Arg Leu Ala Asn
                195

<210> SEQ ID NO 32
<211> LENGTH: 199
<212> TYPE: PRT
<213> ORGANISM: Homo sapiens
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (132)..(133)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (156)..(157)
<223> OTHER INFORMATION: Xaa can be any naturally occurring amino acid
<220> FEATURE:
<221> NAME/KEY: misc_feature
<222> LOCATION: (174)..(189)
<223> OTHER INFORMATION: Xaa can be any naturally occurring amino acid

<400> SEQUENCE: 32

Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Glu
            20                  25                  30

Ile Arg Leu Glu Gln Asn Thr Ile Lys Val Ile Pro Pro Gly Ala Phe
        35                  40                  45

Ser Pro Tyr Lys Lys Leu Arg Arg Ile Asp Leu Ser Asn Asn Gln Ile
    50                  55                  60

Ser Glu Leu Ala Pro Asp Ala Phe Gln Gly Leu Arg Ser Leu Asn Ser
65                  70                  75                  80

Leu Val Leu Tyr Gly Asn Lys Ile Thr Glu Leu Pro Lys Ser Leu Phe
                85                  90                  95

Glu Gly Leu Phe Ser Leu Gln Leu Leu Leu Leu Asn Ala Asn Lys Ile
            100                 105                 110

Asn Cys Leu Arg Val Asp Ala Phe Gln Asp Leu His Asn Leu Asn Xaa
        115                 120                 125

Leu Xaa Leu Xaa Xaa Asn Lys Leu Gln Thr Ile Ala Lys Gly Thr Phe
    130                 135                 140

Ser Pro Leu Arg Ala Ile Gln Xaa Met Xaa Leu Xaa Xaa Asn Pro Phe
145                 150                 155                 160

Ile Cys Asp Cys His Leu Lys Trp Leu Ala Asp Tyr Leu Xaa Xaa Xaa
                165                 170                 175

Xaa Xaa Xaa Xaa Xaa Xaa Xaa Xaa Xaa Xaa Xaa Xaa Xaa Arg Cys Thr
            180                 185                 190

Ser Pro Arg Arg Leu Ala Asn
                195

<210> SEQ ID NO 33
<211> LENGTH: 182
<212> TYPE: PRT
<213> ORGANISM: Homo sapiens
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(20)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (41)..(44)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (91)..(92)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (115)..(116)
<223> OTHER INFORMATION: Xaa can be any naturally occurring amino acid
<220> FEATURE:
<221> NAME/KEY: misc_feature
<222> LOCATION: (135)..(135)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (139)..(140)
<223> OTHER INFORMATION: Xaa can be any naturally occurring amino acid
<220> FEATURE:
<221> NAME/KEY: misc_feature
<222> LOCATION: (157)..(172)
<223> OTHER INFORMATION: Xaa can be any naturally occurring amino acid

<400> SEQUENCE: 33

Gly Leu Thr Glu Ile Pro Thr Asn Leu Pro Glu Thr Ile Thr Xaa Ile
1               5                   10                  15

```
Xaa Xaa Xaa Xaa Asn Thr Ile Lys Val Ile Pro Pro Gly Ala Phe Ser
            20                  25                  30

Pro Tyr Lys Lys Leu Arg Xaa Ile Xaa Xaa Xaa Xaa Asn Gln Ile Ser
            35                  40                  45

Glu Leu Ala Pro Asp Ala Phe Gln Gly Leu Arg Ser Leu Asn Xaa Leu
 50                  55                  60

Xaa Leu Xaa Xaa Asn Lys Ile Thr Glu Leu Pro Lys Ser Leu Phe Glu
 65                  70                  75                  80

Gly Leu Phe Ser Leu Gln Xaa Leu Xaa Leu Xaa Xaa Asn Lys Ile Asn
                 85                  90                  95

Cys Leu Arg Val Asp Ala Phe Gln Asp Leu His Asn Leu Asn Xaa Leu
             100                 105                 110

Xaa Leu Xaa Xaa Asn Lys Leu Gln Thr Ile Ala Lys Gly Thr Phe Ser
             115                 120                 125

Pro Leu Arg Ala Ile Gln Xaa Met Xaa Leu Xaa Xaa Asn Pro Phe Ile
130                 135                 140

Cys Asp Cys His Leu Lys Trp Leu Ala Asp Tyr Leu Xaa Xaa Xaa Xaa
145                 150                 155                 160

Xaa Xaa Xaa Xaa Xaa Xaa Xaa Xaa Xaa Xaa Xaa Xaa Arg Cys Thr Ser
                165                 170                 175

Pro Arg Arg Leu Ala Asn
            180

<210> SEQ ID NO 34
<211> LENGTH: 153
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (38)..(39)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (62)..(63)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
```

<220> FEATURE:
<221> NAME/KEY: misc_feature
<222> LOCATION: (86)..(87)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (110)..(111)
<223> OTHER INFORMATION: Xaa can be any naturally occurring amino acid
<220> FEATURE:
<221> NAME/KEY: misc_feature
<222> LOCATION: (128)..(143)
<223> OTHER INFORMATION: Xaa can be any naturally occurring amino acid

<400> SEQUENCE: 34

```
Ala Phe Ser Pro Tyr Lys Lys Leu Arg Xaa Ile Xaa Xaa Xaa Xaa Asn
1               5                   10                  15

Gln Ile Ser Glu Leu Ala Pro Asp Ala Phe Gln Gly Leu Arg Ser Leu
            20                  25                  30

Asn Xaa Leu Xaa Leu Xaa Xaa Asn Lys Ile Thr Glu Leu Pro Lys Ser
        35                  40                  45

Leu Phe Glu Gly Leu Phe Ser Leu Gln Xaa Leu Xaa Leu Xaa Xaa Asn
50                  55                  60

Lys Ile Asn Cys Leu Arg Val Asp Ala Phe Gln Asp Leu His Asn Leu
65                  70                  75                  80

Asn Xaa Leu Xaa Leu Xaa Xaa Asn Lys Leu Gln Thr Ile Ala Lys Gly
            85                  90                  95

Thr Phe Ser Pro Leu Arg Ala Ile Gln Xaa Met Xaa Leu Xaa Xaa Asn
            100                 105                 110

Pro Phe Ile Cys Asp Cys His Leu Lys Trp Leu Ala Asp Tyr Leu Xaa
        115                 120                 125

Xaa Xaa Xaa Xaa Xaa Xaa Xaa Xaa Xaa Xaa Xaa Xaa Xaa Xaa Xaa Arg
    130                 135                 140

Cys Thr Ser Pro Arg Arg Leu Ala Asn
145                 150
```

<210> SEQ ID NO 35
<211> LENGTH: 129
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:

<221> NAME/KEY: misc_feature
<222> LOCATION: (38)..(39)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (62)..(63)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (86)..(87)
<223> OTHER INFORMATION: Xaa can be any naturally occurring amino acid
<220> FEATURE:
<221> NAME/KEY: misc_feature
<222> LOCATION: (104)..(119)
<223> OTHER INFORMATION: Xaa can be any naturally occurring amino acid

<400> SEQUENCE: 35

Ala Phe Gln Gly Leu Arg Ser Leu Asn Xaa Leu Xaa Leu Xaa Xaa Asn
1               5                   10                  15

Lys Ile Thr Glu Leu Pro Lys Ser Leu Phe Glu Gly Leu Phe Ser Leu
            20                  25                  30

Gln Xaa Leu Xaa Leu Xaa Xaa Asn Lys Ile Asn Cys Leu Arg Val Asp
        35                  40                  45

Ala Phe Gln Asp Leu His Asn Leu Asn Xaa Leu Xaa Leu Xaa Xaa Asn
    50                  55                  60

Lys Leu Gln Thr Ile Ala Lys Gly Thr Phe Ser Pro Leu Arg Ala Ile
65                  70                  75                  80

Gln Xaa Met Xaa Leu Xaa Xaa Asn Pro Phe Ile Cys Asp Cys His Leu
            85                  90                  95

Lys Trp Leu Ala Asp Tyr Leu Xaa Xaa Xaa Xaa Xaa Xaa Xaa Xaa Xaa
            100                 105                 110

Xaa Xaa Xaa Xaa Xaa Xaa Xaa Arg Cys Thr Ser Pro Arg Arg Leu Ala
        115                 120                 125

Asn

<210> SEQ ID NO 36
<211> LENGTH: 76
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature

```
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(76)
<223> OTHER INFORMATION: Xaa can be any naturally occurring amino acid

<400> SEQUENCE: 36

Xaa Leu Xaa Gly Asn Lys Ile Thr Glu Leu Pro Lys Ser Leu Phe Glu
1               5                   10                  15

Gly Leu Phe Ser Leu Gln Xaa Leu Xaa Leu Xaa Xaa Asn Lys Ile Asn
            20                  25                  30

Cys Leu Arg Val Asp Ala Phe Gln Asp Leu His Asn Leu Asn Xaa Leu
        35                  40                  45

Xaa Leu Xaa Xaa Asn Lys Leu Gln Thr Ile Ala Lys Gly Thr Phe Ser
    50                  55                  60

Pro Leu Arg Ala Ile Gln Xaa Met Xaa Leu Xaa Xaa
65                  70                  75

<210> SEQ ID NO 37
<211> LENGTH: 54
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
```

```
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid

<400> SEQUENCE: 37

Xaa Leu Xaa Leu Xaa Xaa Asn Lys Ile Asn Cys Leu Arg Val Asp Ala
1               5                   10                  15

Phe Gln Asp Leu His Asn Leu Asn Xaa Leu Xaa Leu Xaa Xaa Asn Lys
            20                  25                  30

Leu Gln Thr Ile Ala Lys Gly Thr Phe Ser Pro Leu Arg Ala Ile Gln
        35                  40                  45

Xaa Met Xaa Leu Xaa Xaa
    50

<210> SEQ ID NO 38
<211> LENGTH: 30
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid

<400> SEQUENCE: 38

Xaa Leu Xaa Leu Xaa Xaa Asn Lys Leu Gln Thr Ile Ala Lys Gly Thr
1               5                   10                  15

Phe Ser Pro Leu Arg Ala Ile Gln Xaa Met Xaa Leu Xaa Xaa
            20                  25                  30

<210> SEQ ID NO 39
<211> LENGTH: 212
<212> TYPE: PRT
<213> ORGANISM: Homo sapiens
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (32)..(32)
```

```
<223> OTHER INFORMATION: Xaa can be any naturally occurring amino acid
<220> FEATURE:
<221> NAME/KEY: misc_feature
<222> LOCATION: (34)..(37)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(61)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (174)..(189)
<223> OTHER INFORMATION: Xaa can be any naturally occurring amino acid

<400> SEQUENCE: 39

Cys Pro Ala Ala Cys Thr Cys Ser Asn Asn Xaa Xaa Xaa Cys Xaa Xaa
1               5                   10                  15

Lys Gly Leu Thr Glu Ile Pro Thr Asn Leu Pro Glu Thr Ile Thr Xaa
            20                  25                  30

Ile Xaa Xaa Xaa Xaa Asn Thr Ile Lys Val Ile Pro Gly Ala Phe
        35                  40                  45

Ser Pro Tyr Lys Lys Leu Arg Xaa Ile Xaa Xaa Xaa Xaa Asn Gln Ile
50                  55                  60

Ser Glu Leu Ala Pro Asp Ala Phe Gln Gly Leu Arg Ser Leu Asn Xaa
65                  70                  75                  80

Leu Xaa Leu Xaa Xaa Asn Lys Ile Thr Glu Leu Pro Lys Ser Leu Phe
            85                  90                  95

Glu Gly Leu Phe Ser Leu Gln Xaa Leu Xaa Leu Xaa Xaa Asn Lys Ile
            100                 105                 110

Asn Cys Leu Arg Val Asp Ala Phe Gln Asp Leu His Asn Leu Asn Tyr
            115                 120                 125

Leu Asp Leu Asn Asn Asn Lys Leu Gln Thr Ile Ala Lys Gly Thr Phe
        130                 135                 140

Ser Pro Leu Arg Ala Ile Gln His Met Trp Leu Tyr Xaa Asn Pro Phe
145                 150                 155                 160

Ile Cys Asp Cys His Leu Lys Trp Leu Ala Asp Tyr Leu Xaa Xaa Xaa
```

```
                    165                 170                 175
Xaa Xaa Xaa Xaa Xaa Xaa Xaa Xaa Xaa Xaa Xaa Xaa Arg Cys Thr
            180                 185                 190

Ser Pro Arg Arg Leu Ala Asn Lys Arg Ile Gly Gln Ile Lys Ser Lys
            195                 200                 205

Lys Phe Arg Cys
    210

<210> SEQ ID NO 40
<211> LENGTH: 199
<212> TYPE: PRT
<213> ORGANISM: Homo sapiens
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(37)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(61)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (174)..(189)
<223> OTHER INFORMATION: Xaa can be any naturally occurring amino acid

<400> SEQUENCE: 40

Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Xaa
            20                  25                  30

Ile Xaa Xaa Xaa Xaa Asn Thr Ile Lys Val Ile Pro Pro Gly Ala Phe
        35                  40                  45

Ser Pro Tyr Lys Lys Leu Arg Xaa Ile Xaa Xaa Xaa Xaa Asn Gln Ile
    50                  55                  60
```

```
Ser Glu Leu Ala Pro Asp Ala Phe Gln Gly Leu Arg Ser Leu Asn Xaa
 65                  70                  75                  80

Leu Xaa Leu Xaa Xaa Asn Lys Ile Thr Glu Leu Pro Lys Ser Leu Phe
             85                  90                  95

Glu Gly Leu Phe Ser Leu Gln Xaa Leu Xaa Leu Xaa Xaa Asn Lys Ile
            100                 105                 110

Asn Cys Leu Arg Val Asp Ala Phe Gln Asp Leu His Asn Leu Asn Tyr
            115                 120                 125

Leu Asp Leu Asn Asn Asn Lys Leu Gln Thr Ile Ala Lys Gly Thr Phe
        130                 135                 140

Ser Pro Leu Arg Ala Ile Gln His Met Trp Leu Tyr Xaa Asn Pro Phe
145                 150                 155                 160

Ile Cys Asp Cys His Leu Lys Trp Leu Ala Asp Tyr Leu Xaa Xaa Xaa
                165                 170                 175

Xaa Xaa Xaa Xaa Xaa Xaa Xaa Xaa Xaa Xaa Xaa Xaa Arg Cys Thr
            180                 185                 190

Ser Pro Arg Arg Leu Ala Asn
        195
```

```
<210> SEQ ID NO 41
<211> LENGTH: 199
<212> TYPE: PRT
<213> ORGANISM: Homo sapiens
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(61)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (174)..(189)
<223> OTHER INFORMATION: Xaa can be any naturally occurring amino acid

<400> SEQUENCE: 41

Cys Pro Ala Ala Cys Thr Cys Ser Asn Ile Val Asp Cys Arg Gly
 1               5                  10                  15

Lys Gly Leu Thr Glu Ile Pro Thr Asn Leu Pro Glu Thr Ile Thr Glu
```

```
                20                  25                  30
Ile Arg Leu Glu Gln Asn Thr Ile Lys Val Ile Pro Pro Gly Ala Phe
            35                  40                  45

Ser Pro Tyr Lys Lys Leu Arg Xaa Ile Xaa Xaa Xaa Xaa Asn Gln Ile
 50                  55                  60

Ser Glu Leu Ala Pro Asp Ala Phe Gln Gly Leu Arg Ser Leu Asn Xaa
 65                  70                  75                  80

Leu Xaa Leu Xaa Xaa Asn Lys Ile Thr Glu Leu Pro Lys Ser Leu Phe
            85                  90                  95

Glu Gly Leu Phe Ser Leu Gln Xaa Leu Xaa Leu Xaa Xaa Asn Lys Ile
                100                 105                 110

Asn Cys Leu Arg Val Asp Ala Phe Gln Asp Leu His Asn Leu Asn Tyr
            115                 120                 125

Leu Asp Leu Asn Asn Lys Leu Gln Thr Ile Ala Lys Gly Thr Phe
        130                 135                 140

Ser Pro Leu Arg Ala Ile Gln His Met Trp Leu Tyr Xaa Asn Pro Phe
145                 150                 155                 160

Ile Cys Asp Cys His Leu Lys Trp Leu Ala Asp Tyr Leu Xaa Xaa Xaa
                165                 170                 175

Xaa Xaa Xaa Xaa Xaa Xaa Xaa Xaa Xaa Xaa Xaa Xaa Arg Cys Thr
            180                 185                 190

Ser Pro Arg Arg Leu Ala Asn
            195
```

<210> SEQ ID NO 42
<211> LENGTH: 199
<212> TYPE: PRT
<213> ORGANISM: Homo sapiens
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (174)..(189)
<223> OTHER INFORMATION: Xaa can be any naturally occurring amino acid

<400> SEQUENCE: 42

```
Cys Pro Ala Ala Cys Thr Cys Ser Asn Asn Ile Val Asp Cys Arg Gly
 1               5                   10                  15

Lys Gly Leu Thr Glu Ile Pro Thr Asn Leu Pro Glu Thr Ile Thr Glu
```

```
                    20                  25                  30

Ile Arg Leu Glu Gln Asn Thr Ile Lys Val Ile Pro Pro Gly Ala Phe
            35                  40                  45

Ser Pro Tyr Lys Lys Leu Arg Arg Ile Asp Leu Ser Asn Asn Gln Ile
50                  55                  60

Ser Glu Leu Ala Pro Asp Ala Phe Gln Gly Leu Arg Ser Leu Asn Xaa
65                  70                  75                  80

Leu Xaa Leu Xaa Xaa Asn Lys Ile Thr Glu Leu Pro Lys Ser Leu Phe
                85                  90                  95

Glu Gly Leu Phe Ser Leu Gln Xaa Leu Xaa Leu Xaa Xaa Asn Lys Ile
                100                 105                 110

Asn Cys Leu Arg Val Asp Ala Phe Gln Asp Leu His Asn Leu Asn Tyr
            115                 120                 125

Leu Asp Leu Asn Asn Lys Leu Gln Thr Ile Ala Lys Gly Thr Phe
        130                 135                 140

Ser Pro Leu Arg Ala Ile Gln His Met Trp Leu Tyr Xaa Asn Pro Phe
145                 150                 155                 160

Ile Cys Asp Cys His Leu Lys Trp Leu Ala Asp Tyr Leu Xaa Xaa Xaa
                165                 170                 175

Xaa Xaa Xaa Xaa Xaa Xaa Xaa Xaa Xaa Xaa Xaa Xaa Arg Cys Thr
            180                 185                 190

Ser Pro Arg Arg Leu Ala Asn
        195

<210> SEQ ID NO 43
<211> LENGTH: 199
<212> TYPE: PRT
<213> ORGANISM: Homo sapiens
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (174)..(189)
<223> OTHER INFORMATION: Xaa can be any naturally occurring amino acid

<400> SEQUENCE: 43

Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Glu
                20                  25                  30

Ile Arg Leu Glu Gln Asn Thr Ile Lys Val Ile Pro Pro Gly Ala Phe
            35                  40                  45
```

-continued

```
Ser Pro Tyr Lys Lys Leu Arg Arg Ile Asp Leu Ser Asn Asn Gln Ile
 50                  55                  60

Ser Glu Leu Ala Pro Asp Ala Phe Gln Gly Leu Arg Ser Leu Asn Ser
 65                  70                  75                  80

Leu Xaa Leu Xaa Gly Asn Lys Ile Thr Glu Leu Pro Lys Ser Leu Phe
                 85                  90                  95

Glu Gly Leu Phe Ser Leu Gln Xaa Leu Xaa Leu Xaa Xaa Asn Lys Ile
                100                 105                 110

Asn Cys Leu Arg Val Asp Ala Phe Gln Asp Leu His Asn Leu Asn Tyr
                115                 120                 125

Leu Asp Leu Asn Asn Asn Lys Leu Gln Thr Ile Ala Lys Gly Thr Phe
            130                 135                 140

Ser Pro Leu Arg Ala Ile Gln His Met Trp Leu Tyr Xaa Asn Pro Phe
145                 150                 155                 160

Ile Cys Asp Cys His Leu Lys Trp Leu Ala Asp Tyr Leu Xaa Xaa Xaa
                165                 170                 175

Xaa Xaa Xaa Xaa Xaa Xaa Xaa Xaa Xaa Xaa Xaa Xaa Arg Cys Thr
                180                 185                 190

Ser Pro Arg Arg Leu Ala Asn
            195
```

<210> SEQ ID NO 44
<211> LENGTH: 198
<212> TYPE: PRT
<213> ORGANISM: Homo sapiens
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (174)..(188)
<223> OTHER INFORMATION: Xaa can be any naturally occurring amino acid

<400> SEQUENCE: 44

```
Cys Pro Ala Ala Cys Thr Cys Ser Asn Asn Ile Val Asp Cys Arg Gly
 1               5                  10                  15

Lys Gly Leu Thr Glu Ile Pro Thr Asn Leu Pro Glu Thr Ile Thr Glu
                 20                  25                  30

Ile Arg Leu Glu Gln Asn Thr Ile Lys Val Ile Pro Pro Gly Ala Phe
             35                  40                  45

Ser Pro Tyr Lys Lys Leu Arg Arg Ile Asp Leu Ser Asn Asn Gln Ile
 50                  55                  60

Ser Glu Leu Ala Pro Asp Ala Phe Gln Gly Leu Arg Ser Leu Asn Ser
 65                  70                  75                  80

Leu Val Leu Tyr Gly Asn Lys Ile Thr Glu Leu Pro Lys Ser Leu Phe
                 85                  90                  95

Glu Gly Leu Phe Ser Leu Gln Xaa Leu Xaa Leu Xaa Xaa Asn Lys Ile
                100                 105                 110
```

```
Asn Cys Leu Arg Val Asp Ala Phe Gln Asp Leu His Asn Leu Asn Tyr
            115                 120                 125

Leu Asp Leu Asn Asn Asn Lys Leu Gln Thr Ile Ala Lys Gly Thr Phe
        130                 135                 140

Ser Pro Leu Arg Ala Ile Gln His Met Trp Leu Tyr Xaa Asn Pro Phe
145                 150                 155                 160

Ile Cys Asp Cys His Leu Lys Trp Leu Ala Asp Tyr Leu Xaa Xaa Xaa
                165                 170                 175

Xaa Xaa Xaa Xaa Xaa Xaa Xaa Xaa Xaa Xaa Xaa Arg Cys Thr Ser
            180                 185                 190

Pro Arg Arg Leu Ala Asn
        195

<210> SEQ ID NO 45
<211> LENGTH: 199
<212> TYPE: PRT
<213> ORGANISM: Homo sapiens
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (174)..(189)
<223> OTHER INFORMATION: Xaa can be any naturally occurring amino acid

<400> SEQUENCE: 45

Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Glu
            20                  25                  30

Ile Arg Leu Glu Gln Asn Thr Ile Lys Val Ile Pro Pro Gly Ala Phe
        35                  40                  45

Ser Pro Tyr Lys Lys Leu Arg Arg Ile Asp Leu Ser Asn Asn Gln Ile
50                  55                  60

Ser Glu Leu Ala Pro Asp Ala Phe Gln Gly Leu Arg Ser Leu Asn Ser
65                  70                  75                  80

Leu Val Leu Tyr Gly Asn Lys Ile Thr Glu Leu Pro Lys Ser Leu Phe
            85                  90                  95

Glu Gly Leu Phe Ser Leu Gln Leu Leu Leu Leu Asn Ala Asn Lys Ile
        100                 105                 110

Asn Cys Leu Arg Val Asp Ala Phe Gln Asp Leu His Asn Leu Asn Tyr
            115                 120                 125

Leu Asp Leu Asn Asn Asn Lys Leu Gln Thr Ile Ala Lys Gly Thr Phe
        130                 135                 140

Ser Pro Leu Arg Ala Ile Gln His Met Trp Leu Tyr Xaa Asn Pro Phe
145                 150                 155                 160

Ile Cys Asp Cys His Leu Lys Trp Leu Ala Asp Tyr Leu Xaa Xaa Xaa
                165                 170                 175

Xaa Xaa Xaa Xaa Xaa Xaa Xaa Xaa Xaa Xaa Xaa Xaa Arg Cys Thr
            180                 185                 190

Ser Pro Arg Arg Leu Ala Asn
            195

<210> SEQ ID NO 46
<211> LENGTH: 182
<212> TYPE: PRT
<213> ORGANISM: Homo sapiens
```

<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(20)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (41)..(44)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (91)..(92)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (157)..(172)
<223> OTHER INFORMATION: Xaa can be any naturally occurring amino acid

<400> SEQUENCE: 46

```
Gly Leu Thr Glu Ile Pro Thr Asn Leu Pro Glu Thr Ile Thr Xaa Ile
1               5                   10                  15

Xaa Xaa Xaa Xaa Asn Thr Ile Lys Val Ile Pro Pro Gly Ala Phe Ser
            20                  25                  30

Pro Tyr Lys Lys Leu Arg Xaa Ile Xaa Xaa Xaa Xaa Asn Gln Ile Ser
        35                  40                  45

Glu Leu Ala Pro Asp Ala Phe Gln Gly Leu Arg Ser Leu Asn Xaa Leu
    50                  55                  60

Xaa Leu Xaa Xaa Asn Lys Ile Thr Glu Leu Pro Lys Ser Leu Phe Glu
65                  70                  75                  80

Gly Leu Phe Ser Leu Gln Xaa Leu Xaa Leu Xaa Xaa Asn Lys Ile Asn
                85                  90                  95

Cys Leu Arg Val Asp Ala Phe Gln Asp Leu His Asn Leu Asn Tyr Leu
            100                 105                 110

Asp Leu Asn Asn Asn Lys Leu Gln Thr Ile Ala Lys Gly Thr Phe Ser
        115                 120                 125

Pro Leu Arg Ala Ile Gln His Met Trp Leu Tyr Xaa Asn Pro Phe Ile
    130                 135                 140

Cys Asp Cys His Leu Lys Trp Leu Ala Asp Tyr Leu Xaa Xaa Xaa Xaa
```

```
                145                 150                 155                 160
Xaa Xaa Xaa Xaa Xaa Xaa Xaa Xaa Xaa Xaa Xaa Xaa Arg Cys Thr Ser
                    165                 170                 175

Pro Arg Arg Leu Ala Asn
            180

<210> SEQ ID NO 47
<211> LENGTH: 153
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (38)..(39)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (62)..(63)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (128)..(143)
<223> OTHER INFORMATION: Xaa can be any naturally occurring amino acid

<400> SEQUENCE: 47

Ala Phe Ser Pro Tyr Lys Lys Leu Arg Xaa Ile Xaa Xaa Xaa Xaa Asn
1               5                   10                  15

Gln Ile Ser Glu Leu Ala Pro Asp Ala Phe Gln Gly Leu Arg Ser Leu
                20                  25                  30

Asn Xaa Leu Xaa Leu Xaa Xaa Asn Lys Ile Thr Glu Leu Pro Lys Ser
            35                  40                  45

Leu Phe Glu Gly Leu Phe Ser Leu Gln Xaa Leu Xaa Leu Xaa Xaa Asn
        50                  55                  60

Lys Ile Asn Cys Leu Arg Val Asp Ala Phe Gln Asp Leu His Asn Leu
65                  70                  75                  80

Asn Tyr Leu Asp Leu Asn Asn Asn Lys Leu Gln Thr Ile Ala Lys Gly
                85                  90                  95

Thr Phe Ser Pro Leu Arg Ala Ile Gln His Met Trp Leu Tyr Xaa Asn
            100                 105                 110

Pro Phe Ile Cys Asp Cys His Leu Lys Trp Leu Ala Asp Tyr Leu Xaa
        115                 120                 125
```

```
Xaa Xaa Xaa Xaa Xaa Xaa Xaa Xaa Xaa Xaa Xaa Xaa Xaa Arg
    130                 135                 140

Cys Thr Ser Pro Arg Arg Leu Ala Asn
145                 150

<210> SEQ ID NO 48
<211> LENGTH: 129
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (38)..(39)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (104)..(119)
<223> OTHER INFORMATION: Xaa can be any naturally occurring amino acid

<400> SEQUENCE: 48

Ala Phe Gln Gly Leu Arg Ser Leu Asn Xaa Leu Xaa Leu Xaa Xaa Asn
1               5                   10                  15

Lys Ile Thr Glu Leu Pro Lys Ser Leu Phe Glu Gly Leu Phe Ser Leu
                20                  25                  30

Gln Xaa Leu Xaa Leu Xaa Xaa Asn Lys Ile Asn Cys Leu Arg Val Asp
        35                  40                  45

Ala Phe Gln Asp Leu His Asn Leu Asn Tyr Leu Asp Leu Asn Asn Asn
    50                  55                  60

Lys Leu Gln Thr Ile Ala Lys Gly Thr Phe Ser Pro Leu Arg Ala Ile
65                  70                  75                  80

Gln His Met Trp Leu Tyr Xaa Asn Pro Phe Ile Cys Asp Cys His Leu
                85                  90                  95

Lys Trp Leu Ala Asp Tyr Leu Xaa Xaa Xaa Xaa Xaa Xaa Xaa Xaa Xaa
            100                 105                 110

Xaa Xaa Xaa Xaa Xaa Xaa Xaa Arg Cys Thr Ser Pro Arg Arg Leu Ala
        115                 120                 125

Asn

<210> SEQ ID NO 49
<211> LENGTH: 93
<212> TYPE: PRT
<213> ORGANISM: Homo sapiens
<220> FEATURE:
```

```
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid

<400> SEQUENCE: 49

Leu Xaa Leu Xaa Gly Asn Lys Ile Thr Glu Leu Pro Lys Ser Leu Phe
1               5                   10                  15

Glu Gly Leu Phe Ser Leu Gln Xaa Leu Xaa Leu Xaa Xaa Asn Lys Ile
            20                  25                  30

Asn Cys Leu Arg Val Asp Ala Phe Gln Asp Leu His Asn Leu Asn Tyr
        35                  40                  45

Leu Asp Leu Asn Asn Asn Lys Leu Gln Thr Ile Ala Lys Gly Thr Phe
    50                  55                  60

Ser Pro Leu Arg Ala Ile Gln His Met Trp Leu Tyr Xaa Asn Pro Phe
65                  70                  75                  80

Ile Cys Asp Cys His Leu Lys Trp Leu Ala Asp Tyr Leu
                85                  90

<210> SEQ ID NO 50
<211> LENGTH: 72
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid

<400> SEQUENCE: 50

Leu Gln Xaa Leu Xaa Leu Xaa Xaa Asn Lys Ile Asn Cys Leu Arg Val
1               5                   10                  15

Asp Ala Phe Gln Asp Leu His Asn Leu Asn Tyr Leu Asp Leu Asn Asn
            20                  25                  30

Asn Lys Leu Gln Thr Ile Ala Lys Gly Thr Phe Ser Pro Leu Arg Ala
        35                  40                  45

Ile Gln His Met Trp Leu Tyr Xaa Asn Pro Phe Ile Cys Asp Cys His
    50                  55                  60
```

```
Leu Lys Trp Leu Ala Asp Tyr Leu
 65                  70
```

<210> SEQ ID NO 51
<211> LENGTH: 55
<212> TYPE: PRT
<213> ORGANISM: Homo sapiens
<220> FEATURE:
<221> NAME/KEY: misc_feature
<222> LOCATION: (39)..(39)
<223> OTHER INFORMATION: Xaa can be any naturally occurring amino acid

<400> SEQUENCE: 51

```
Ala Phe Gln Asp Leu His Asn Leu Asn Tyr Leu Asp Leu Asn Asn Asn
1               5                   10                  15

Lys Leu Gln Thr Ile Ala Lys Gly Thr Phe Ser Pro Leu Arg Ala Ile
            20                  25                  30

Gln His Met Trp Leu Tyr Xaa Asn Pro Phe Ile Cys Asp Cys His Leu
        35                  40                  45

Lys Trp Leu Ala Asp Tyr Leu
    50                  55
```

<210> SEQ ID NO 52
<211> LENGTH: 16
<212> TYPE: PRT
<213> ORGANISM: Homo sapiens
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 52

```
Tyr Xaa Xaa Leu Xaa Xaa Xaa Xaa Xaa Xaa Xaa Xaa Tyr Xaa Xaa Leu
1               5                   10                  15
```

<210> SEQ ID NO 53
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: Xaa can be any naturally occurring amino acid

<400> SEQUENCE: 53

```
Xaa Xaa Xaa Xaa Xaa Xaa Xaa Xaa
1               5
```

<210> SEQ ID NO 54
<211> LENGTH: 132
<212> TYPE: PRT
<213> ORGANISM: Homo sapiens

<400> SEQUENCE: 54

```
Asp Pro Lys Leu Cys Tyr Leu Leu Asp Gly Ile Leu Phe Ile Tyr Gly
1               5                   10                  15

Val Ile Leu Thr Ala Leu Phe Leu Arg Val Lys Phe Ser Arg Ser Ala
            20                  25                  30
```

```
Asp Ala Pro Ala Tyr Gln Gln Gly Gln Asn Gln Leu Tyr Asn Glu Leu
        35                  40                  45

Asn Leu Gly Arg Arg Glu Glu Tyr Asp Val Leu Asp Lys Arg Arg Gly
 50                  55                  60

Arg Asp Pro Glu Met Gly Gly Lys Pro Gln Arg Arg Lys Asn Pro Gln
 65                  70                  75                  80

Glu Gly Leu Tyr Asn Glu Leu Gln Lys Asp Lys Met Ala Glu Ala Tyr
                 85                  90                  95

Ser Glu Ile Gly Met Lys Gly Glu Arg Arg Arg Gly Lys Gly His Asp
            100                 105                 110

Gly Leu Tyr Gln Gly Leu Ser Thr Ala Thr Lys Asp Thr Tyr Asp Ala
        115                 120                 125

Leu His Met Gln
        130

<210> SEQ ID NO 55
<211> LENGTH: 62
<212> TYPE: PRT
<213> ORGANISM: Homo sapiens

<400> SEQUENCE: 55

Glu Pro Gln Leu Cys Tyr Ile Leu Asp Ala Ile Leu Phe Leu Tyr Gly
 1               5                  10                  15

Ile Val Leu Thr Leu Leu Tyr Cys Arg Leu Lys Ile Gln Val Arg Lys
            20                  25                  30

Ala Ala Ile Thr Ser Tyr Glu Lys Ser Asp Gly Val Tyr Thr Gly Leu
        35                  40                  45

Ser Thr Arg Asn Gln Glu Thr Tyr Glu Thr Leu Lys His Glu
 50                  55                  60

<210> SEQ ID NO 56
<211> LENGTH: 193
<212> TYPE: PRT
<213> ORGANISM: Homo sapiens

<400> SEQUENCE: 56

Ala Cys Pro Ser Gln Cys Ser Cys Pro Gly Thr Asp Val Asn Cys His
 1               5                  10                  15

Glu Arg Arg Leu Ala Ser Val Pro Ala Glu Ile Pro Thr Thr Thr Lys
            20                  25                  30

Ile Leu Arg Leu Tyr Ile Asn Gln Ile Thr Lys Leu Glu Pro Gly Val
        35                  40                  45

Phe Asp Arg Leu Thr Gln Leu Thr Gln Leu Gly Leu Trp Asp Asn Gln
 50                  55                  60

Leu Gln Ala Leu Pro Glu Gly Val Phe Asp Arg Leu Val Asn Leu Gln
 65                  70                  75                  80

Lys Leu Tyr Leu Asn Gln Asn Gln Leu Leu Ala Leu Pro Val Gly Val
                 85                  90                  95

Phe Asp Lys Leu Thr Gln Leu Thr Tyr Leu Asp Leu Asn Asn Asn Gln
            100                 105                 110

Leu Lys Ser Ile Pro Arg Gly Ala Phe Asp Asn Leu Lys Ser Leu Thr
        115                 120                 125

His Ile Trp Leu Tyr Gly Asn Pro Trp Asp Cys Glu Cys Ser Asp Ile
        130                 135                 140

Leu Tyr Leu Lys Asn Trp Ile Val Gln His Ala Ser Ile Val Asn Pro
145                 150                 155                 160
```

His Pro Tyr Gly Gly Val Asp Asn Val Lys Cys Ser Gly Thr Asn Thr
                165                 170                 175

Pro Val Arg Ala Val Thr Glu Ala Ser Thr Ser Pro Ser Lys Cys Pro
            180                 185                 190

Gly

<210> SEQ ID NO 57
<211> LENGTH: 294
<212> TYPE: PRT
<213> ORGANISM: Homo sapiens

<400> SEQUENCE: 57

Met Trp Ile Lys Trp Ile Ala Thr Leu Val Ala Phe Gly Ala Leu Val
1               5                   10                  15

Gln Ser Ala Val Ala Cys Pro Ser Gln Cys Ser Cys Pro Gly Thr Asp
            20                  25                  30

Val Asn Cys His Glu Arg Arg Leu Ala Ser Val Pro Ala Glu Ile Pro
        35                  40                  45

Thr Thr Thr Lys Ile Leu Arg Leu Tyr Ile Asn Gln Ile Thr Lys Leu
    50                  55                  60

Glu Pro Gly Val Phe Asp Arg Leu Thr Gln Leu Thr Gln Leu Gly Leu
65                  70                  75                  80

Trp Asp Asn Gln Leu Gln Ala Leu Pro Glu Gly Val Phe Asp Arg Leu
                85                  90                  95

Val Asn Leu Gln Lys Leu Tyr Leu Asn Gln Asn Gln Leu Leu Ala Leu
            100                 105                 110

Pro Val Gly Val Phe Asp Lys Leu Thr Gln Leu Thr Tyr Leu Asp Leu
        115                 120                 125

Asn Asn Asn Gln Leu Lys Ser Ile Pro Arg Gly Ala Phe Asp Asn Leu
    130                 135                 140

Lys Ser Leu Thr His Ile Trp Leu Tyr Gly Asn Pro Trp Asp Cys Glu
145                 150                 155                 160

Cys Ser Asp Ile Leu Tyr Leu Lys Asn Trp Ile Val Gln His Ala Ser
                165                 170                 175

Ile Val Asn Pro His Pro Tyr Gly Gly Val Asp Asn Val Lys Cys Ser
            180                 185                 190

Gly Thr Asn Thr Pro Val Arg Ala Val Thr Glu Ala Ser Thr Ser Pro
        195                 200                 205

Ser Lys Cys Pro Gly Tyr Val Ala Thr Thr Thr Thr Pro Thr Thr Thr
    210                 215                 220

Thr Pro Glu Phe Ile Pro Glu Thr Thr Thr Ser Pro Gln Pro Val Ile
225                 230                 235                 240

Thr Thr Gln Lys Pro Lys Pro Leu Trp Asn Phe Asn Cys Thr Ser Ile
                245                 250                 255

Gln Glu Arg Lys Asn Asp Gly Gly Asp Cys Gly Lys Pro Ala Cys Thr
            260                 265                 270

Thr Leu Leu Asn Cys Ala Asn Phe Leu Ser Cys Leu Cys Ser Thr Cys
        275                 280                 285

Ala Leu Cys Arg Lys Arg
    290

<210> SEQ ID NO 58
<211> LENGTH: 199
<212> TYPE: PRT
<213> ORGANISM: Homo sapiens

<400> SEQUENCE: 58

| Cys | Pro | Ala | Ala | Cys | Thr | Cys | Ser | Asn | Asn | Ile | Val | Asp | Cys | Arg | Gly |
|---|---|---|---|---|---|---|---|---|---|---|---|---|---|---|---|
| 1 | | | | 5 | | | | | 10 | | | | | 15 | |

Lys Gly Leu Thr Glu Ile Pro Thr Asn Leu Pro Glu Thr Ile Thr Glu
               20              25              30

Ile Arg Leu Glu Gln Asn Thr Ile Lys Val Ile Pro Pro Gly Ala Phe
        35               40              45

Ser Pro Tyr Lys Lys Leu Arg Arg Ile Asp Leu Ser Asn Asn Gln Ile
50               55              60

Ser Glu Leu Ala Pro Asp Ala Phe Gln Gly Leu Arg Ser Leu Asn Ser
65              70             75             80

Leu Val Leu Tyr Gly Asn Lys Ile Thr Glu Leu Pro Lys Ser Leu Phe
             85              90            95

Glu Gly Leu Phe Ser Leu Gln Leu Leu Tyr Leu Asn Ala Asn Lys Ile
          100            105           110

Asn Cys Leu Arg Val Asp Ala Phe Gln Asp Leu His Asn Leu Asn Tyr
          115            120           125

Leu Asp Leu Asn Asn Asn Lys Leu Gln Thr Ile Ala Lys Gly Thr Phe
          130            135           140

Ser Pro Leu Arg Ala Ile Gln His Ile Trp Leu Tyr Gln Asn Pro Phe
145              150             155           160

Ile Cys Asp Cys His Leu Lys Trp Leu Ala Asp Tyr Leu His Ala Ser
          165            170           175

Ile Val Asn Pro His Pro Tyr Gly Gly Val Asp Asn Ala Arg Cys Thr
          180            185           190

Ser Pro Arg Arg Leu Ala Asn
          195

<210> SEQ ID NO 59
<211> LENGTH: 196
<212> TYPE: PRT
<213> ORGANISM: Homo sapiens

<400> SEQUENCE: 59

Cys Pro Ala Ala Cys Thr Cys Ser Asn Asn Ile Val Asp Cys Arg Gly
1               5              10            15

Lys Gly Leu Thr Glu Ile Pro Thr Asn Leu Pro Glu Thr Ile Thr Glu
          20             25            30

Ile Arg Leu Glu Gln Asn Thr Ile Lys Val Ile Pro Pro Gly Ala Phe
        35               40              45

Ser Pro Tyr Lys Lys Leu Arg Arg Ile Asp Leu Ser Asn Asn Gln Ile
50               55              60

Ser Glu Leu Ala Pro Asp Ala Phe Gln Gly Leu Arg Ser Leu Asn Ser
65              70             75             80

Leu Val Leu Tyr Gly Asn Lys Ile Thr Glu Leu Pro Lys Ser Leu Phe
             85              90            95

Glu Gly Leu Phe Ser Leu Gln Leu Leu Tyr Leu Asn Ala Asn Lys Ile
          100            105           110

Asn Cys Leu Arg Val Asp Ala Phe Gln Asp Leu His Asn Leu Asn Tyr
          115            120           125

Leu Asp Leu Asn Asn Asn Lys Leu Gln Thr Ile Ala Lys Gly Thr Phe
          130            135           140

Ser Pro Leu Arg Ala Ile Gln His Ile Trp Leu Tyr Gln Asn Pro Phe
145              150             155           160

```
Ile Cys Asp Cys His Leu Lys Trp Leu Ala Asp Tyr Leu Ser Ile Val
                165                 170                 175

Asn Pro His Pro Tyr Gly Gly Val Asp Ala Arg Cys Thr Ser Pro Arg
            180                 185                 190

Arg Leu Ala Asn
        195

<210> SEQ ID NO 60
<211> LENGTH: 201
<212> TYPE: PRT
<213> ORGANISM: Homo sapiens

<400> SEQUENCE: 60

Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Glu
            20                  25                  30

Ile Arg Leu Glu Gln Asn Thr Ile Lys Val Ile Pro Pro Gly Ala Phe
        35                  40                  45

Ser Pro Tyr Lys Lys Leu Arg Arg Ile Asp Leu Ser Asn Asn Gln Ile
50                  55                  60

Ser Glu Leu Ala Pro Asp Ala Phe Gln Gly Leu Arg Ser Leu Asn Ser
65                  70                  75                  80

Leu Val Leu Tyr Gly Asn Lys Ile Thr Glu Leu Pro Lys Ser Leu Phe
                85                  90                  95

Glu Gly Leu Phe Ser Leu Gln Leu Leu Tyr Leu Asn Ala Asn Lys Ile
            100                 105                 110

Asn Cys Leu Arg Val Asp Ala Phe Gln Asp Leu His Asn Leu Asn Tyr
        115                 120                 125

Leu Asp Leu Asn Asn Asn Lys Leu Gln Thr Ile Ala Lys Gly Thr Phe
130                 135                 140

Ser Pro Leu Arg Ala Ile Gln His Ile Trp Leu Tyr Gln Asn Pro Phe
145                 150                 155                 160

Ile Cys Asp Cys His Leu Lys Trp Leu Ala Asp Tyr Leu Ile Val Gln
                165                 170                 175

His Ala Ser Ile Val Asn Pro His Pro Tyr Gly Gly Val Asp Ala Arg
            180                 185                 190

Cys Thr Ser Pro Arg Arg Leu Ala Asn
        195                 200

<210> SEQ ID NO 61
<211> LENGTH: 199
<212> TYPE: PRT
<213> ORGANISM: Homo sapiens

<400> SEQUENCE: 61

Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Glu
            20                  25                  30

Ile Arg Leu Glu Gln Asn Thr Ile Lys Val Ile Pro Pro Gly Ala Phe
        35                  40                  45

Ser Pro Tyr Lys Lys Leu Arg Arg Ile Asp Leu Ser Asn Asn Gln Ile
50                  55                  60

Ser Glu Leu Ala Pro Asp Ala Phe Gln Gly Leu Arg Ser Leu Asn Ser
65                  70                  75                  80
```

```
Leu Val Leu Tyr Gly Asn Lys Ile Thr Glu Leu Pro Lys Ser Leu Phe
                85                  90                  95

Glu Gly Leu Phe Ser Leu Gln Leu Leu Leu Asn Ala Asn Lys Ile
            100                 105                 110

Asn Cys Leu Arg Val Asp Ala Phe Gln Asp Leu His Asn Leu Asn Tyr
            115                 120                 125

Leu Asp Leu Asn Asn Lys Leu Gln Thr Ile Ala Lys Gly Thr Phe
130                 135                 140

Ser Pro Leu Arg Ala Ile Gln His Ile Trp Leu Tyr Gln Asn Pro Phe
145                 150                 155                 160

Ile Cys Asp Cys His Leu Lys Trp Leu Ala Asp Tyr Leu His Ala Ser
                165                 170                 175

Ile Val Asn Pro His Pro Tyr Gly Gly Val Asp Asn Ala Arg Cys Thr
                180                 185                 190

Ser Pro Arg Arg Leu Ala Asn
            195

<210> SEQ ID NO 62
<211> LENGTH: 196
<212> TYPE: PRT
<213> ORGANISM: Homo sapiens

<400> SEQUENCE: 62

Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Glu
            20                  25                  30

Ile Arg Leu Glu Gln Asn Thr Ile Lys Val Ile Pro Pro Gly Ala Phe
        35                  40                  45

Ser Pro Tyr Lys Lys Leu Arg Arg Ile Asp Leu Ser Asn Asn Gln Ile
    50                  55                  60

Ser Glu Leu Ala Pro Asp Ala Phe Gln Gly Leu Arg Ser Leu Asn Ser
65                  70                  75                  80

Leu Val Leu Tyr Gly Asn Lys Ile Thr Glu Leu Pro Lys Ser Leu Phe
                85                  90                  95

Glu Gly Leu Phe Ser Leu Gln Leu Leu Leu Asn Ala Asn Lys Ile
            100                 105                 110

Asn Cys Leu Arg Val Asp Ala Phe Gln Asp Leu His Asn Leu Asn Tyr
            115                 120                 125

Leu Asp Leu Asn Asn Lys Leu Gln Thr Ile Ala Lys Gly Thr Phe
130                 135                 140

Ser Pro Leu Arg Ala Ile Gln His Ile Trp Leu Tyr Gln Asn Pro Phe
145                 150                 155                 160

Ile Cys Asp Cys His Leu Lys Trp Leu Ala Asp Tyr Leu Ser Ile Val
                165                 170                 175

Asn Pro His Pro Tyr Gly Gly Val Asp Ala Arg Cys Thr Ser Pro Arg
            180                 185                 190

Arg Leu Ala Asn
        195

<210> SEQ ID NO 63
<211> LENGTH: 201
<212> TYPE: PRT
<213> ORGANISM: Homo sapiens

<400> SEQUENCE: 63
```

```
Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Glu
            20                  25                  30

Ile Arg Leu Glu Gln Asn Thr Ile Lys Val Ile Pro Pro Gly Ala Phe
            35                  40                  45

Ser Pro Tyr Lys Lys Leu Arg Arg Ile Asp Leu Ser Asn Asn Gln Ile
50                      55                  60

Ser Glu Leu Ala Pro Asp Ala Phe Gln Gly Leu Arg Ser Leu Asn Ser
65                  70                  75                  80

Leu Val Leu Tyr Gly Asn Lys Ile Thr Glu Leu Pro Lys Ser Leu Phe
                85                  90                  95

Glu Gly Leu Phe Ser Leu Gln Leu Leu Leu Asn Ala Asn Lys Ile
                100                 105                 110

Asn Cys Leu Arg Val Asp Ala Phe Gln Asp Leu His Asn Leu Asn Tyr
            115                 120                 125

Leu Asp Leu Asn Asn Asn Lys Leu Gln Thr Ile Ala Lys Gly Thr Phe
        130                 135                 140

Ser Pro Leu Arg Ala Ile Gln His Ile Trp Leu Tyr Gln Asn Pro Phe
145                 150                 155                 160

Ile Cys Asp Cys His Leu Lys Trp Leu Ala Asp Tyr Leu Ile Val Gln
                165                 170                 175

His Ala Ser Ile Val Asn Pro His Pro Tyr Gly Gly Val Asp Ala Arg
            180                 185                 190

Cys Thr Ser Pro Arg Arg Leu Ala Asn
            195                 200

<210> SEQ ID NO 64
<211> LENGTH: 199
<212> TYPE: PRT
<213> ORGANISM: Homo sapiens

<400> SEQUENCE: 64

Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Glu
            20                  25                  30

Ile Arg Leu Glu Gln Asn Thr Ile Lys Val Ile Pro Pro Gly Ala Phe
            35                  40                  45

Ser Pro Tyr Lys Lys Leu Arg Ile Leu Arg Leu Tyr Ile Asn Gln Ile
50                      55                  60

Ser Glu Leu Ala Pro Asp Ala Phe Gln Gly Leu Arg Ser Leu Asn Gln
65                  70                  75                  80

Leu Val Leu Trp Asp Asn Lys Ile Thr Glu Leu Pro Lys Ser Leu Phe
                85                  90                  95

Glu Gly Leu Phe Ser Leu Gln Leu Leu Tyr Leu Asn Ala Asn Lys Ile
                100                 105                 110

Asn Cys Leu Arg Val Asp Ala Phe Gln Asp Leu His Asn Leu Asn Tyr
            115                 120                 125

Leu Asp Leu Asn Asn Asn Lys Leu Gln Thr Ile Ala Lys Gly Thr Phe
        130                 135                 140

Ser Pro Leu Arg Ala Ile Gln His Ile Trp Leu Tyr Gly Asn Pro Phe
145                 150                 155                 160

Ile Cys Asp Cys His Leu Lys Trp Leu Ala Asp Tyr Leu His Ala Ser
```

```
                    165                 170                 175
Ile Val Asn Pro His Pro Tyr Gly Gly Val Asp Asn Ala Arg Cys Thr
                180                 185                 190

Ser Pro Arg Arg Leu Ala Asn
            195

<210> SEQ ID NO 65
<211> LENGTH: 71
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid

<400> SEQUENCE: 65

Xaa Leu Xaa Leu Xaa Xaa Asn Lys Ile Asn Cys Leu Arg Val Asp Ala
1               5                   10                  15

Phe Gln Asp Leu His Asn Leu Asn Xaa Leu Xaa Leu Xaa Xaa Asn Lys
            20                  25                  30

Leu Gln Thr Ile Ala Lys Gly Thr Phe Ser Pro Leu Arg Ala Ile Gln
        35                  40                  45

Xaa Met Xaa Leu Xaa Xaa Asn Pro Phe Ile Cys Asp Cys His Leu Lys
    50                  55                  60

Trp Leu Ala Asp Tyr Leu His
65                  70

<210> SEQ ID NO 66
<211> LENGTH: 32
<212> TYPE: PRT
<213> ORGANISM: Homo sapiens

<400> SEQUENCE: 66

Tyr Leu Asp Leu Asn Asn Asn Lys Leu Gln Thr Ile Ala Lys Gly Thr
1               5                   10                  15

Phe Gly Thr Phe Ser Pro Leu Arg Ala Ile Gln His Met Trp Leu Tyr
```

<210> SEQ ID NO 67
<211> LENGTH: 33
<212> TYPE: PRT
<213> ORGANISM: Homo sapiens

<400> SEQUENCE: 67

Tyr Leu Asp Leu Asn Asn Asn Lys Leu Gln Thr Ile Ala Lys Gly Thr
1               5                   10                  15

Phe Gly Thr Phe Ser Pro Leu Arg Ala Ile Gln His Met Trp Leu Tyr
            20                  25                  30

Gln

<210> SEQ ID NO 68
<211> LENGTH: 33
<212> TYPE: PRT
<213> ORGANISM: Homo sapiens

<400> SEQUENCE: 68

Tyr Leu Asp Leu Asn Asn Asn Lys Leu Gln Thr Ile Ala Lys Gly Thr
1               5                   10                  15

Phe Gly Thr Phe Ser Pro Leu Arg Ala Ile Gln His Met Trp Leu Tyr
            20                  25                  30

Gly

<210> SEQ ID NO 69
<211> LENGTH: 43
<212> TYPE: PRT
<213> ORGANISM: Homo sapiens

<400> SEQUENCE: 69

Lys Leu Thr Gln Leu Thr Tyr Leu Asp Leu Asn Asn Asn Gln Leu Lys
1               5                   10                  15

Ser Ile Pro Arg Gly Ala Phe Asp Asn Leu Lys Ser Leu Thr His Ile
            20                  25                  30

Trp Leu Tyr Gly Asn Pro Trp Asp Cys Glu Cys
        35                  40

<210> SEQ ID NO 70
<211> LENGTH: 43
<212> TYPE: PRT
<213> ORGANISM: Homo sapiens

<400> SEQUENCE: 70

Asp Leu His Asn Leu Asn Leu Ser Leu Tyr Asp Asn Lys Leu Gln
1               5                   10                  15

Thr Ile Ala Lys Gly Thr Phe Ser Pro Leu Arg Ala Ile Gln Thr Met
            20                  25                  30

His Leu Ala Gln Asn Pro Phe Ile Cys Asp Cys
        35                  40

<210> SEQ ID NO 71
<211> LENGTH: 43
<212> TYPE: PRT
<213> ORGANISM: Homo sapiens

<400> SEQUENCE: 71

Asp Leu His Asn Leu Asn Tyr Leu Asp Leu Asn Asn Lys Leu Gln
1               5                   10                  15

Thr Ile Ala Lys Gly Thr Phe Ser Pro Leu Arg Ala Ile Gln His Met
            20                  25                  30

Trp Leu Tyr Gln Asn Pro Phe Ile Cys Asp Cys
            35                  40

<210> SEQ ID NO 72
<211> LENGTH: 206
<212> TYPE: PRT
<213> ORGANISM: Homo sapiens

<400> SEQUENCE: 72

Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Glu
            20                  25                  30

Ile Arg Leu Glu Gln Asn Thr Ile Lys Val Ile Pro Pro Gly Ala Phe
        35                  40                  45

Ser Pro Tyr Lys Lys Leu Arg Arg Ile Asp Leu Ser Asn Asn Gln Ile
    50                  55                  60

Ser Glu Leu Ala Pro Asp Ala Phe Gln Gly Leu Arg Ser Leu Asn Ser
65                  70                  75                  80

Leu Val Leu Tyr Gly Asn Lys Ile Thr Glu Leu Pro Lys Ser Leu Phe
                85                  90                  95

Glu Gly Leu Phe Ser Leu Gln Leu Leu Leu Leu Asn Ala Asn Lys Ile
            100                 105                 110

Asn Cys Leu Arg Val Asp Ala Phe Gln Asp Leu His Asn Leu Asn Leu
        115                 120                 125

Leu Ser Leu Tyr Asp Asn Lys Leu Gln Thr Ile Ala Lys Gly Thr Phe
    130                 135                 140

Ser Pro Leu Arg Ala Ile Gln Thr Met His Leu Ala Gln Asn Pro Phe
145                 150                 155                 160

Ile Cys Asp Cys His Leu Lys Trp Leu Ala Asp Tyr Leu His Thr Asn
                165                 170                 175

Pro Ile Glu Thr Ser Gly Ala Arg Cys Thr Ser Pro Arg Arg Leu Ala
            180                 185                 190

Asn Lys Arg Ile Gly Gln Ile Lys Ser Lys Lys Phe Arg Cys
        195                 200                 205

<210> SEQ ID NO 73
<211> LENGTH: 199
<212> TYPE: PRT
<213> ORGANISM: Homo sapiens

<400> SEQUENCE: 73

Ala Cys Pro Ser Gln Cys Ser Cys Ser Gly Thr Thr Val Asp Cys Arg
1               5                   10                  15

Ser Lys Arg His Ala Ser Val Pro Ala Gly Ile Pro Thr Asn Ala Gln
            20                  25                  30

Ile Leu Tyr Leu His Asp Asn Gln Ile Thr Lys Leu Glu Pro Gly Val
        35                  40                  45

Phe Asp Ser Leu Ile Asn Leu Lys Glu Leu Tyr Leu Gly Ser Asn Gln
    50                  55                  60

Leu Gly Ala Leu Pro Val Gly Val Phe Asp Ser Leu Thr Gln Leu Thr
65                  70                  75                  80

Val Leu Asp Leu Gly Thr Asn Gln Leu Thr Val Leu Pro Ser Ala Val
                85                  90                  95

Phe Asp Arg Leu Val His Leu Lys Glu Leu Phe Met Cys Cys Asn Lys
                100                 105                 110

Leu Thr Glu Leu Pro Arg Gly Ile Glu Arg Leu Thr His Leu Thr His
            115                 120                 125

Leu Ala Leu Asp Gln Asn Gln Leu Lys Ser Ile Pro His Gly Ala Phe
        130                 135                 140

Asp Arg Leu Ser Ser Leu Thr His Ala Tyr Leu Phe Gly Asn Pro Trp
145                 150                 155                 160

Asp Cys Glu Cys Arg Asp Ile Met Tyr Leu Arg Asn Trp Val Ala Asp
                165                 170                 175

His Thr Ser Ile Ala Met Arg Trp Asp Gly Lys Ala Val Asn Asp Pro
            180                 185                 190

Asp Ser Ala Lys Cys Ala Gly
        195

<210> SEQ ID NO 74
<211> LENGTH: 200
<212> TYPE: PRT
<213> ORGANISM: Homo sapiens

<400> SEQUENCE: 74

Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Glu
                20                  25                  30

Ile Arg Leu Glu Gln Asn Thr Ile Lys Val Ile Pro Pro Gly Ala Phe
            35                  40                  45

Ser Pro Tyr Lys Lys Leu Arg Ile Leu Arg Leu Tyr Ile Asn Gln Ile
        50                  55                  60

Ser Glu Leu Ala Pro Asp Ala Phe Gln Gly Leu Arg Ser Leu Asn Gln
65                  70                  75                  80

Leu Val Leu Trp Asp Asn Lys Ile Thr Glu Leu Pro Lys Ser Leu Phe
                85                  90                  95

Glu Gly Leu Phe Ser Leu Gln Leu Tyr Leu Asn Ala Asn Lys Ile
                100                 105                 110

Asn Cys Leu Arg Val Asp Ala Phe Gln Asp Leu His Asn Leu Asn Tyr
            115                 120                 125

Leu Asp Leu Asn Asn Asn Lys Leu Gln Thr Ile Ala Lys Gly Thr Phe
        130                 135                 140

Ser Pro Leu Arg Ala Ile Gln His Ile Trp Leu Tyr Gly Asn Pro Phe
145                 150                 155                 160

Ile Cys Asp Cys His Leu Lys Trp Leu Ala Asp Tyr Leu His His Ala
                165                 170                 175

Ser Ile Val Asn Pro His Pro Tyr Gly Gly Val Asp Asn Ala Arg Cys
            180                 185                 190

Thr Ser Pro Arg Arg Leu Ala Asn
        195                 200

<210> SEQ ID NO 75
<211> LENGTH: 200
<212> TYPE: PRT
<213> ORGANISM: Homo sapiens

<400> SEQUENCE: 75

Cys Pro Ala Ala Cys Thr Cys Ser Asn Asn Ile Val Asp Cys Arg Gly
1               5                   10                  15

```
Lys Gly Leu Thr Glu Ile Pro Thr Asn Leu Pro Glu Thr Ile Thr Glu
             20                  25                  30

Ile Arg Leu Glu Gln Asn Thr Ile Lys Val Ile Pro Pro Gly Ala Phe
         35                  40                  45

Ser Pro Tyr Lys Lys Leu Arg Ile Leu Arg Leu Tyr Ile Asn Gln Ile
 50                  55                  60

Ser Glu Leu Ala Pro Asp Ala Phe Gln Gly Leu Arg Ser Leu Asn Gln
 65                  70                  75                  80

Leu Val Leu Trp Asp Asn Lys Ile Thr Glu Leu Pro Lys Ser Leu Phe
                 85                  90                  95

Glu Gly Leu Phe Ser Leu Gln Leu Leu Tyr Leu Asn Ala Asn Lys Ile
            100                 105                 110

Asn Cys Leu Arg Val Asp Ala Phe Gln Asp Leu His Asn Leu Asn Tyr
            115                 120                 125

Leu Asp Leu Asn Asn Asn Lys Leu Gln Thr Ile Ala Lys Gly Thr Phe
        130                 135                 140

Ser Pro Leu Arg Ala Ile Gln His Ile Trp Leu Tyr Gly Asn Pro Phe
145                 150                 155                 160

Ile Cys Asp Cys His Leu Lys Trp Leu Ala Asp Tyr Leu His Thr His
                165                 170                 175

Ala Ser Ile Val Asn Pro His Pro Tyr Gly Gly Val Asp Asn Arg Cys
            180                 185                 190

Thr Ser Pro Arg Arg Leu Ala Asn
        195                 200

<210> SEQ ID NO 76
<211> LENGTH: 202
<212> TYPE: PRT
<213> ORGANISM: Homo sapiens

<400> SEQUENCE: 76

Cys Pro Ala Ala Cys Thr Cys Ser Asn Asn Ile Val Asp Cys Arg Gly
1               5                  10                  15

Lys Gly Leu Thr Glu Ile Pro Thr Asn Leu Pro Glu Thr Ile Thr Glu
             20                  25                  30

Ile Arg Leu Glu Gln Asn Thr Ile Lys Val Ile Pro Pro Gly Ala Phe
         35                  40                  45

Ser Pro Tyr Lys Lys Leu Arg Ile Leu Arg Leu Tyr Ile Asn Gln Ile
 50                  55                  60

Ser Glu Leu Ala Pro Asp Ala Phe Gln Gly Leu Arg Ser Leu Asn Gln
 65                  70                  75                  80

Leu Val Leu Trp Asp Asn Lys Ile Thr Glu Leu Pro Lys Ser Leu Phe
                 85                  90                  95

Glu Gly Leu Phe Ser Leu Gln Leu Leu Tyr Leu Asn Ala Asn Lys Ile
            100                 105                 110

Asn Cys Leu Arg Val Asp Ala Phe Gln Asp Leu His Asn Leu Asn Tyr
            115                 120                 125

Leu Asp Leu Asn Asn Asn Lys Leu Gln Thr Ile Ala Lys Gly Thr Phe
        130                 135                 140

Ser Pro Leu Arg Ala Ile Gln His Ile Trp Leu Tyr Gly Asn Pro Phe
145                 150                 155                 160

Ile Cys Asp Cys His Leu Lys Trp Leu Ala Asp Tyr Leu His Thr Asn
                165                 170                 175

His Ala Ser Ile Val Asn Pro His Pro Tyr Gly Gly Val Asp Asn Ala
            180                 185                 190
```

Arg Cys Thr Ser Pro Arg Arg Leu Ala Asn
        195                 200

<210> SEQ ID NO 77
<211> LENGTH: 202
<212> TYPE: PRT
<213> ORGANISM: Homo sapiens

<400> SEQUENCE: 77

Cys Pro Ala Ala Cys Thr Cys Ser Asn Asn Ile Val Asp Cys Arg Gly
1               5                   10                  15

Lys Gly Leu Thr Glu Ile Pro Thr Asn Leu Pro Glu Thr Ile Thr Glu
            20                  25                  30

Ile Arg Leu Glu Gln Asn Thr Ile Lys Val Ile Pro Pro Gly Ala Phe
        35                  40                  45

Ser Pro Tyr Lys Lys Leu Arg Ile Leu Arg Leu Tyr Ile Asn Gln Ile
    50                  55                  60

Ser Glu Leu Ala Pro Asp Ala Phe Gln Gly Leu Arg Ser Leu Asn Gln
65                  70                  75                  80

Leu Val Leu Trp Asp Asn Lys Ile Thr Glu Leu Pro Lys Ser Leu Phe
                85                  90                  95

Glu Gly Leu Phe Ser Leu Gln Leu Tyr Leu Asn Ala Asn Lys Ile
            100                 105                 110

Asn Cys Leu Arg Val Asp Ala Phe Gln Asp Leu His Asn Leu Asn Tyr
            115                 120                 125

Leu Asp Leu Asn Asn Asn Lys Leu Gln Thr Ile Ala Lys Gly Thr Phe
        130                 135                 140

Ser Pro Leu Arg Ala Ile Gln His Ile Trp Leu Tyr Gly Asn Pro Phe
145                 150                 155                 160

Ile Cys Asp Cys His Leu Lys Trp Leu Ala Asp Tyr Leu His Thr Asn
                165                 170                 175

Pro His Ala Ser Ile Val Asn Pro His Pro Tyr Gly Gly Val Asp Asn
            180                 185                 190

Arg Cys Thr Ser Pro Arg Arg Leu Ala Asn
        195                 200

<210> SEQ ID NO 78
<211> LENGTH: 12
<212> TYPE: PRT
<213> ORGANISM: Homo sapiens

<400> SEQUENCE: 78

Cys Asp Cys His Leu Lys Trp Leu Ala Asp Tyr Leu
1               5                   10

<210> SEQ ID NO 79
<211> LENGTH: 6
<212> TYPE: PRT
<213> ORGANISM: Artificial
<220> FEATURE:
<223> OTHER INFORMATION: Synthetic construct

<400> SEQUENCE: 79

Gly Gly Gly Gly Gly Gly
1               5

<210> SEQ ID NO 80
<211> LENGTH: 5
<212> TYPE: PRT

```
<213> ORGANISM: Artificial
<220> FEATURE:
<223> OTHER INFORMATION: Synthetic construct

<400> SEQUENCE: 80

Gly Gly Gly Gly Thr
1               5

<210> SEQ ID NO 81
<211> LENGTH: 6
<212> TYPE: PRT
<213> ORGANISM: Artificial
<220> FEATURE:
<223> OTHER INFORMATION: Synthetic construct

<400> SEQUENCE: 81

Gly Gly Gly Pro Pro Pro
1               5

<210> SEQ ID NO 82
<211> LENGTH: 7
<212> TYPE: PRT
<213> ORGANISM: Artificial
<220> FEATURE:
<223> OTHER INFORMATION: Synthetic construct

<400> SEQUENCE: 82

Gly Gly Gly Ala Pro Pro Pro
1               5

<210> SEQ ID NO 83
<211> LENGTH: 4
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: Xaa can be any naturally occurring amino acid

<400> SEQUENCE: 83

Xaa Xaa Xaa Xaa
1

<210> SEQ ID NO 84
<211> LENGTH: 6
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 84

Xaa Leu Xaa Leu Xaa Xaa
1               5

<210> SEQ ID NO 85
```

-continued

```
<211> LENGTH: 6
<212> TYPE: PRT
<213> ORGANISM: Artificial
<220> FEATURE:
<223> OTHER INFORMATION: Synthetic construct

<400> SEQUENCE: 85

Leu Leu Ser Leu Asp Asp
1               5
```